(12) United States Patent
Kravchuk et al.

(10) Patent No.: US 9,812,657 B2
(45) Date of Patent: *Nov. 7, 2017

(54) ORGANOMETALLIC COMPOUND AND ORGANIC LIGHT-EMITTING DEVICE INCLUDING THE SAME

(71) Applicants: Samsung Electronics Co., Ltd., Suwon-si, Gyeonggi-do (KR); CHEIL INDUSTRIES INC., Gumi-si, Gyeongsangbuk-do (KR)

(72) Inventors: Dmitry Kravchuk, Hwaseong-si (KR); Chang-ho Noh, Suwon-si (KR); Rupasree Ragini Das, Suwon-si (KR); Virendra Kumar Rai, Hwaseong-si (KR); Kang-mun Lee, Suwon-si (KR)

(73) Assignee: SAMSUNG ELECTRONICS CO., LTD., Gyeonggi-Do (KR)

(*) Notice: Subject to any disclaimer, the term of this patent is extended or adjusted under 35 U.S.C. 154(b) by 7 days.

This patent is subject to a terminal disclaimer.

(21) Appl. No.: 14/460,407

(22) Filed: Aug. 15, 2014

(65) Prior Publication Data

US 2015/0194614 A1  Jul. 9, 2015

(30) Foreign Application Priority Data

Jan. 7, 2014 (KR) .................. 10-2014-0002080

(51) Int. Cl.
| | | |
|---|---|---|
| *C07F 15/00* | (2006.01) | |
| *H01L 51/00* | (2006.01) | |
| *C09K 11/06* | (2006.01) | |
| *H01L 51/50* | (2006.01) | |

(52) U.S. Cl.
CPC ...... *H01L 51/0085* (2013.01); *C07F 15/0033* (2013.01); *C09K 11/06* (2013.01); *C09K 2211/1007* (2013.01); *C09K 2211/1029* (2013.01); *C09K 2211/1044* (2013.01); *C09K 2211/1059* (2013.01); *C09K 2211/1088* (2013.01); *C09K 2211/1092* (2013.01); *C09K 2211/185* (2013.01); *H01L 51/5016* (2013.01); *H01L 2251/308* (2013.01)

(58) Field of Classification Search
USPC .......................... 556/52, 136, 137
See application file for complete search history.

(56) References Cited

U.S. PATENT DOCUMENTS

2004/0121184 A1   6/2004  Thompson et al.

FOREIGN PATENT DOCUMENTS

| | | | | |
|---|---|---|---|---|
| EP | 2189508 A2 | | 5/2010 | |
| JP | 2007-284549 A | | 11/2007 | |
| JP | 2014-005223 | * | 1/2014 | .......... C07D 213/34 |
| KR | 1020120050557 A | | 5/2012 | |
| KR | 1020130025490 A | | 3/2013 | |
| WO | 03084972 A1 | | 10/2003 | |
| WO | 2005009088 A1 | | 1/2005 | |
| WO | 2005019374 A1 | | 3/2005 | |
| WO | 2005032216 A1 | | 4/2005 | |
| WO | 2005035824 A1 | | 4/2005 | |
| WO | 2005039246 A1 | | 4/2005 | |
| WO | 2005061757 A1 | | 7/2005 | |
| WO | 2005062675 A1 | | 7/2005 | |
| WO | 2005062676 A1 | | 7/2005 | |
| WO | 2005064703 A1 | | 7/2005 | |
| WO | 2005083033 A1 | | 9/2005 | |
| WO | 2005097484 A1 | | 10/2005 | |
| WO | 2005097940 A1 | | 10/2005 | |
| WO | 2005097941 A1 | | 10/2005 | |
| WO | 2005097942 A1 | | 10/2005 | |
| WO | 2005097943 A1 | | 10/2005 | |
| WO | 2005101912 A1 | | 10/2005 | |
| WO | 2005108055 A1 | | 11/2005 | |
| WO | 2005122278 A1 | | 12/2005 | |
| WO | 2005123873 A1 | | 12/2005 | |
| WO | 2006008976 A1 | | 1/2006 | |
| WO | WO2013/032297 A1 | * | 3/2013 | .......... C07D 403/04 |

OTHER PUBLICATIONS

E. Baranoff et al., Influence of Halogen Atoms on a Homologous Series of Bis-Cyclometalated Iridium(III) Complexes, Inorganic Chemistry 2012, 51, pp. 799-811.
R. D. Bowden et al., A New Method for the Synthesis of Aromatic Sulfurpentafluorides and Studies of the Stability of the Sulfurpentafluoride Group in Common Synthetic Transformations, Tetradedron, 56 (2000) pp. 3399-3408.
W. A. Sheppard, Arylsulfur Pentafluorides, J. Am. Chem. Soc. 1962, vol. 84(16), pp. 3064-3072.

* cited by examiner

*Primary Examiner* — Pancham Bakshi
(74) *Attorney, Agent, or Firm* — Cantor Colburn LLP

(57) ABSTRACT

An organometallic compound represented by Formula 1:

$$M(L_1)_{n_1}(L_2)_{n_2} \qquad \text{Formula 1}$$

wherein in Formula 1, M, $L_1$, $L_2$, $n_1$, and $n_2$ are the same as described in the specification.

13 Claims, 2 Drawing Sheets

ORGANOMETALLIC COMPOUND AND ORGANIC LIGHT-EMITTING DEVICE INCLUDING THE SAME

CROSS-REFERENCE TO RELATED APPLICATION

This application claims priority to Korean Patent Application No. 10-2014-0002080, filed on Jan. 7, 2014, and all the benefits accruing therefrom under 35 U.S.C. §119, the content of which is incorporated herein in its entirety by reference.

BACKGROUND

1. Field

The present disclosure relates to an organometallic compound and an organic light-emitting device including the same.

2. Description of the Related Art

Organic light-emitting devices (OLEDs) are self-emission devices that have wide viewing angles, high contrast ratios, and short response times. In addition, OLEDs have excellent brightness, driving voltage, and response speed characteristics, and produce full-color images.

A typical OLED may include an anode, a cathode, and an organic layer that is disposed between the anode and the cathode and includes an emission layer. A hole transport region may be formed between the anode and the emission layer, and an electron transport region may be formed between the emission layer and the cathode. Holes provided from the anode may move toward the emission layer through the hole transport region, and electrons provided from the cathode may move toward the emission layer through the electron transport region. The holes and electrons are recombined in the emission layer to produce excitons. These excitons change from an excited state to a ground state, thereby generating light.

Different types of organic light emitting devices are known. However, there still remains a need in OLEDs having low driving voltage, high efficiency, high brightness, and long lifespan.

SUMMARY

One or more embodiments relate to a novel organometallic compound and an organic light-emitting device (OLED) including the same.

An aspect provides an organometallic compound represented by Formula 1:

$$M(L_1)_{n1}(L_2)_{n2} \qquad \text{Formula 1}$$

wherein in Formula 1,

M is Ir, Pt, Os, Ti, Zr, Hf, Eu, Tb, or Tm;

$L_1$ is a divalent ligand represented by Formula 2; and $L_2$ is a monovalent organic ligand, a divalent organic ligand, or a trivalent organic ligand:

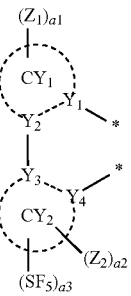

Formula 2 wherein in Formula 2, $Y_1$ to $Y_4$ are each independently C or N;

$Y_1$ and $Y_2$ are connected to each other via a single bond or a double bond, and $Y_3$ and $Y_4$ are connected to each other via a single bond or a double bond;

$CY_1$ and $CY_2$ are each independently a $C_5$-$C_{60}$ carbocyclic group or a $C_2$-$C_{60}$ heterocyclic group, wherein $CY_1$ and $CY_2$ are optionally connected to each other via a single bond or a first linking group;

$Z_1$ and $Z_2$ are each independently a hydrogen, a deuterium, —F, —Cl, —Br, —I, a hydroxyl group, a cyano group, a nitro group, an amino group, an amidino group, a hydrazine group, a hydrazone group, a carboxylic acid and a salt thereof, a sulfonic acid and a salt thereof, a phosphoric acid and a salt thereof, —$SF_5$, a substituted or unsubstituted $C_1$-$C_{60}$ alkyl group, a substituted or unsubstituted $C_2$-$C_{60}$ alkenyl group, a substituted or unsubstituted $C_2$-$C_{60}$ alkynyl group, a substituted or unsubstituted $C_1$-$C_{60}$ alkoxy group, a substituted or unsubstituted $C_3$-$C_{10}$ cycloalkyl group, a substituted or unsubstituted $C_2$-$C_{10}$ heterocycloalkyl group, a substituted or unsubstituted $C_3$-$C_{10}$ cycloalkenyl group, a substituted or unsubstituted $C_2$-$C_{10}$ heterocycloalkenyl group, a substituted or unsubstituted $C_6$-$C_{60}$ aryl group, a substituted or unsubstituted $C_6$-$C_{60}$ aryloxy group, a substituted or unsubstituted $C_6$-$C_{60}$ arylthio group, a substituted or unsubstituted $C_2$-$C_{60}$ heteroaryl group, a substituted or unsubstituted monovalent non-aromatic condensed polycyclic group, a substituted or unsubstituted monovalent non-aromatic condensed heteropolycyclic group, —$N(Q_1)(Q_2)$, —$Si(Q_3)(Q_4)(Q_5)$, or —$B(Q_6)(Q_7)$;

a1, a2, and a3 are each independently selected from an integer of 1 to 5;

n1 is selected from an integer of 1 to 3;

n2 is selected from an integer of 0 to 4;

each of * and *' indicates a binding site with M of Formula 1 above; and wherein at least one substituent of the substituted $C_1$-$C_{60}$ alkyl group, the substituted $C_2$-$C_{60}$ alkenyl group, the substituted $C_2$-$C_{60}$ alkynyl group, the substituted $C_1$-$C_{60}$ alkoxy group, the substituted $C_3$-$C_{10}$ cycloalkyl group, the substituted $C_2$-$C_{10}$ heterocycloalkyl group, the substituted $C_3$-$C_{10}$ cycloalkenyl group, the substituted $C_2$-$C_{10}$ heterocycloalkenyl group, the substituted $C_6$-$C_{60}$ aryl group, the substituted $C_6$-$C_{60}$ aryloxy group, the substituted $C_6$-$C_{60}$ arylthio group, the substituted $C_2$-$C_{60}$ heteroaryl group, the substituted monovalent non-aromatic condensed polycyclic group, and the substituted monovalent non-aromatic condensed heteropolycyclic group is a deuterium, —F, —Cl, —Br, —I, a hydroxyl group, a cyano group, a nitro group, an amino group, an amidino group, a hydrazine group, a hydrazone group, a carboxylic acid and a salt thereof, a sulfonic acid and a salt thereof, a phosphoric acid and a salt thereof, a $C_1$-$C_{60}$ alkyl group, a $C_2$-$C_{60}$ alkenyl group, a $C_2$-$C_{60}$ alkynyl group, or a $C_1$-$C_{60}$ alkoxy group;

a $C_1$-$C_{60}$ alkyl group, a $C_2$-$C_{60}$ alkenyl group, a $C_2$-$C_{60}$ alkynyl group, or a $C_1$-$C_{60}$ alkoxy group, each substituted with at least one group selected from a deuterium, —F, —Cl, —Br, —I, a hydroxyl group, a cyano group, a nitro group, an amino group, an amidino group, a hydrazine group, a hydrazone group, a carboxylic acid and a salt thereof, a sulfonic acid and a salt thereof, a phosphoric acid and a salt thereof, a $C_3$-$C_{10}$ cycloalkyl group, a $C_2$-$C_{10}$ heterocycloalkyl group, a $C_3$-$C_{10}$ cycloalkenyl group, a $C_2$-$C_{10}$ heterocycloalkenyl group, a $C_6$-$C_{60}$ aryl group, a $C_6$-$C_{60}$ aryloxy group, a $C_6$-$C_{60}$ arylthio group, a $C_2$-$C_{60}$ heteroaryl group, a monovalent non-aromatic condensed polycyclic group, a monovalent non-aromatic condensed heteropolycyclic group, —N($Q_{11}$)($Q_{12}$), —Si($Q_{13}$)($Q_{14}$)($Q_{15}$), and —B($Q_{16}$)($Q_{17}$);

a $C_3$-$C_{10}$ cycloalkyl group, a $C_2$-$C_{10}$ heterocycloalkyl group, a $C_3$-$C_{10}$ cycloalkenyl group, a $C_2$-$C_{10}$ a heterocycloalkenyl group, a $C_6$-$C_{60}$ aryl group, a $C_6$-$C_{60}$ aryloxy group, a $C_6$-$C_{60}$ arylthio group, a $C_2$-$C_{60}$ heteroaryl group, a monovalent non-aromatic condensed polycyclic group, or a monovalent non-aromatic condensed heteropolycyclic group;

a $C_3$-$C_{10}$ cycloalkyl group, a $C_2$-$C_{10}$ heterocycloalkyl group, a $C_3$-$C_{10}$ cycloalkenyl group, a $C_2$-$C_{10}$ heterocycloalkenyl group, a $C_6$-$C_{60}$ aryl group, a $C_6$-$C_{60}$ aryloxy group, a $C_6$-$C_{60}$ arylthio group, a $C_2$-$C_{60}$ heteroaryl group, a monovalent non-aromatic condensed polycyclic group, or a monovalent non-aromatic condensed heteropolycyclic group, each substituted with at least one group selected from a deuterium, —F, —Cl, —Br, —I, a hydroxyl group, a cyano group, a nitro group, an amino group, an amidino group, a hydrazine group, a hydrazone group, a carboxylic acid and a salt thereof, a sulfonic acid and a salt thereof, a phosphoric acid and a salt thereof, a $C_1$-$C_{60}$ alkyl group, a $C_2$-$C_{60}$ alkenyl group, a $C_2$-$C_{60}$ alkynyl group, a $C_1$-$C_{60}$ alkoxy group, a $C_3$-$C_{10}$ cycloalkyl group, a $C_2$-$C_{10}$ heterocycloalkyl group, a $C_3$-$C_{10}$ cycloalkenyl group, a $C_2$-$C_{10}$ heterocycloalkenyl group, a $C_6$-$C_{60}$ aryl group, a $C_6$-$C_{60}$ aryloxy group, a $C_6$-$C_{60}$ arylthio group, a $C_2$-$C_{60}$ heteroaryl group, a monovalent non-aromatic condensed polycyclic group, a monovalent non-aromatic condensed heteropolycyclic group, —N($Q_{21}$)($Q_{22}$), —Si($Q_{23}$)($Q_{24}$)($Q_{25}$), and —B($Q_{26}$)($Q_{27}$); or —N($Q_{31}$)($Q_{32}$), —Si($Q_{33}$)($Q_{34}$)($Q_{35}$), or —B($Q_{36}$)($Q_{37}$); and wherein $Q_1$ to $Q_7$, $Q_{11}$ to $Q_{17}$, $Q_{21}$ to $Q_{27}$, and $Q_{31}$ to $Q_{37}$ are each independently a hydrogen, a deuterium, —F, —Cl, —Br, —I, a hydroxyl group, a cyano group, a nitro group, an amino group, an amidino group, a hydrazine group, a hydrazone group, a carboxylic acid and a salt thereof, a sulfonic acid and a salt thereof, a phosphoric acid and a salt thereof, a $C_1$-$C_{60}$ alkyl group, a $C_2$-$C_{60}$ alkenyl group, a $C_2$-$C_{60}$ alkynyl group, a $C_1$-$C_{60}$ alkoxy group, a $C_3$-$C_{10}$ cycloalkyl group, a $C_2$-$C_{10}$ heterocycloalkyl group, a $C_3$-$C_{10}$ cycloalkenyl group, a $C_2$-$C_{10}$ heterocycloalkenyl group, a $C_6$-$C_{60}$ aryl group, a $C_6$-$C_{60}$ aryloxy group, a $C_6$-$C_{60}$ arylthio group, a $C_2$-$C_{60}$ heteroaryl group, a monovalent non-aromatic condensed polycyclic group, or a monovalent non-aromatic condensed heteropolycyclic group, provided that compounds:

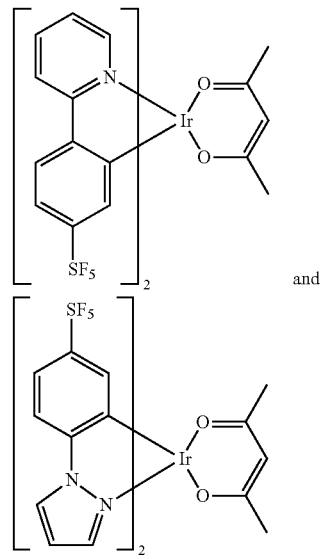

and are excluded.

Another aspect provides an OLED including: a first electrode; a second electrode; and an organic layer disposed between the first electrode and the second electrode, wherein the organic layer comprises an emission layer, and wherein the organic layer includes at least one organometallic compound of Formula 1 above.

The organometallic compound may be included in the emission layer, and the organometallic compound included therein may act as a dopant. The emission layer may further include a host.

BRIEF DESCRIPTION OF THE DRAWINGS

These and/or other aspects will become apparent and more readily appreciated from the following description of the embodiments, taken in conjunction with the accompanying drawings in which.

DETAILED DESCRIPTION

Figure 1:
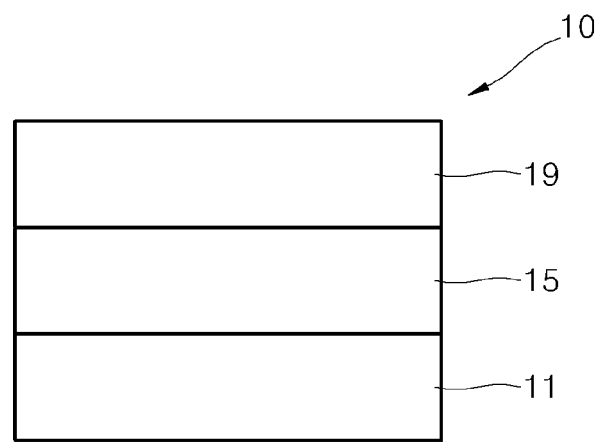
FIG. 1 is a schematic view of an organic light-emitting device according to an embodiment.

Reference will now be made in detail to embodiments, examples of which are illustrated in the accompanying drawings, wherein like reference numerals refer to like elements throughout. In this regard, the present embodiments may have different forms and should not be construed as being limited to the descriptions set forth herein. Accordingly, the embodiments are merely described below, by referring to the figures, to explain aspects of the present description. As used herein, the term "and/or" includes any and all combinations of one or more of the associated listed items. Expressions such as "at least one of," when preceding a list of elements, modify the entire list of elements and do not modify the individual elements of the list.

It will be understood that when an element is referred to as being "on" another element, it can be directly in contact with the other element or intervening elements may be present therebetween. In contrast, when an element is referred to as being "directly on" another element, there are no intervening elements present.

It will be understood that, although the terms first, second, third etc. may be used herein to describe various elements, components, regions, layers, and/or sections, these elements, components, regions, layers, and/or sections should not be limited by these terms. These terms are only used to distinguish one element, component, region, layer, or section from another element, component, region, layer, or section. Thus, a first element, component, region, layer, or section discussed below could be termed a second element, component, region, layer, or section without departing from the teachings of the present embodiments.

The terminology used herein is for the purpose of describing particular embodiments only and is not intended to be limiting. As used herein, the singular forms "a," "an," and "the" are intended to include the plural forms as well, unless the context clearly indicates otherwise.

The term "or" means "and/or." It will be further understood that the terms "comprises" and/or "comprising," or "includes" and/or "including" when used in this specification, specify the presence of stated features, regions, integers, steps, operations, elements, and/or components, but do not preclude the presence or addition of one or more other features, regions, integers, steps, operations, elements, components, and/or groups thereof.

Unless otherwise defined, all terms (including technical and scientific terms) used herein have the same meaning as commonly understood by one of ordinary skill in the art to which this general inventive concept belongs. It will be further understood that terms, such as those defined in commonly used dictionaries, should be interpreted as having a meaning that is consistent with their meaning in the context of the relevant art and the present disclosure, and will not be interpreted in an idealized or overly formal sense unless expressly so defined herein.

Exemplary embodiments are described herein with reference to cross section illustrations that are schematic illustrations of idealized embodiments. As such, variations from the shapes of the illustrations as a result, for example, of manufacturing techniques and/or tolerances, are to be expected. Thus, embodiments described herein should not be construed as limited to the particular shapes of regions as illustrated herein but are to include deviations in shapes that result, for example, from manufacturing. For example, a region illustrated or described as flat may, typically, have rough and/or nonlinear features. Moreover, sharp angles that are illustrated may be rounded. Thus, the regions illustrated in the figures are schematic in nature and their shapes are not intended to illustrate the precise shape of a region and are not intended to limit the scope of the present claims.

An organometallic compound according to an embodiment is represented by Formula 1 below:

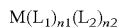

Formula 1 wherein in Formula 1, $L_1$ may be a divalent ligand represented by Formula 2 below, and $L_2$ may be a monovalent organic ligand, a divalent organic ligand, or a trivalent organic ligand:

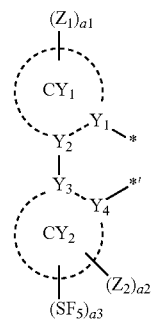

Formula 2 wherein in Formula 2, each of * and *' may indicate a binding site to M of Formula 1.

In Formula 1, M may be iridium (Ir), platinum (Pt), osmium (Os), titanium (Ti), zirconium (Zr), hafnium (Hf), europium (Eu), terbium (Tb), or thulium (Tm).

For example, M may be Ir or Pt.

In Formula 2, $Y_1$ to $Y_4$ may be each independently carbon (C) or nitrogen (N).

In Formula 2, $Y_1$ and $Y_2$ may be connected to each other via a single bond or a double bond, and $Y_3$ and $Y_4$ may be connected to each other via a single bond or a double bond.

For example, in Formula 2, $Y_1$ may be N and $Y_4$ may be C.

In some embodiments, $Y_3$ of Formula 2 may be C, but is not limited thereto.

In Formula 2, $CY_1$ and $CY_2$ may be each independently a $C_5$-$C_{60}$ carbocyclic group or a $C_2$-$C_{60}$ heterocyclic group.

For example, in Formula 2, $CY_1$ and $CY_2$ may be each independently benzene, naphthalene, fluorenene, spiro-fluorenene, indene, pyrrole, thiophene, furan, imidazole, pyrazole, thiazole, isothiazole, oxazole, isooxazole, pyridine, pyrazine, pyrimidine, pyridazine, quinoline, isoquinoline, benzoquinoline, quinoxaline, quinazoline, carbazole, benzoimidazole, benzofuran, benzothiophene, isobenzothiophene, benzooxazole, isobenzooxazole, triazole, tetrazole, oxadiazole, triazine, dibenzofuran, or dibenzothiophene.

In some other embodiments, $CY_1$ of Formula 2 may be pyridine, triazole, imidazole, or pyrazole, and $CY_2$ of Formula 2 may be benzene or pyridine, but are not limited thereto.

In Formula 2, $CY_1$ and $CY_2$ may be optionally connected to each other via a single bond or a first linking group.

The first linking group may be represented by Formula 6 below:

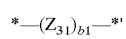

Formula 6 wherein in Formula 6, $Z_{31}$ may be *—O—*', *—S—*', *—N($Q_{41}$)-*', *—C($Q_{42}$)($Q_{43}$)-*, *—C($Q_{44}$)=C($Q_{45}$)-*', or

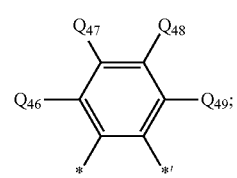

$Q_{41}$ to $Q_{49}$ may be each independently a hydrogen, a deuterium, —F, —Cl, —Br, —I, a hydroxyl group, a cyano group, a nitro group, an amino group, an amidino group, a hydrazine group, a hydrazone group, a carboxylic acid and a salt thereof, a sulfonic acid and a salt thereof, a phosphoric acid and a salt thereof, a $C_1$-$C_{60}$ alkyl group, a $C_2$-$C_{60}$ alkenyl group, a $C_2$-$C_{60}$ alkynyl group, or a $C_1$-$C_{60}$ alkoxy group;

a $C_1$-$C_{60}$ alkyl group, a $C_2$-$C_{60}$ alkenyl group, a $C_2$-$C_{60}$ alkynyl group, or $C_1$-$C_{60}$ alkoxy group, each substituted with at least one group selected from a deuterium, —F, —Cl, —Br, —I, a hydroxyl group, a cyano group, a nitro group, an amino group, an amidino group, a hydrazine group, a hydrazone group, a carboxylic acid and a salt thereof, a sulfonic acid and a salt thereof, a phosphoric acid and a salt thereof, a $C_3$-$C_{10}$ cycloalkyl group, a $C_2$-$C_{10}$ heterocycloalkyl group, a $C_3$-$C_{10}$ cycloalkenyl group, a $C_2$-$C_{10}$ heterocycloalkenyl group, a $C_6$-$C_{60}$ aryl group, a $C_6$-$C_{60}$ aryloxy group, a $C_6$-$C_{60}$ arylthio group, a $C_2$-$C_{60}$ heteroaryl group, a monovalent non-aromatic condensed polycyclic group, and a monovalent non-aromatic condensed heteropolycyclic group;

a $C_3$-$C_{10}$ cycloalkyl group, a $C_2$-$C_{10}$ heterocycloalkyl group, a $C_3$-$C_{10}$ cycloalkenyl group, a $C_2$-$C_{10}$ heterocycloalkenyl group, a $C_6$-$C_{60}$ aryl group, a $C_6$-$C_{60}$ aryloxy group, a $C_6$-$C_{60}$ arylthio group, a $C_2$-$C_{60}$ heteroaryl group, a monovalent non-aromatic condensed polycyclic group, or a monovalent non-aromatic condensed heteropolycyclic group; or a $C_3$-$C_{10}$ cycloalkyl group, a $C_2$-$C_{10}$ heterocycloalkyl group, a $C_3$-$C_{10}$ cycloalkenyl group, a $C_2$-$C_{10}$ heterocycloalkenyl group, a $C_6$-$C_{60}$ aryl group, a $C_6$-$C_{60}$ aryloxy group, a $C_6$-$C_{60}$ arylthio group, a $C_2$-$C_{60}$ heteroaryl group, a monovalent non-aromatic condensed polycyclic group, or a monovalent non-aromatic condensed heteropolycyclic group, each substituted with at least one group selected from a deuterium, —F, —Cl, —Br, —I, a hydroxyl group, a cyano group, a nitro group, an amino group, an amidino group, a hydrazine group, a hydrazone group, a carboxylic acid and a salt thereof, a sulfonic acid and a salt thereof, a phosphoric acid and a salt thereof, a $C_1$-$C_{60}$ alkyl group, a $C_2$-$C_{60}$ alkenyl group, a $C_2$-$C_{60}$ alkynyl group, a $C_1$-$C_{60}$ alkoxy group, a $C_3$-$C_{10}$ cycloalkyl group, a $C_2$-$C_{10}$ heterocycloalkyl group, a $C_3$-$C_{10}$ cycloalkenyl group, a $C_2$-$C_{10}$ heterocycloalkenyl group, a $C_6$-$C_{60}$ aryl group, a $C_6$-$C_{60}$ aryloxy group, a $C_6$-$C_{60}$ arylthio group, a $C_2$-$C_{60}$ heteroaryl group, a monovalent non-aromatic condensed polycyclic group, and a monovalent non-aromatic condensed heteropolycyclic group; and wherein in Formula 6, b1 may be an integer of 1 to 10, and when b1 is 2 or more, groups $Z_{31}$ may be identical or different.

For example, in Formula 6, $Q_{41}$ to $Q_{49}$ may be each independently a hydrogen, a deuterium, —F, —Cl, —Br, —I, a hydroxyl group, a cyano group, a nitro group, an amino group, an amidino group, a hydrazine group, a hydrazone group, a carboxylic acid and a salt thereof, a sulfonic acid and a salt thereof, a phosphoric acid and a salt thereof, a $C_1$-$C_{20}$ alkyl group, or a $C_1$-$C_{20}$ alkoxy group;

a $C_1$-$C_{20}$ alkyl group or a $C_1$-$C_{20}$ alkoxy group, each substituted with at least one group selected from a deuterium, —F, —Cl, —Br, —I, a hydroxyl group, a cyano group, a nitro group, an amino group, an amidino group, a hydrazine group, a hydrazone group, a carboxylic acid and a salt thereof, a sulfonic acid and a salt thereof, a phosphoric acid and a salt thereof, a phenyl group, a naphthyl group, a pyridinyl group, and a pyrimidinyl group; or a phenyl group, a naphthyl group, a pyridinyl group, or a pyrimidinyl group; but are not limited thereto.

For example, in Formula 2, $CY_1$ and $CY_2$ may be connected to each other via a single bond or a first linking group, wherein the first linking group may be represented by *—$C(Q_{44})$=$C(Q_{45})$-*' or

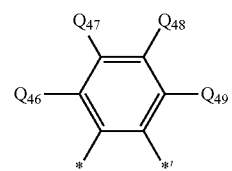

(wherein b1 in Formula 6 is 1), wherein $Q_{44}$ to $Q_{49}$ may be each independently a hydrogen, a $C_1$-$C_{10}$ alkyl group, or a $C_1$-$C_{10}$ alkoxy group, but are not limited thereto.

In Formula 1, $L_1$ may be a compound represented by one of Formulae 2A to 2E below, but is not limited thereto:

Formula 2A

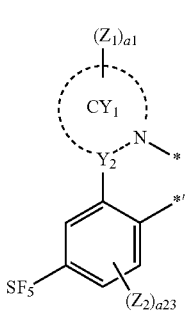

Formula 2B

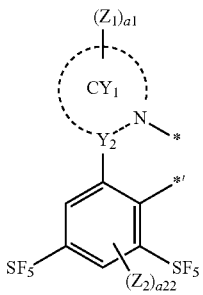

Formula 2C

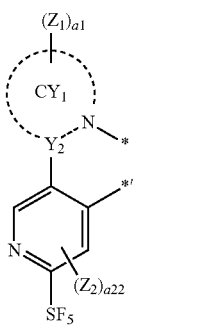

-continued

Formula 2D

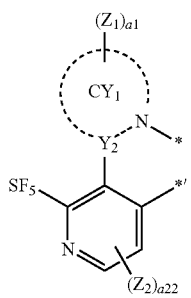

Formula 2E

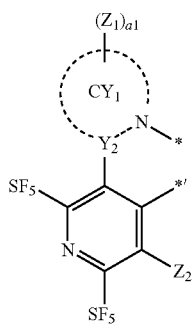

In Formulae 2A to 2E, $CY_1$, $Y_2$, $Z_1$, $Z_2$, a1, * and *' may be understood by referring to the corresponding description provided herein.

In Formulae 2A to 2E, a23 may be selected from an integer of 1 to 3, and a22 may be 1 or 2.

In Formulae 2, $Z_1$ and $Z_2$ may be each independently a hydrogen, a deuterium, —F, —Cl, —Br, —I, a hydroxyl group, a cyano group, a nitro group, an amino group, an amidino group, a hydrazine group, a hydrazone group, a carboxylic acid and a salt thereof, a sulfonic acid and a salt thereof, a phosphoric acid and a salt thereof, —$SF_5$, a substituted or unsubstituted $C_1$-$C_{60}$ alkyl group, a substituted or unsubstituted $C_2$-$C_{60}$ alkenyl group, a substituted or unsubstituted $C_2$-$C_{60}$ alkynyl group, a substituted or unsubstituted $C_1$-$C_{60}$ alkoxy group, a substituted or unsubstituted $C_3$-$C_{10}$ cycloalkyl group, a substituted or unsubstituted $C_2$-$C_{10}$ heterocycloalkyl group, a substituted or unsubstituted $C_3$-$C_{10}$ cycloalkenyl group, a substituted or unsubstituted $C_2$-$C_{10}$ heterocycloalkenyl group, a substituted or unsubstituted $C_6$-$C_{60}$ aryl group, a substituted or unsubstituted $C_6$-$C_{60}$ aryloxy group, a substituted or unsubstituted $C_6$-$C_{60}$ arylthio group, a substituted or unsubstituted $C_2$-$C_{60}$ heteroaryl group, a substituted or unsubstituted monovalent non-aromatic condensed polycyclic group, a substituted or unsubstituted monovalent non-aromatic condensed heteropolycyclic group, —$N(Q_1)(Q_2)$, —$Si(Q_3)(Q_4)(Q_5)$, or —$B(Q_6)(Q_7)$.

For example, in Formula 2, $Z_1$ and $Z_2$ may be each independently a hydrogen, a deuterium, —F, —Cl, —Br, —I, a hydroxyl group, a cyano group, a nitro group, an amino group, an amidino group, a hydrazine group, a hydrazone group, a carboxylic acid and a salt thereof, a sulfonic acid and a salt thereof, a phosphoric acid and a salt thereof, —$SF_5$, a $C_1$-$C_{20}$ alkyl group, or a $C_1$-$C_{20}$ alkoxy group;

a $C_1$-$C_{20}$ alkyl group or a $C_1$-$C_{60}$ alkoxy group, each substituted by at least one group selected from a deuterium, —F, —Cl, —Br, —I, a hydroxyl group, a cyano group, a nitro group, an amino group, an amidino group, a hydrazine group, a hydrazone group, a carboxylic acid and a salt thereof, a sulfonic acid and a salt thereof, a phosphoric acid and a salt thereof, a phenyl group, a naphthyl group, a pyridinyl group, and a pyrimidinyl group;

a phenyl group, a pentalenyl group, an indenyl group, a naphthyl group, an azulenyl group, a heptalenyl group, an indacenyl group, an acenaphthyl group, a fluorenyl group, a spiro-fluorenyl group, a benzofluorenyl group, a dibenzofluorenyl group, a phenalenyl group, a phenanthrenyl group, an anthracenyl group, a fluoranthrenyl group, a triphenylenyl group, a pyrenyl group, a chrysenyl group, a naphthacenyl group, a picenyl group, a perylenyl group, a pentaphenyl group, a hexacenyl group, a pentacenyl group, a rubicenyl group, a coronenyl group, an ovalenyl group, a pyrrolyl group, a thiophenyl group, a furanyl group, an imidazolyl group, a pyrazolyl group, a thiazolyl group, an isothiazolyl group, an oxazolyl group, an isooxazolyl group, a pyridinyl group, a pyrazinyl group, a pyrimidinyl group, a pyridazinyl group, an isoindolyl group, an indolyl group, an indazolyl group, a purinyl group, a quinolinyl group, an isoquinolinyl group, a benzoquinolinyl group, a phthalazinyl group, a naphthyridinyl group, a quinoxalinyl group, a quinazolinyl group, a cinnolinyl group, a carbazolyl group, a phenanthridinyl group, an acridinyl group, a phenanthrolinyl group, a phenazinyl group, a benzoimidazolyl group, a benzofuranyl group, a benzothiophenyl group, an isobenzothiazolyl group, a benzooxazolyl group, an isobenzooxazolyl group, a triazolyl group, a tetrazolyl group, an oxadiazolyl group, a triazinyl group, a dibenzofuranyl group, a dibenzothiophenyl group, a benzocarbazolyl group, a dibenzocarbazolyl group, an imidazopyridinyl group, or an imidazopyrimidinyl group;

a phenyl group, a pentalenyl group, an indenyl group, a naphthyl group, an azulenyl group, a heptalenyl group, an indacenyl group, an acenaphthyl group, a fluorenyl group, a spiro-fluorenyl group, a benzofluorenyl group, a dibenzofluorenyl group, a phenalenyl group, a phenanthrenyl group, an anthracenyl group, a fluoranthrenyl group, a triphenylenyl group, a pyrenyl group, a chrysenyl group, a naphthacenyl group, a picenyl group, a perylenyl group, a pentaphenyl group, a hexacenyl group, a pentacenyl group, a rubicenyl group, a coronenyl group, an ovalenyl group, a pyrrolyl group, a thiophenyl group, a furanyl group, an imidazolyl group, a pyrazolyl group, a thiazolyl group, an isothiazolyl group, an oxazolyl group, an isooxazolyl group, a pyridinyl group, a pyrazinyl group, a pyrimidinyl group, a pyridazinyl group, an isoindolyl group, an indolyl group, an indazolyl group, a purinyl group, a quinolinyl group, an isoquinolinyl group, a benzoquinolinyl group, a phthalazinyl group, a naphthyridinyl group, a quinoxalinyl group, a quinazolinyl group, a cinnolinyl group, a carbazolyl group, a phenanthridinyl group, an acridinyl group, a phenanthrolinyl group, a phenazinyl group, a benzoimidazolyl group, a benzofuranyl group, a benzothiophenyl group, an isobenzothiazolyl group, a benzooxazolyl group, an isobenzooxazolyl group, a triazolyl group, a tetrazolyl group, an oxadiazolyl group, a triazinyl group, a dibenzofuranyl group, a dibenzothiophenyl group, a benzocarbazolyl group, a dibenzocarbazolyl group, an imidazopyridinyl group, or an imidazopyrimidinyl group, each substituted with at least one group selected from a deuterium, —F, —Cl, —Br, —I, a hydroxyl group, a cyano group, a nitro group, an amino group, an amidino group, a hydrazine group, a hydrazone group, a carboxylic acid and a salt thereof, a sulfonic acid and a salt thereof, a phosphoric acid and a salt thereof, a $C_1$-$C_{20}$ alkyl group, a $C_1$-$C_{20}$ alkoxy group, a phenyl group, a pentalenyl group, an indenyl group, a naphthyl group, an azulenyl group, a heptalenyl group, an indacenyl group, an acenaphthyl group, a fluorenyl group, a spiro-fluorenyl group, a benzofluorenyl group, a dibenzofluorenyl group, a phenalenyl group, a phenanthrenyl group, an anthracenyl group, a fluoranthrenyl group, a triphenylenyl group, a pyrenyl group, a chrysenyl group, a naphthacenyl group, a picenyl group, a perylenyl group, a pentaphenyl group, a hexacenyl group, a pentacenyl group, a rubicenyl group, a coronenyl group, an ovalenyl group, a pyrrolyl group, a thiophenyl group, a furanyl group, an imidazolyl group, a pyrazolyl group, a thiazolyl group, an isothiazolyl group, an oxazolyl group, an isooxazolyl group, a pyridinyl group, a pyrazinyl group, a pyrimidinyl group, a pyridazinyl group, an isoindolyl group, an indolyl group, an indazolyl group, a purinyl group, a quinolinyl group, an isoquinolinyl group, a benzoquinolinyl group, a phthalazinyl group, a naphthyridinyl group, a quinoxalinyl group, a quinazolinyl group, a cinnolinyl group, a carbazolyl group, a phenanthridinyl group, an acridinyl group, a phenanthrolinyl group, a phenazinyl group, a benzoimidazolyl group, a benzofuranyl group, a benzothiophenyl group, an isobenzothiazolyl group, a benzooxazolyl group, an isobenzooxazolyl group, a triazolyl group, a tetrazolyl group, an oxadiazolyl group, a triazinyl group, a dibenzofuranyl group, a dibenzothiophenyl group, a benzocarbazolyl group, a dibenzocarbazolyl group, an imidazopyridinyl group, and an imidazopyrimidinyl group; or —Si($Q_3$)($Q_4$)($Q_5$); and wherein $Q_3$ to $Q_5$ may be each independently a hydrogen, a $C_1$-$C_{20}$ alkyl group, a $C_1$-$C_{20}$ alkoxy group, a phenyl group, a naphthyl group, an anthracenyl group, a pyrenyl group, a phenanthrenyl group, a fluorenyl group, a chrysenyl group, a carbazolyl group, a benzocarbazolyl group, a dibenzocarbazolyl group, a dibenzofuranyl group, a dibenzocarbazolyl group, a pyridinyl group, a pyrimidinyl group, a triazinyl group, a quinolinyl group, an isoquinolinyl group, a quinazolinyl group, or a quinoxalinyl group.

In some other embodiments, in Formula 2, $Z_1$ and $Z_2$ may be each independently a hydrogen, a deuterium, —F, —Cl, —Br, —I, a hydroxyl group, a cyano group, a nitro group, an amino group, an amidino group, a hydrazine group, a hydrazone group, a carboxylic acid and a salt thereof, a sulfonic acid and a salt thereof, a phosphoric acid and a salt thereof, —$SF_5$, a $C_1$-$C_{20}$ alkyl group, or a $C_1$-$C_{20}$ alkoxy group;

a $C_1$-$C_{20}$ alkyl group or a $C_1$-$C_{20}$ alkoxy group, each substituted with at least one group selected from a deuterium, —F, —Cl, —Br, —I, a hydroxyl group, a cyano group, a nitro group, an amino group, an amidino group, a hydrazine group, a hydrazone group, a carboxylic acid and a salt thereof, a sulfonic acid and a salt thereof, a phosphoric acid and a salt thereof, a phenyl group, a naphthyl group, a pyridinyl group, and a pyrimidinyl group;

a phenyl group, a naphthyl group, a fluorenyl group, a phenanthrenyl group, an anthracenyl group, a fluoranthrenyl group, a triphenylenyl group, a pyrenyl group, a chrysenyl group, a pyrrolyl group, a thiophenyl group, a furanyl group, an imidazolyl group, a pyrazolyl group, a thiazolyl group, an isothiazolyl group, an oxazolyl group, an isooxazolyl group, a pyridinyl group, a pyrazinyl group, a pyrimidinyl group, a pyridazinyl group, an isoindolyl group, an indolyl group, an indazolyl group, a purinyl group, a quinolinyl group, an isoquinolinyl group, a benzoquinolinyl group, a quinoxalinyl group, a quinazolinyl group, a cinnolinyl group, a carbazolyl group, a phenanthrolinyl group, a benzoimidazolyl group, a benzofuranyl group, a benzothiophenyl group, an isobenzothiazolyl group, a benzooxazolyl group, an isobenzooxazolyl group, a triazolyl group, a tetrazolyl group, an oxadiazolyl group, a triazinyl group, a dibenzofuranyl group, a dibenzothiophenyl group, a benzocarbazolyl group, a dibenzocarbazolyl group, an imidazopyridinyl group, or an imidazopyrimidinyl group; and a phenyl group, a naphthyl group, a fluorenyl group, a phenanthrenyl group, an anthracenyl group, a fluoranthrenyl group, a triphenylenyl group, a pyrenyl group, a chrysenyl group, a pyrrolyl group, a thiophenyl group, a furanyl group, an imidazolyl group, a pyrazolyl group, a thiazolyl group, an isothiazolyl group, an oxazolyl group, an isooxazolyl group, a pyridinyl group, a pyrazinyl group, a pyrimidinyl group, a pyridazinyl group, an isoindolyl group, an indolyl group, an indazolyl group, a purinyl group, a quinolinyl group, an isoquinolinyl group, a benzoquinolinyl group, a quinoxalinyl group, a quinazolinyl group, a cinnolinyl group, a carbazolyl group, a phenanthrolinyl group, a benzoimidazolyl group, a benzofuranyl group, a benzothiophenyl group, an isobenzothiazolyl group, a benzooxazolyl group, an isobenzooxazolyl group, a triazolyl group, a tetrazolyl group, an oxadiazolyl group, a triazinyl group, a dibenzofuranyl group, a dibenzothiophenyl group, a benzocarbazolyl group, a dibenzocarbazolyl group, an imidazopyridinyl group, or an imidazopyrimidinyl group, each substituted with at least one group selected from a deuterium, —F, —Cl, —Br, —I, a hydroxyl group, a cyano group, a nitro group, an amino group, an amidino group, a hydrazine group, a hydrazone group, a carboxylic acid and a salt thereof, a sulfonic acid and a salt thereof, a phosphoric acid and a salt thereof, a $C_1$-$C_{20}$ alkyl group, a $C_1$-$C_{20}$ alkoxy group, a phenyl group, a naphthyl group, a fluorenyl group, a phenanthrenyl group, an anthracenyl group, a fluoranthrenyl group, a triphenylenyl group, a pyrenyl group, a chrysenyl group, a pyrrolyl group, a thiophenyl group, a furanyl group, an imidazolyl group, a pyrazolyl group, a thiazolyl group, an isothiazolyl group, an oxazolyl group, an isooxazolyl group, a pyridinyl group, a pyrazinyl group, a pyrimidinyl group, a pyridazinyl group, an isoindolyl group, an indolyl group, an indazolyl group, a purinyl group, a quinolinyl group, an isoquinolinyl group, a benzoquinolinyl group, a quinoxalinyl group, a quinazolinyl group, a cinnolinyl group, a carbazolyl group, a phenanthrolinyl group, a benzoimidazolyl group, a benzofuranyl group, a benzothiophenyl group, an isobenzothiazolyl group, a benzooxazolyl group, an isobenzooxazolyl group, a triazolyl group, a tetrazolyl group, an oxadiazolyl group, a triazinyl group, a dibenzofuranyl group, a dibenzothiophenyl group, a benzocarbazolyl group, a dibenzocarbazolyl group, an imidazopyridinyl group, and an imidazopyrimidinyl group; but are not limited thereto.

In some other embodiments, in Formula 2, $Z_1$ and $Z_2$ may be each independently a hydrogen, —F, a cyano group, a nitro group, —$SF_5$, a methyl group, an ethyl group, a propyl group, an n-butyl group, an isobutyl group, a sec-butyl group, a tert-butyl group, an n-pentyl group, an isopentyl group, a sec-pentyl group, a tert-pentyl group, an n-hexyl group, an isohexyl group, a sec-hexyl group, a tert-hexyl group, an n-heptyl group, an isoheptyl group, a sec-heptyl group, a tert-heptyl group, an n-octyl group, an isooctyl group, a sec-octyl group, a tert-octyl group, an n-nonyl group, an isononyl group, a sec-nonyl group, a tert-nonyl group, an n-decanyl group, an isodecanyl group, a sec-decanyl group, a tert-decanyl group, a methoxy group, an ethoxy group, a propoxy group, a butoxy group, a pentoxy group, a phenyl group, a naphthyl group, a pyridinyl group, a pyrimidinyl group, or a triazinyl group; or a methyl group, an ethyl group, a propyl group, an n-butyl group, an isobutyl group, a sec-butyl group, a tert-butyl group, an n-pentyl group, an isopentyl group, a sec-pentyl group, a tert-pentyl group, an n-hexyl group, an isohexyl group, a sec-hexyl group, a tert-hexyl group, an n-heptyl group, an isoheptyl group, a sec-heptyl group, a tert-heptyl group, an n-octyl group, an isooctyl group, a sec-octyl group, a tert-octyl group, an n-nonyl group, an isononyl group, a sec-nonyl group, a tert-nonyl group, an n-decanyl group, an isodecanyl group, a sec-decanyl group, a tert-decanyl group, a methoxy group, an ethoxy group, a propoxy group, a butoxy group, a pentoxy group, a phenyl group, a naphthyl group, a pyridinyl group, a pyrimidinyl group, or a triazinyl group (e.g., —CF$_3$), each substituted with at least one group selected from —F, a cyano group, and a nitro group; but are not limited thereto.

In Formula 2, a1 denotes the number of $Z_1$ and may be selected from an integer of 1 to 5. For example, a1 may be selected from an integer of 1 to 3, but is not limited thereto. For example, a1 may be 1. When a1 is 2 or more, groups $Z_1$ may be identical or different. In Formula 2, a2 denotes the number of $Z_2$ and may be understood by referring to the description provided herein in connection with a1.

In Formula 1, a3 denotes the number of —SF$_5$ and may be selected from an integer of 1 to 5. For example, a3 may be 1, 2, or 3, or may be 1 or 2. Since a3 is not 0, CY$_2$ of the organometallic compound of Formula 1 may have at least one —SF$_5$ as a substituent.

According to an embodiment, in Formula 1, $L_1$ may be a compound represented by one of Formulae 2-1 to 2-130 below:

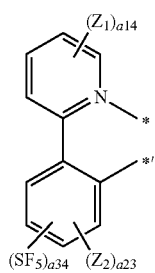

Formula 2-1

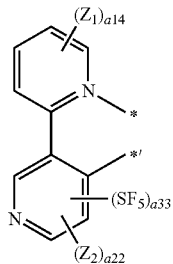

Formula 2-2

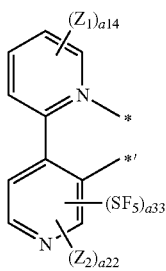

Formula 2-3

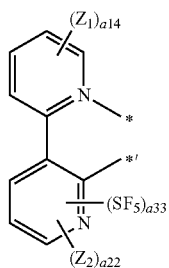

Formula 2-4

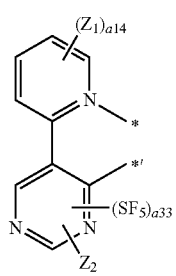

Formula 2-5

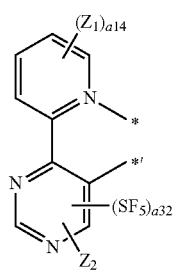

Formula 2-6

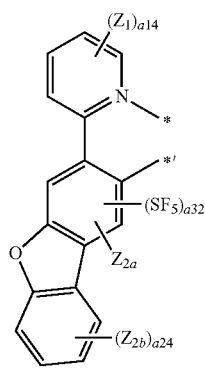

Formula 2-7

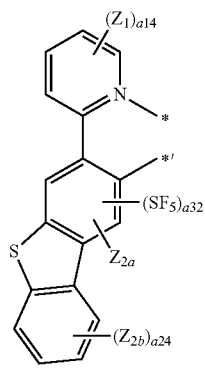

Formula 2-8

-continued
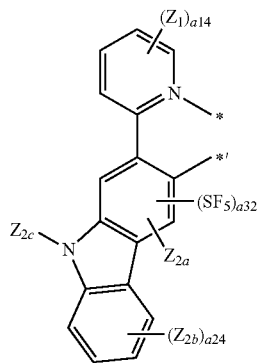
Formula 2-9
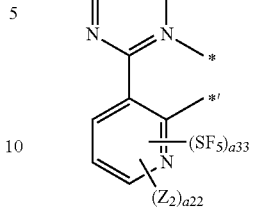
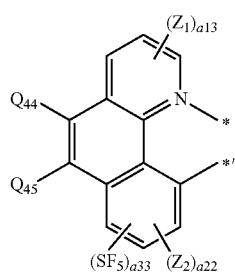
Formula 2-10
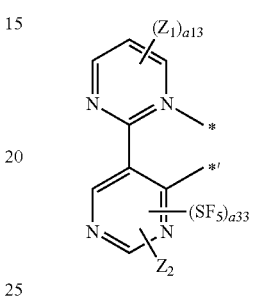
Formula 2-14
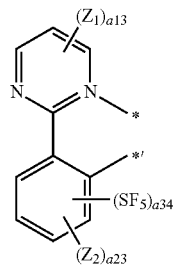
Formula 2-11
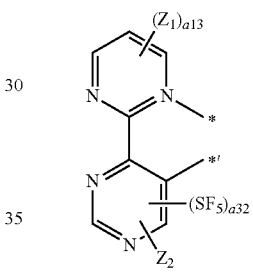
Formula 2-15
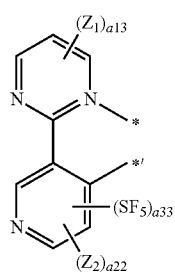
Formula 2-12
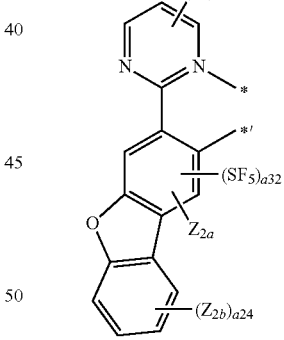
Formula 2-16
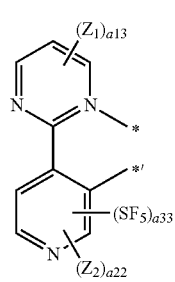
Formula 2-13
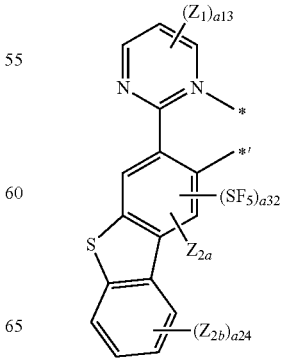
Formula 2-17
Formula 2-18

Formula 2-19
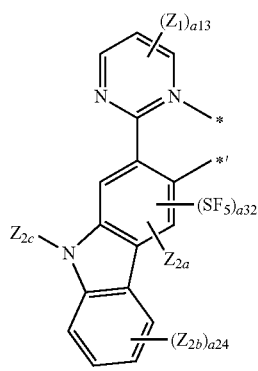
Formula 2-20
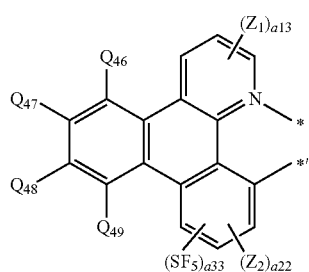
Formula 2-21
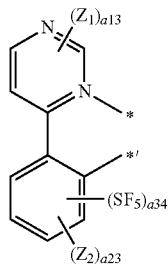
Formula 2-22
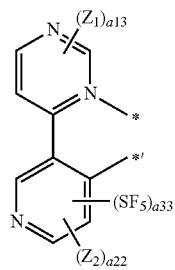
Formula 2-23
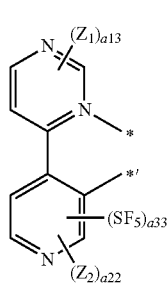
Formula 2-24
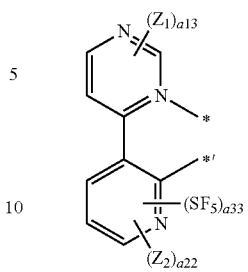
Formula 2-25
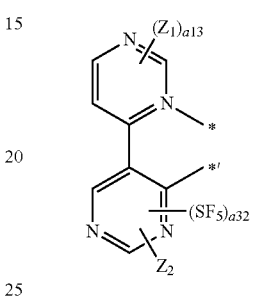
Formula 2-26
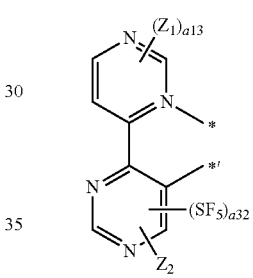
Formula 2-27
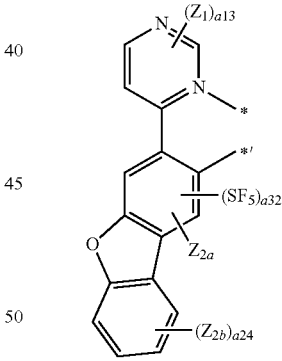
Formula 2-28
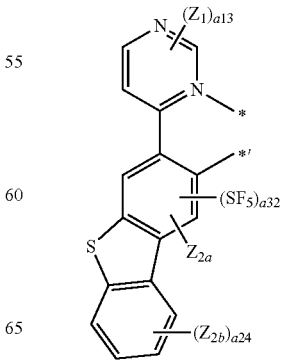

Formula 2-29
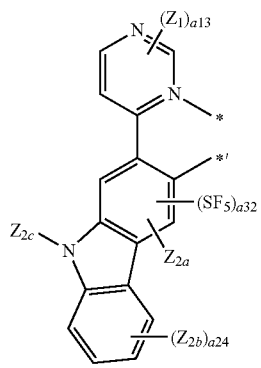
Formula 2-30
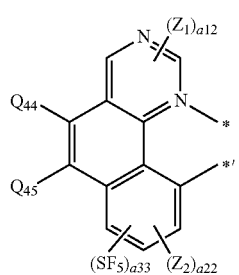
Formula 2-31
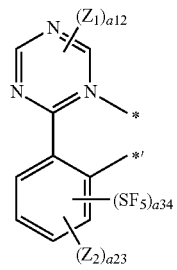
Formula 2-32
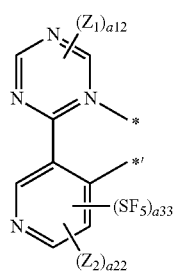
Formula 2-33
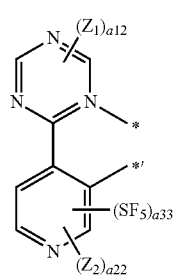
Formula 2-34
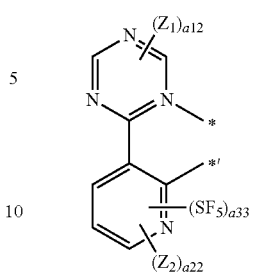
Formula 2-35
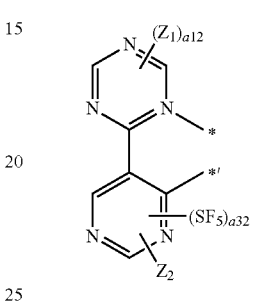
Formula 2-36
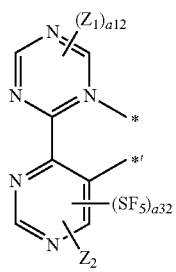
Formula 2-37
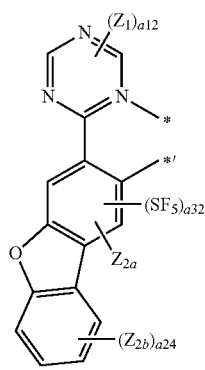
Formula 2-38
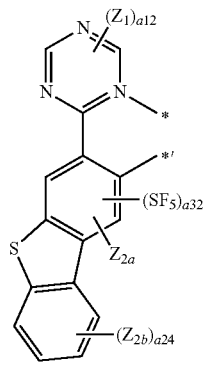

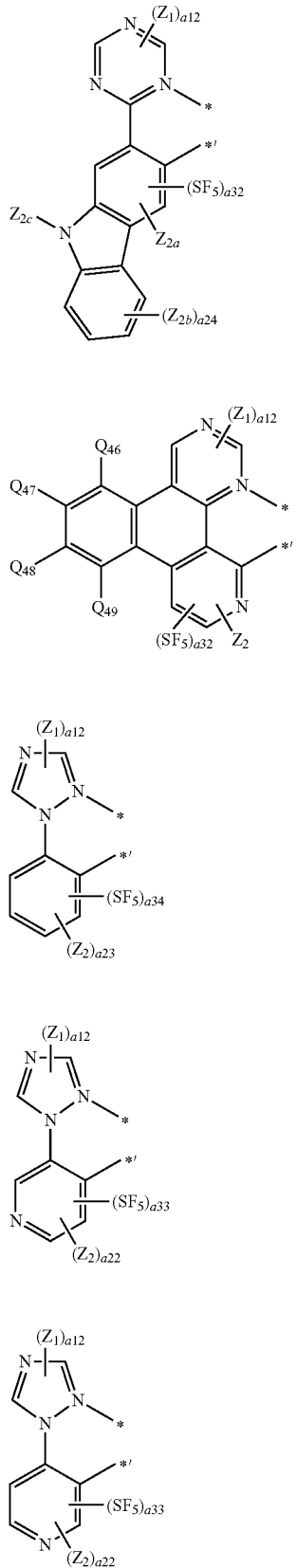

-continued
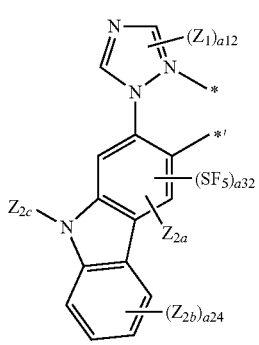
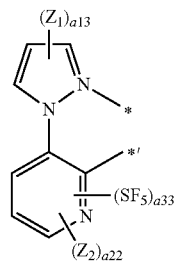
Formula 2-49
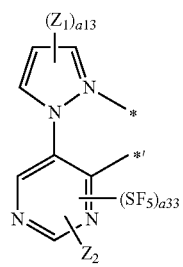
Formula 2-54
Formula 2-50
Formula 2-55
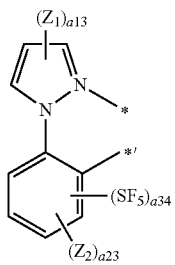
Formula 2-51
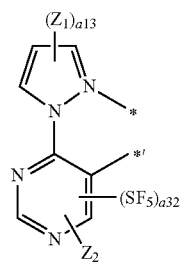
Formula 2-56
Formula 2-52
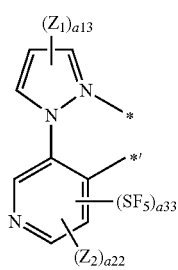
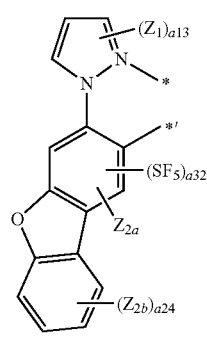
Formula 2-57
Formula 2-53
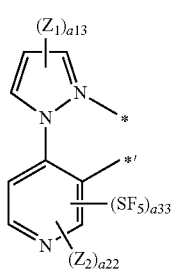
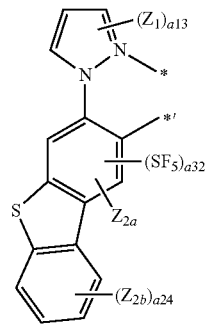
Formula 2-58

25
-continued
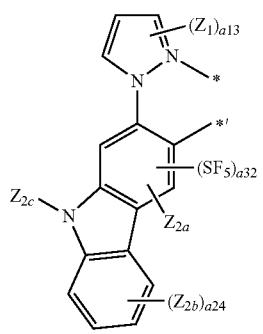
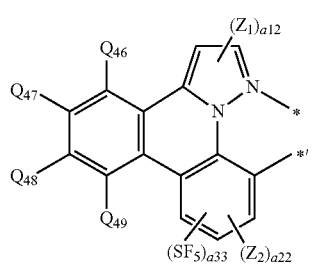
Formula 2-61
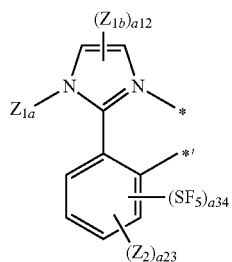
Formula 2-62
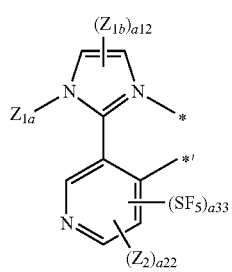
Formula 2-63
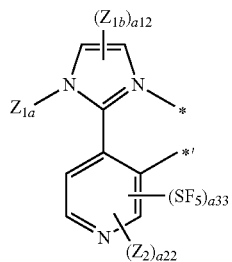
26
-continued
Formula 2-59
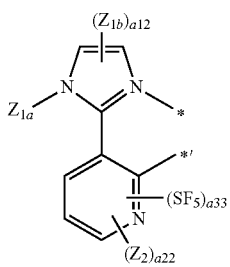
Formula 2-60
Formula 2-64
Formula 2-65
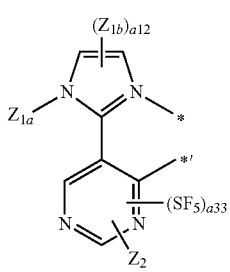
Formula 2-66
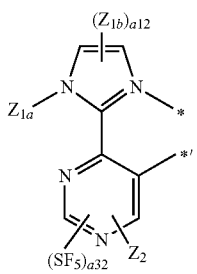
Formula 2-67
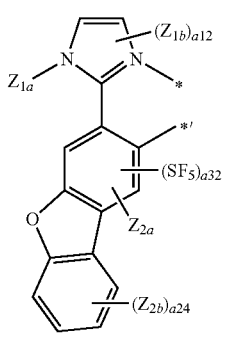
Formula 2-68
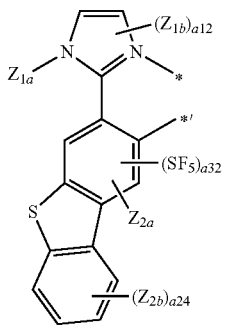

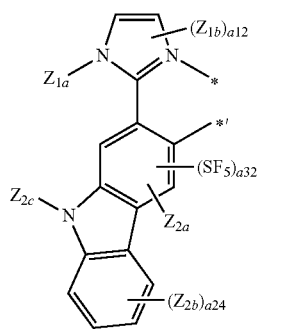
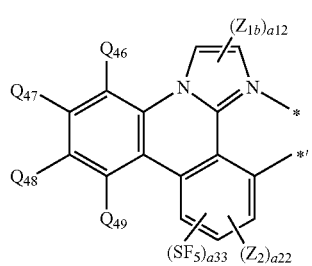
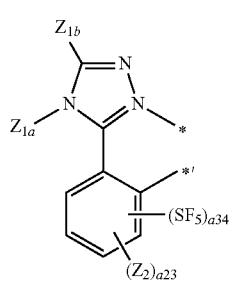
Formula 2-71
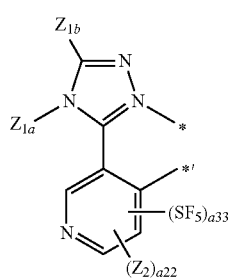
Formula 2-72
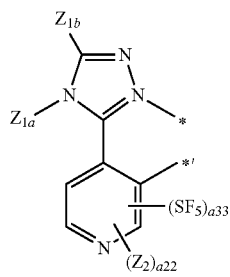
Formula 2-73
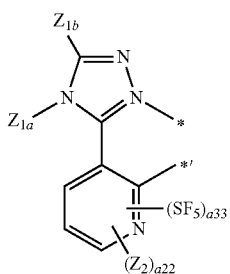
Formula 2-69
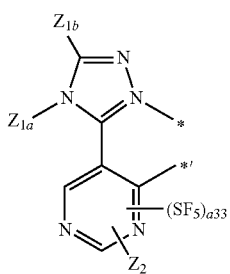
Formula 2-74
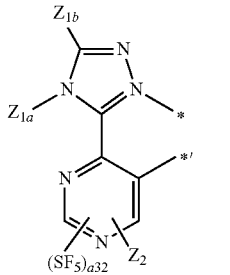
Formula 2-75
Formula 2-76
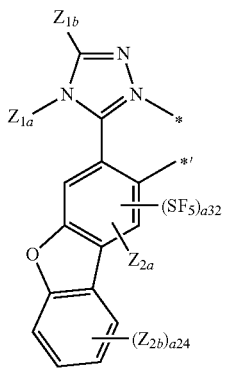
Formula 2-77
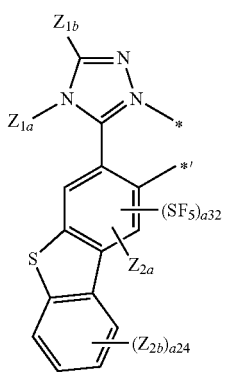
Formula 2-78

Formula 2-79
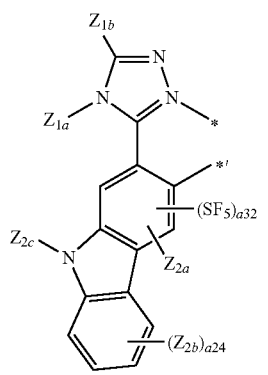
Formula 2-80
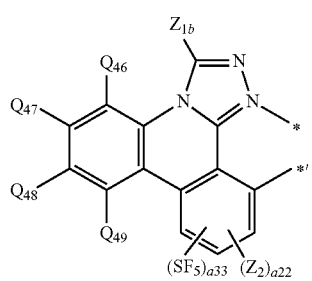
Formula 2-81
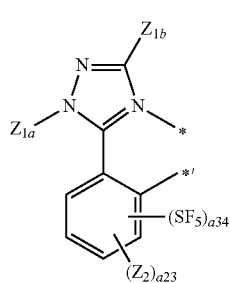
Formula 2-82
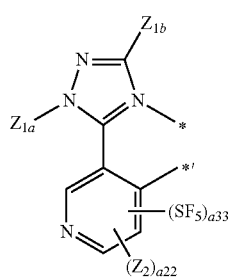
Formula 2-83
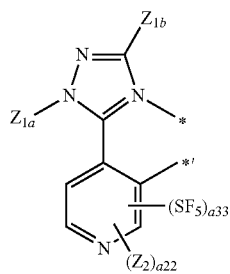
Formula 2-84
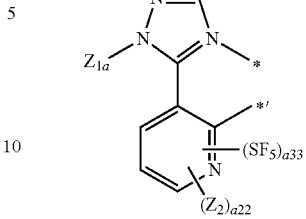
Formula 2-85
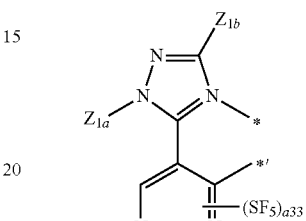
Formula 2-86
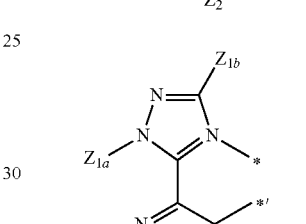
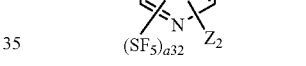
Formula 2-87
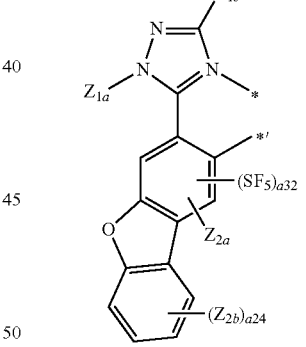
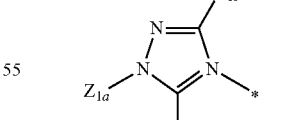
Formula 2-88
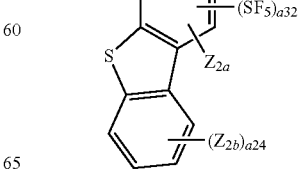

-continued
Formula 2-89
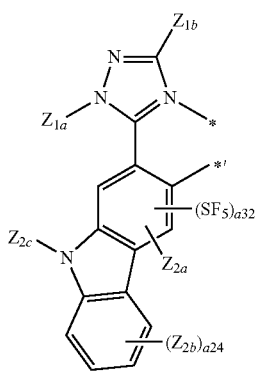
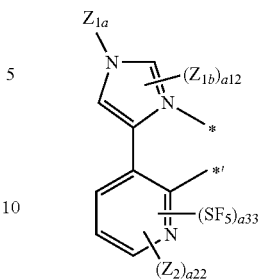
Formula 2-94
Formula 2-90
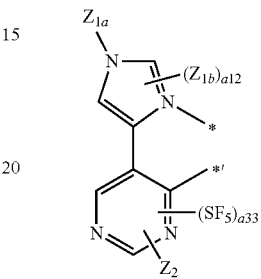
Formula 2-95
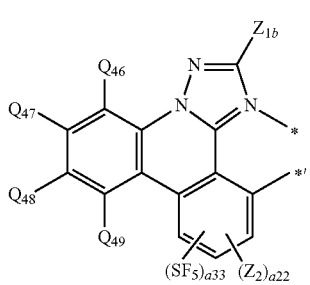
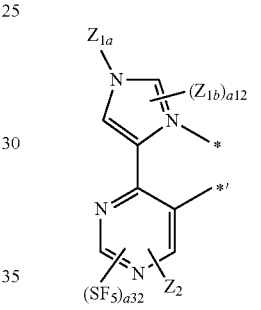
Formula 2-96
Formula 2-91
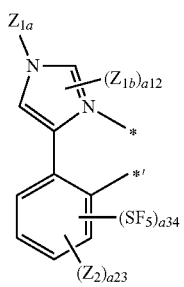
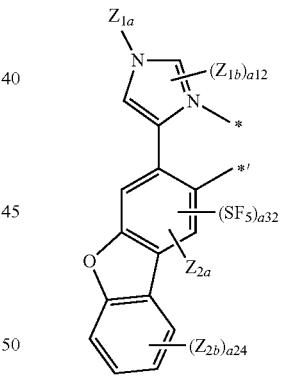
Formula 2-97
Formula 2-92
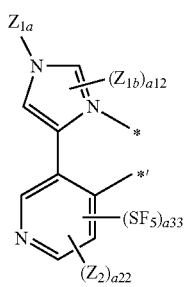
Formula 2-93
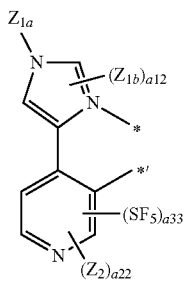
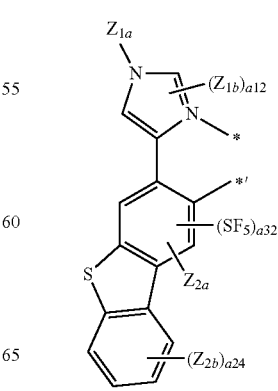
Formula 2-98

Formula 2-99 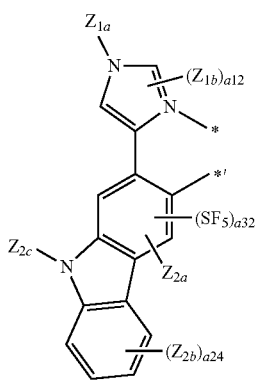
Formula 2-100 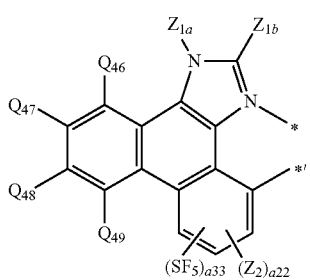
Formula 2-101 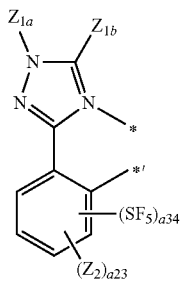
Formula 2-102 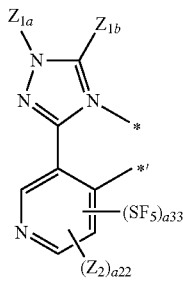
Formula 2-103 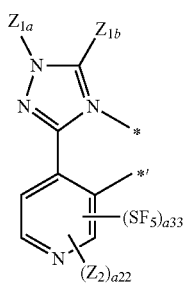
Formula 2-104 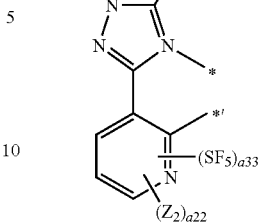
Formula 2-105 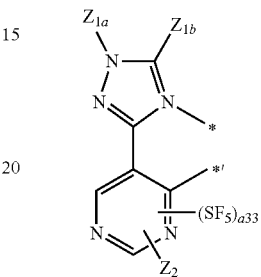
Formula 2-106 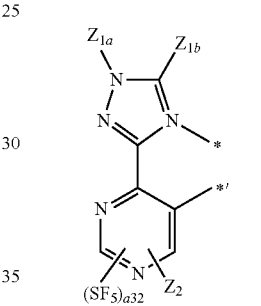
Formula 2-107 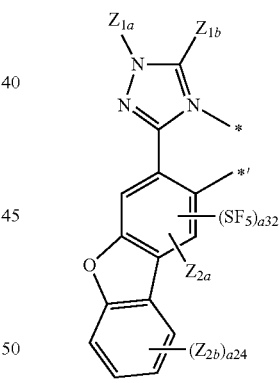
Formula 2-108 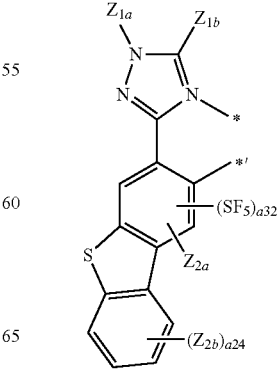

Formula 2-109
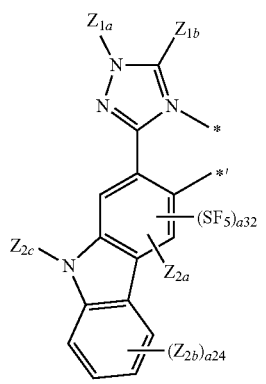
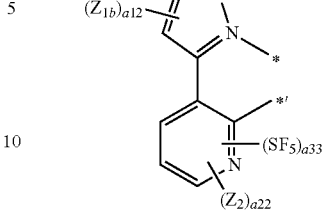
Formula 2-110
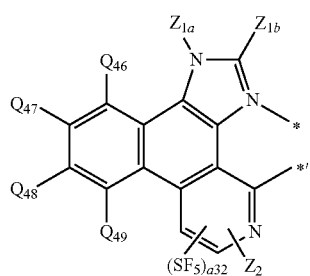
Formula 2-114
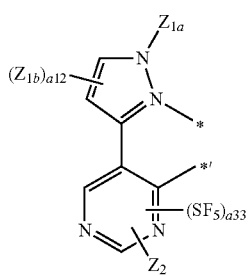
Formula 2-111
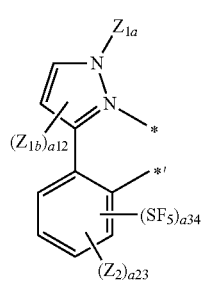
Formula 2-115
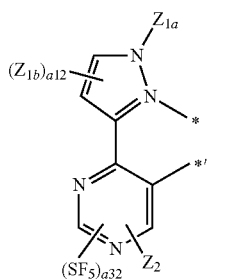
Formula 2-112
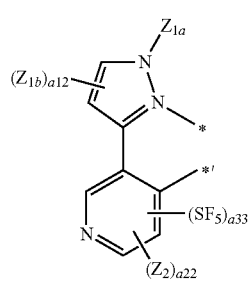
Formula 2-116
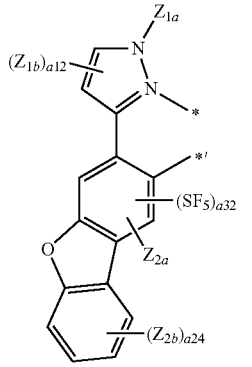
Formula 2-113
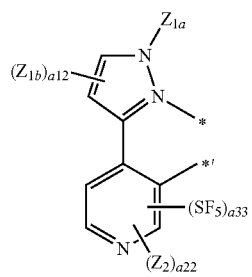
Formula 2-117
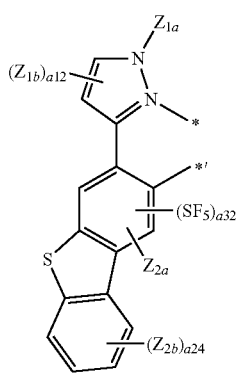
Formula 2-118

Formula 2-119 through Formula 2-128

-continued

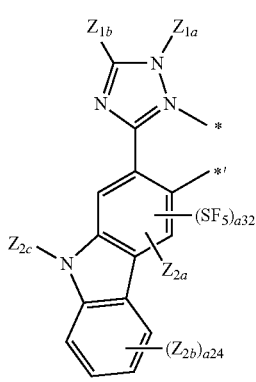

Formula 2-129

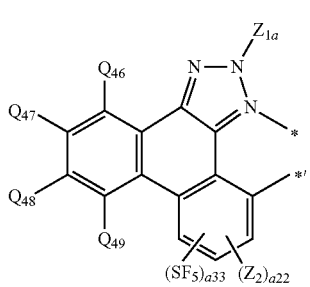

Formula 2-130 wherein in Formulae 2-1 to 2-130, $Z_1$, $Z_2$, $Q_{54}$ to $Q_{59}$, * and *' may be understood by referring to the corresponding description provided herein, $Z_{1a}$ and $Z_{1b}$ may be each independently understood by referring to the description provided herein in connection with $Z_1$, and $Z_{2a}$, $Z_{2b}$ and $Z_{2c}$ may be each independently understood by referring to the description provided herein in connection with $Z_2$, and wherein a14, a24 and a34 may be each selected from an integer of 1 to 4, a13, a23 and a33 may be each independently selected from an integer of 1 to 3, and a12, a22 and a32 may be each independently 1 or 2.

For example, in Formulae 2-1 2-130, $Z_1$, $Z_2$, $Z_{1a}$, $Z_{1b}$, $Z_{2a}$, $Z_{2b}$, $Z_{2c}$, and $Q_{54}$ to $Q_{59}$ may be each independently a hydrogen, a deuterium, —F, —Cl, —Br, —I, a hydroxyl group, a cyano group, a nitro group, an amino group, an amidino group, a hydrazine group, a hydrazone group, a carboxylic acid and a salt thereof, a sulfonic acid and a salt thereof, a phosphoric acid and a salt thereof, —SF$_5$, a $C_1$-$C_{20}$ alkyl group, or a $C_1$-$C_{20}$ alkoxy group;

a $C_1$-$C_{20}$ alkyl group or a $C_1$-$C_{20}$ alkoxy group, each substituted with at least one group selected from a deuterium, —F, —Cl, —Br, —I, a hydroxyl group, a cyano group, a nitro group, an amino group, an amidino group, a hydrazine group, a hydrazone group, a carboxylic acid and a salt thereof, a sulfonic acid and a salt thereof, a phosphoric acid and a salt thereof, a phenyl group, a naphthyl group, a pyridinyl group, and a pyrimidinyl group;

a phenyl group or a naphthyl group;

a phenyl group or a naphthyl group, each substituted with at least one group selected from a deuterium, —F, —Cl, —Br, —I, a hydroxyl group, a cyano group, a nitro group, an amino group, an amidino group, a hydrazine group, a hydrazone group, a carboxylic acid and a salt thereof, a sulfonic acid and a salt thereof, a phosphoric acid and a salt thereof, a $C_1$-$C_{20}$ alkyl group, a $C_1$-$C_{20}$ alkoxy group, a phenyl group, and a naphthyl group;

a14, a24 and a34 may be each selected from an integer of 1 to 4; and a13, a23 and a33 may be each independently selected from an integer of 1 to 3;

a12, a22 and a32 may be each independently 1 or 2; and each of * and *' may indicate a binding site with M of Formula 1.

According to another embodiment, $L_1$ of Formula 1 may be a compound represented by one of Formulae 2-1, 2-41, 2-61, 2-91, 2-111, 2-2, and 2-81, but is not limited thereto.

In Formula 1, $L_2$ may be selected from any one of a monovalent organic ligand, a divalent organic ligand, and a trivalent organic ligand.

For example, in Formula 1, $L_2$ may be selected from ligands represented by Formulae 3-1 to 3-5 below, but is not limited thereto:

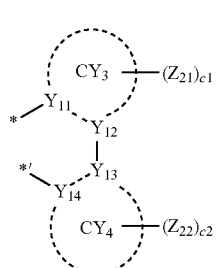

Formula 3-1

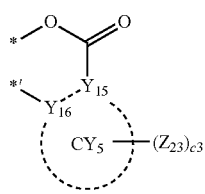

Formula 3-2

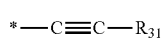

Formula 3-3

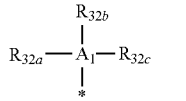

Formula 3-4

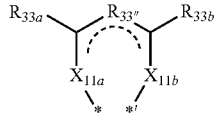

Formula 3-5

In Formulae 3-1 to 3-5, $Y_{11}$ to $Y_{16}$ may be each independently C or N;

$Y_{11}$ and $Y_{12}$ may be connected to each other via a single bond or a double bond, $Y_{13}$ and $Y_{14}$ may be connected to each other via a single bond or a double bond, and $Y_{15}$ and $Y_{16}$ may be connected to each other via a single bond or a double bond;

$CY_3$ to $CY_5$ may be each independently a $C_5$-$C_{60}$ carbocyclic group or a $C_2$-$C_{60}$ heterocyclic group, $Z_{21}$ to $Z_{23}$, $R_{31}$, $R_{32a}$, $R_{32b}$, $R_{32c}$, $R_{33a}$, $R_{33b}$, and $R_{34}$ to $R_{38}$ may be each independently a hydrogen, a deuterium, —F, —Cl, —Br, —I, a hydroxyl group, a cyano group, a nitro group, an amino group, an amidino group, a hydrazine group, a hydrazone group, a carboxylic acid and a salt thereof, a sulfonic acid and a salt thereof, a phosphoric acid and a salt thereof, a substituted or unsubstituted $C_1$-$C_{60}$ alkyl group, a substituted or unsubstituted $C_2$-$C_{60}$ alkenyl group, a substituted or unsubstituted $C_2$-$C_{60}$ alkynyl group, a substituted or unsubstituted $C_1$-$C_{60}$ alkoxy group, a substituted or unsubstituted $C_3$-$C_{10}$ cycloalkyl group, a substituted or unsubstituted $C_2$-$C_{10}$ heterocycloalkyl group, a substituted or unsubstituted $C_3$-$C_{10}$ cycloalkenyl group, a substituted or unsubstituted $C_2$-$C_{10}$ heterocycloalkenyl group, a substituted or unsubstituted $C_6$-$C_{60}$ aryl group, a substituted or unsubstituted $C_6$-$C_{60}$ aryloxy group, a substituted or unsubstituted $C_6$-$C_{60}$ arylthio group, a substituted or unsubstituted $C_2$-$C_{60}$ heteroaryl group, a substituted or unsubstituted monovalent non-aromatic condensed polycyclic group, or a substituted or unsubstituted monovalent non-aromatic condensed heteropolycyclic group;

c1 to c3 may be each independently selected from an integer of 1 to 5;

$A_1$ may be P or As;

$X_{11a}$ and $X_{11b}$ may be each independently N, O, $N(R_{34})$, $P(R_{35})(R_{36})$, or $As(R_{37})(R_{38})$;

$R_{33''}$ may be a single bond, a double bond, a substituted or unsubstituted $C_1$-$C_5$ alkylene group, or a substituted or unsubstituted $C_2$-$C_5$ alkenylene group; and each of * and *' may indicate a binding site to M of Formula 1.

In Formulae 3-1 to 3-5, $Y_{11}$ to $Y_{16}$ may be understood by referring to the description provided herein in connection with $Y_1$, $CY_3$ to $CY_5$ may be understood by referring to the description provided herein in connection with $CY_1$ and $CY_2$, $Z_{21}$ to $Z_{23}$, $R_{31}$, $R_{32a}$, $R_{32b}$, $R_{32c}$, $R_{33a}$, $R_{33b}$, and $R_{34}$ to $R_{38}$ may be understood by referring to the description provided herein in connection with $Z_1$, and c1 to c3 may be understood by referring to the description provided herein in connection with a1.

According to another embodiment, when n2 of Formula 1 is not 0, $L_2$ may be selected from ligands represented by Formulae 3-1 and 3-2.

For example, when n2 of Formula 2 is not 0, $L_2$ may be selected from ligands represented by Formulae 3-1 and 3-2, wherein in Formulae 3-1 and 3-2, $CY_3$ to $CY_5$ may be each independently benzene, naphthalene, fluorenene, spiro-fluorenene, indene, pyrrole, thiophene, furan, imidazole, pyrazole, thiazole, isothiazole, oxazole, isooxazole, triazole, pyridine, pyrazine, pyrimidine, pyridazine, quinoline, isoquinoline, benzoquinoline, quinoxaline, quinazoline, carbazole, benzoimidazole, benzofuran, benzothiophene, isobenzothiophene, benzooxazole, isobenzooxazole, triazole, tetrazole, oxadiazole, triazine, dibenzofuran, or dibenzothiophene;

$Z_{21}$ to $Z_{23}$ may be each independently a hydrogen, a deuterium, —F, —Cl, —Br, —I, a hydroxyl group, a cyano group, a nitro group, an amino group, an amidino group, a hydrazine group, a hydrazone group, a carboxylic acid and a salt thereof, a sulfonic acid and a salt thereof, a phosphoric acid and a salt thereof, a $C_1$-$C_{20}$ alkyl group, or a $C_1$-$C_{20}$ alkoxy group;

a $C_1$-$C_{20}$ alkyl group or a $C_1$-$C_{60}$ alkoxy group, each substituted with at least one group selected from a deuterium, —F, —Cl, —Br, —I, a hydroxyl group, a cyano group, a nitro group, an amino group, an amidino group, a hydrazine group, a hydrazone group, a carboxylic acid and a salt thereof, a sulfonic acid and a salt thereof, a phosphoric acid and a salt thereof, a phenyl group, a naphthyl group, a pyridinyl group, and a pyrimidinyl group;

a phenyl group, a naphthyl group, a fluorenyl group, a phenanthrenyl group, an anthracenyl group, a fluoranthrenyl group, a triphenylenyl group, a pyrenyl group, a chrysenyl group, a pyrrolyl group, a thiophenyl group, a furanyl group, an imidazolyl group, a pyrazolyl group, a thiazolyl group, an isothiazolyl group, an oxazolyl group, an isooxazolyl group, a pyridinyl group, a pyrazinyl group, a pyrimidinyl group, a pyridazinyl group, an isoindolyl group, an indolyl group, an indazolyl group, a purinyl group, a quinolinyl group, an isoquinolinyl group, a benzoquinolinyl group, a quinoxalinyl group, a quinazolinyl group, a cinnolinyl group, a carbazolyl group, a phenanthrolinyl group, a benzoimidazolyl group, a benzofuranyl group, a benzothiophenyl group, an isobenzothiazolyl group, a benzooxazolyl group, an isobenzooxazolyl group, a triazolyl group, a tetrazolyl group, an oxadiazolyl group, a triazinyl group, a dibenzofuranyl group, a dibenzothiophenyl group, a benzocarbazolyl group, a dibenzocarbazolyl group, an imidazopyridinyl group, or an imidazopyrimidinyl group; or a phenyl group, a naphthyl group, a fluorenyl group, a phenanthrenyl group, an anthracenyl group, a fluoranthrenyl group, a triphenylenyl group, a pyrenyl group, a chrysenyl group, a pyrrolyl group, a thiophenyl group, a furanyl group, an imidazolyl group, a pyrazolyl group, a thiazolyl group, an isothiazolyl group, an oxazolyl group, an isooxazolyl group, a pyridinyl group, a pyrazinyl group, a pyrimidinyl group, a pyridazinyl group, an isoindolyl group, an indolyl group, an indazolyl group, a purinyl group, a quinolinyl group, an isoquinolinyl group, a benzoquinolinyl group, a quinoxalinyl group, a quinazolinyl group, a cinnolinyl group, a carbazolyl group, a phenanthrolinyl group, a benzoimidazolyl group, a benzofuranyl group, a benzothiophenyl group, an isobenzothiazolyl group, a benzooxazolyl group, an isobenzooxazolyl group, a triazolyl group, a tetrazolyl group, an oxadiazolyl group, a triazinyl group, a dibenzofuranyl group, a dibenzothiophenyl group, a benzocarbazolyl group, a dibenzocarbazolyl group, an imidazopyridinyl group, or an imidazopyrimidinyl group, each substituted with at least one group selected from a deuterium, —F, —Cl, —Br, —I, a hydroxyl group, a cyano group, a nitro group, an amino group, an amidino group, a hydrazine group, a hydrazone group, a carboxylic acid and a salt thereof, a sulfonic acid and a salt thereof, a phosphoric acid and a salt thereof, a $C_1$-$C_{20}$ alkyl group, a $C_1$-$C_{20}$ alkoxy group, a phenyl group, a naphthyl group, a fluorenyl group, a phenanthrenyl group, an anthracenyl group, a fluoranthrenyl group, a triphenylenyl group, a pyrenyl group, a chrysenyl group, a pyrrolyl group, a thiophenyl group, a furanyl group, an imidazolyl group, a pyrazolyl group, a thiazolyl group, an isothiazolyl group, an oxazolyl group, an isooxazolyl group, a pyridinyl group, a pyrazinyl group, a pyrimidinyl group, a pyridazinyl group, an isoindolyl group, an indolyl group, an indazolyl group, a purinyl group, a quinolinyl group, an isoquinolinyl group, a benzoquinolinyl group, a quinoxalinyl group, a quinazolinyl group, a cinnolinyl group, a carbazolyl group, a phenanthrolinyl group, a benzoimidazolyl group, a benzofuranyl group, a benzothiophenyl group, an isobenzothiazolyl group, a benzooxazolyl group, an isobenzooxazolyl group, a triazolyl group, a tetrazolyl group, an oxadiazolyl group, a triazinyl group, a dibenzofuranyl group, a dibenzothiophenyl group, a benzocarbazolyl group, a dibenzocarbazolyl group, an imidazopyridinyl group, and an imidazopyrimidinyl group; and c1 to c3 may be each independently 1 or 2.

According to another embodiment, when n2 of Formula 1 is not 0, $L_2$ may be selected from ligands represented by Formulae 3-1 and 3-2, wherein in Formulae 3-1 and 3-2, $CY_3$ may be pyridine, triazole, imidazole or pyrazole, $CY_4$ may be benzene or pyridine, and $CY_5$ may be benzene;

at least one of $Y_{11}$ and $Y_{14}$ may be N;

$Z_{21}$ to $Z_{23}$ may be each independently a hydrogen, —F, a cyano group, a nitro group, a methyl group, an ethyl group, a propyl group, an n-butyl group, an isobutyl group, a sec-butyl group, a tert-butyl group, an n-pentyl group, an isopentyl group, a sec-pentyl group, a tert-pentyl group, an n-hexyl group, an isohexyl group, a sec-hexyl group, a tert-hexyl group, an n-heptyl group, an isoheptyl group, a sec-heptyl group, a tert-heptyl group, an n-octyl group, an isooctyl group, a sec-octyl group, a tert-octyl group, an n-nonyl group, an isononyl group, a sec-nonyl group, a tert-nonyl group, an n-decanyl group, an isodecanyl group, a sec-decanyl group, a tert-decanyl group, a methoxy group, an ethoxy group, a propoxy group, a butoxy group, a pentoxy group, a phenyl group, a naphthyl group, a pyridinyl group, a pyrimidinyl group, or a triazinyl group; or a methyl group, an ethyl group, a propyl group, an n-butyl group, an isobutyl group, a sec-butyl group, a tert-butyl group, an n-pentyl group, an isopentyl group, a sec-pentyl group, a tert-pentyl group, an n-hexyl group, an isohexyl group, a sec-hexyl group, a tert-hexyl group, an n-heptyl group, an isoheptyl group, a sec-heptyl group, a tert-heptyl group, an n-octyl group, an isooctyl group, a sec-octyl group, a tert-octyl group, an n-nonyl group, an isononyl group, a sec-nonyl group, a tert-nonyl group, an n-decanyl group, an isodecanyl group, a sec-decanyl group, a tert-decanyl group, a methoxy group, an ethoxy group, a propoxy group, a butoxy group, a pentoxy group, a phenyl group, a naphthyl group, a pyridinyl group, a pyrimidinyl group, or a triazinyl group, each substituted with at least one group selected from —F, a cyano group, and a nitro group; and c1 to c3 may be each independently 1 or 2.

For example, i) $CY_3$ of Formula 3-1 may be triazole, imidazole, or pyrazole, $CY_4$ of Formula 3-1 may be pyridine, $Y_{11}$ and $Y_{14}$ of Formula 3-1 may be both N; or ii) $CY_3$ of Formula 3-1 may be pyridine, $Y_{11}$ of Formula 3-1 may be N, $CY_4$ of Formula 3-1 may be benzene or pyridine, and $Y_{14}$ of Formula 3-1 may be N or C, but are not limited thereto.

In Formula 1, n1 may be selected from an integer of 1 to 3, and n2 may be selected from an integer of 0 to 4.

Variable n1 denotes the number of a ligand $L_1$ represented by Formula 2. When n1 is 2 or more, groups $L_1$ may be identical or different.

Variable n2 denotes the number of a ligand $L_2$. When n2 is 0, the organometallic compound of Formula 1 only includes the ligand $L_1$. When n2 is 2 or greater, groups $L_2$ may be identical or different.

According to another embodiment, when n1 of Formula 1 is 3, three groups $L_1$ may be identical; or when n2 of Formula 1 is 2, two groups $L_1$ may be different.

According to another embodiment, a3 of Formula 2 may be 2 or more. That is, $CY_2$ of Formula 2 may include two or more —$SF_5$ as a substituent.

According to another embodiment, a case wherein each of $Z_1$ and $Z_2$ in Formula 2 is a hydrogen may be excluded.

The organometallic compound of Formula 1 may exclude compounds below:

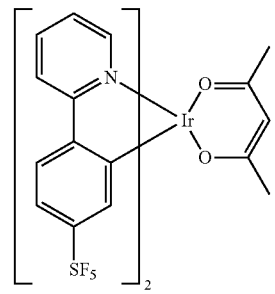

and

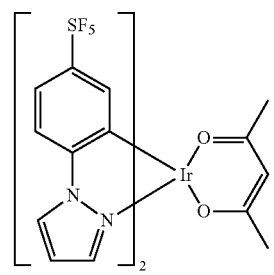

The organometallic compound of Formula 1 may be at least one of Compounds 1 to 24 below:

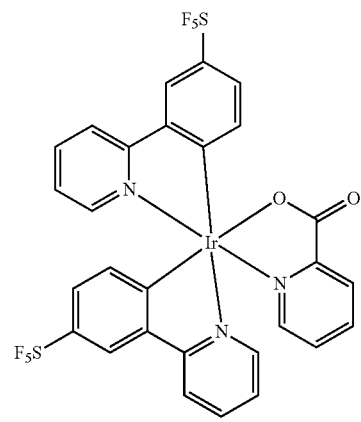

1

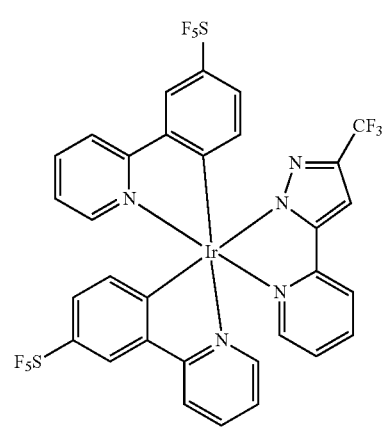

2

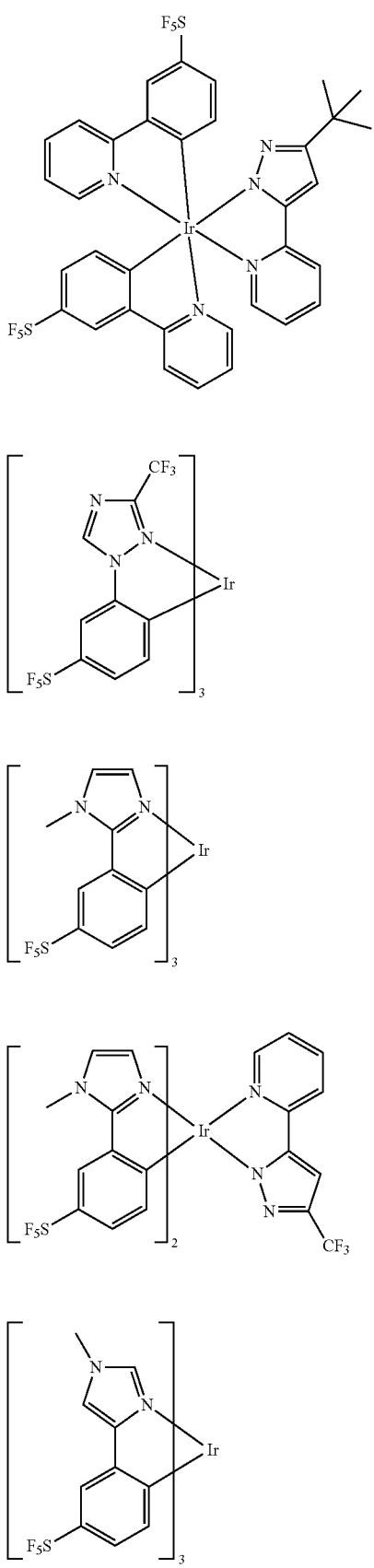
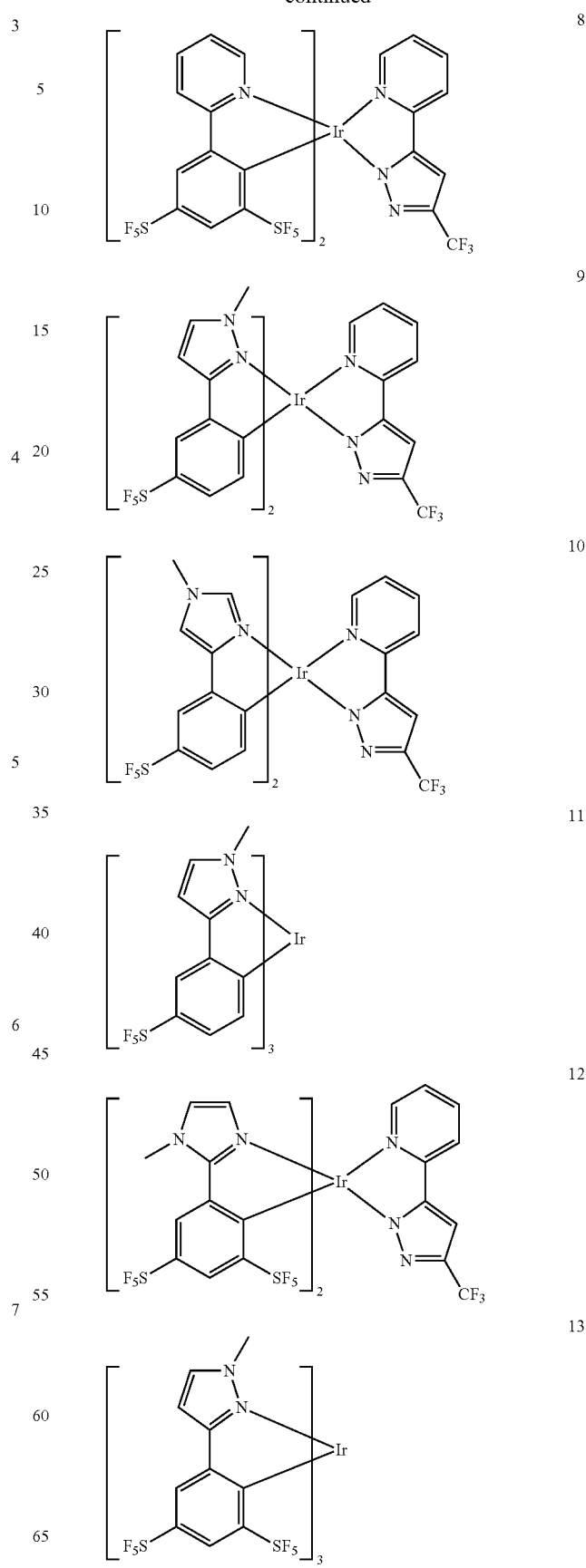

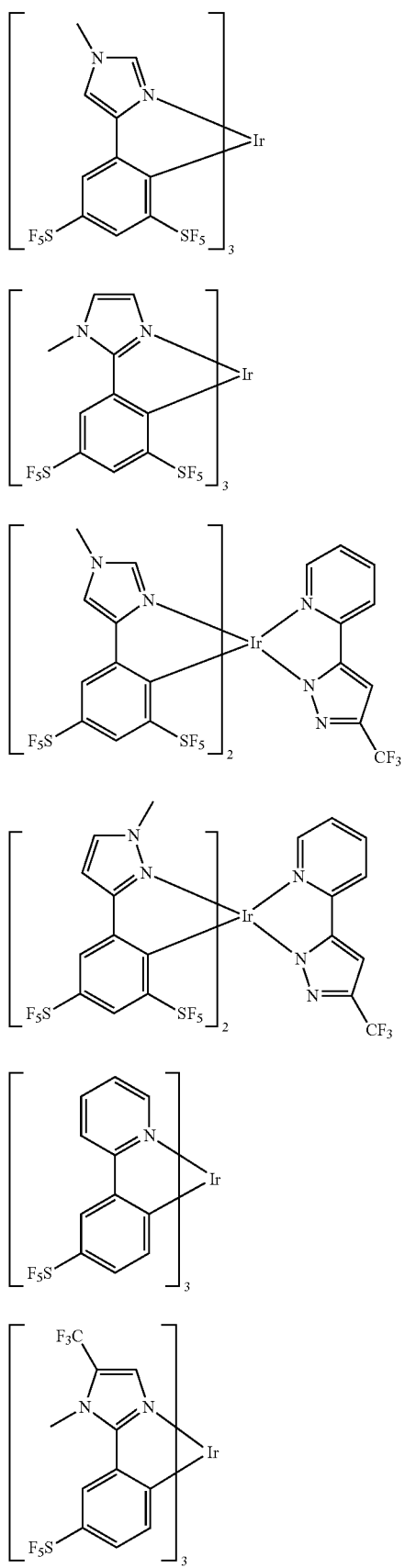
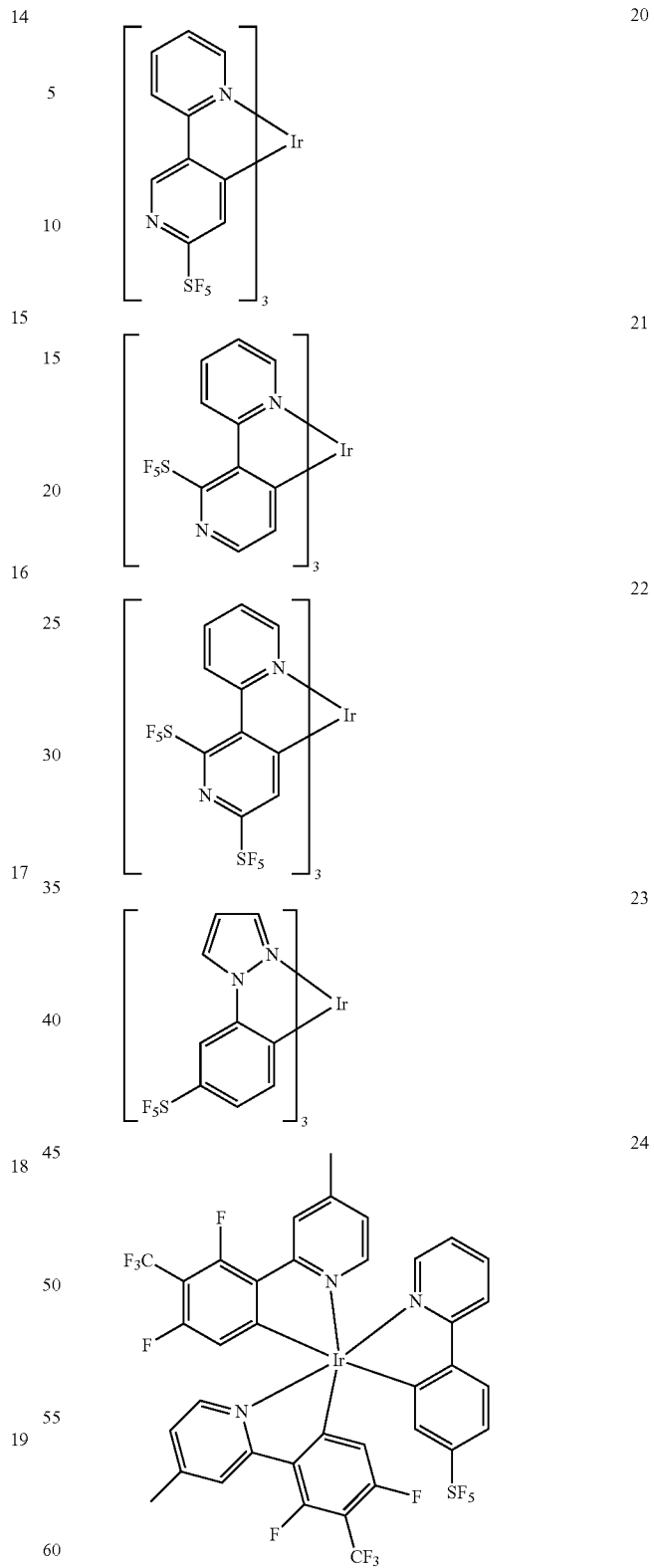
In the organometallic compound of Formula 1, a3, which denotes the number of —SF₅ groups, is not 0, and thus the organometallic compound of Formula 1 may be a compound that includes at least one —SF₅ group and is capable of emitting deep blue light.

For example, the organometallic compound of Formula 1 may emit deep blue light that has a maximum emission wavelength in a range of about 435 nanometers (nm) to about 500 nm, an x-color coordinate in a range of about 0.14 to about 0.20 (e.g., in a range of about 0.14 to about 0.18), and a y-color coordinate in a range of about 0.10 to about 0.35 (e.g., in a range of about 0.10 to about 0.25).

In addition, highest occupied molecular orbital (HOMO) levels, lowest unoccupied molecular orbital (LUMO) levels, and triplet ($T_1$) energy levels of Compounds 1, 2, 18, 19, 3, 20, 21, 22, 11, 23, and 4 are measured according to density functional calculation (DFT) method using the Gaussian program (which is performed at the B3LYP, 6-31G(d,p) level for structural optimization), and the results thereof are shown in Table 1 below.

TABLE 1

| Compound No. | HOMO (eV) | LUMO (eV) | $T_1$ energy level (eV) |
| --- | --- | --- | --- |
| 1 | −5.820 | −2.119 | 2.688 |
| 2 | −6.120 | −2.200 | 2.680 |
| 18 | −5.773 | −2.087 | 2.735 |
| 19 | −5.858 | −1.832 | 2.951 |
| 3 | −5.390 | −1.267 | 2.971 |
| 20 | −6.362 | −2.489 | 2.873 |
| 21 | −6.359 | −2.458 | 2.841 |
| 22 | −7.038 | −3.102 | 2.840 |
| 11 | −6.281 | −2.023 | 3.050 |
| 23 | −5.917 | −1.501 | 3.226 |
| 4 | −6.698 | −2.485 | 3.107 |

Referring to Table 1, it is confirmed that Compounds 1, 2, 18, 19, 3, 20, 21, 22, 11, 23, and 4 have suitable HOMO, LUMO, and $T_1$ energy levels for use as a material of an OLED. Accordingly, the organometallic compound of Formula 1 may have suitable electrical characteristics for use as a material of an OLED.

Synthesis methods for the organometallic compound of Formula 1 may be readily apparent to one of ordinary skill in the art in view of the following embodiments.

Therefore, the organometallic compound of Formula 1 may be suitable for use as an organic layer of an OLED, for example, a dopant of an emission layer that is included in the organic layer. In some embodiments, an OLED includes a first electrode; a second electrode; and an organic layer disposed between the first electrode and the second electrode, wherein the organic layer includes an emission layer and at least one of the organometallic compounds of Formula 1.

The OLED includes the above-described organic layer that includes the organometallic compound of Formula 1, and accordingly may have a low driving voltage, high efficiency, high brightness, and long lifespan. In addition, the OLED including the organometallic compound of Formula 1 may emit deep blue light that has a maximum emission wavelength in a range of about 435 nm to about 500 nm, an x-color coordinate in a range of about 0.14 to about 0.20 (e.g., in a range of about 0.14 to about 0.18), and an y-color coordinate in a range of about 0.10 to about 0.35 (e.g., in a range of about 0.10 to about 0.25).

The organometallic compound of Formula 1 may be used between a pair of electrodes of the OLED. For example, the organometallic compound of Formula 1 may be included in the emission layer, and may act as a dopant. Here, the emission layer may further include a host (that is, an amount of the organometallic compound of Formula 1 may be smaller than that of the host).

The expression "(an organic layer) includes at least one organometallic compound" used herein may be applicable when "(an organic layer) includes one organometallic compound of Formula 1 or when (an organic layer) includes two or more different organometallic compound of Formula 1".

For example, the organic layer may only include Compound 1 as the organometallic compound. In this regard, Compound 1 may be situated in the emission layer of the OLED. Alternatively, the organic layer may include Compound 1 and Compound 2 as the organometallic compound. In this regard, Compound 1 and Compound 2 may both be situated in an identical layer (for example, Compound 1 and Compound 2 may both be situated in an emission layer).

The first electrode may be an anode that is a hole injection electrode, and the second electrode may be a cathode that is an electron injection electrode. Alternatively, the first electrode may be a cathode that is an electrode injection electrode, and the second electrode may be an anode that is a hole injection electrode.

For example, the first electrode may be an anode, the second electrode may be a cathode, and the organic layer may include i) a hole transport region formed between the first electrode and the emission layer, wherein the hole transport region includes at least one of a hole injection layer, a hole transport layer, and an electron blocking layer; and ii) an electron transport region formed between the emission layer and the second electrode, wherein the electron transport region includes at least at least one of a hole blocking layer, an electron transport layer, and an electron injection layer.

The expression "organic layer" used herein refers to a single layer and/or a plurality of layers disposed between the first and second electrodes of the OLED. The "organic layer" may include not only an organic material, but also a metal-containing organic metal complex.

FIG. 1 is a schematic view of an OLED 10 according to an embodiment. Hereinafter, the structure and the method of manufacturing the OLED 10 according to an embodiment will be described in connection with FIG. 1. The OLED 10 includes a first electrode 11, an organic layer 15, and a second electrode 19 that are sequentially stacked.

A substrate may be additionally disposed under the first electrode 11 or above the second electrode 19. The substrate may be any one of substrates available for an OLED in the art. For example, the substrate may be a glass substrate or a transparent plastic substrate, each with excellent mechanical strength, thermal stability, transparency, surface smoothness, ease of handling, and water repellency.

The first electrode 11 may be formed by, for example, depositing or sputtering a material for forming the first electrode 11 on the substrate. Here, the first electrode 11 may be an anode and the material for the first electrode 11 may be selected from materials with a high work function for the holes to be easily injected. The first electrode 11 may be a reflective electrode, a semi-reflective electrode, or a transmissive electrode. The material for forming the first electrode 11 may be indium tin oxide (ITO), indium zinc oxide (IZO), tin oxide (SnO$_2$), and zinc oxide (ZnO). Alternatively, the material for forming the first electrode 11 may be metal such as magnesium (Mg), aluminum (Al), aluminum-lithium (Al—Li), calcium (Ca), magnesium-indium (Mg—In), and magnesium-silver (Mg—Ag).

The first electrode 11 may have a single-layer structure or a multi-layer structure including two or more layers. For example, the first electrode 11 may have a three-layered structure of ITO/Ag/ITO, but the structure of the first electrode 11 is not limited thereto.

The organic layer 15 is disposed on the first electrode 11.

The organic layer 15 may include a hole transport region; an emission layer; and an electron transport region.

The hole transport region may be formed between the first electrode 11 and the emission layer.

The hole transport region may include at least one of a hole injection layer, a hole transport layer, an electron blocking layer, and a buffer layer.

The hole transport region may include a hole injection layer only, or a hole transport layer only. Alternatively, the hole transport region may have a structure of hole injection layer/hole transport layer or a structure of hole injection layer/hole transport layer/electron blocking layer, wherein layers of each structure are sequentially stacked from the first electrode 11 in this stated order.

When the hole transport region includes a hole injection layer, the hole injection layer (HIL) may be formed on the first electrode 11 by using various methods, such as vacuum deposition, spin coating, vesting, and a Langmuir-Blodgett (LB) method.

When a HIL is formed by vacuum deposition, the vacuum deposition may be, for example, performed at a deposition temperature of about 100° C. to about 500° C., at a vacuum degree of about $10^{-8}$ to about $10^{-3}$ torr, and at a deposition rate of about 0.01 to about 100 Angstrom per second (Å/sec) in consideration of a compound for a HIL to be deposited, and the structure and thermal characteristics of a HIL to be formed, but the conditions are not limited thereto.

When a HIL is formed by spin coating, the spin coating may be performed at a coating rate of about 2,000 revolutions per minute (rpm) to about 5,000 rpm, and at a temperature of about 80° C. to 200° C. depending on a compound for a HIL to be deposited, and the structure and thermal characteristics of a HIL to be formed, but the conditions are not limited thereto.

Conditions for forming the hole transport layer and the electron blocking layer may be understood by referring to the conditions for forming an HIL.

The hole transport region may include, for example, at least one compound selected from m-MTDATA, TDATA, 2-TNATA, NPB, β-NPB, TPD, Spiro-TPD, Spiro-NPB, α-NPB, TAPC, HMTPD, 4,4',4"-tris(N-carbazolyl)triphenylamine) (TCTA), polyaniline/dodecylbenzenesulfonic acid (Pani/DBSA), poly(3,4-ethylenedioxythiophene)/poly(4-styrenesulfonate) (PEDOT/PSS), polyaniline/camphor sulfonic acid (Pani/CSA), polyaniline)/poly(4-styrenesulfonate) (PANI/PSS), a compound represented by Formula 201 below, and a compound represented by Formula 202 below:

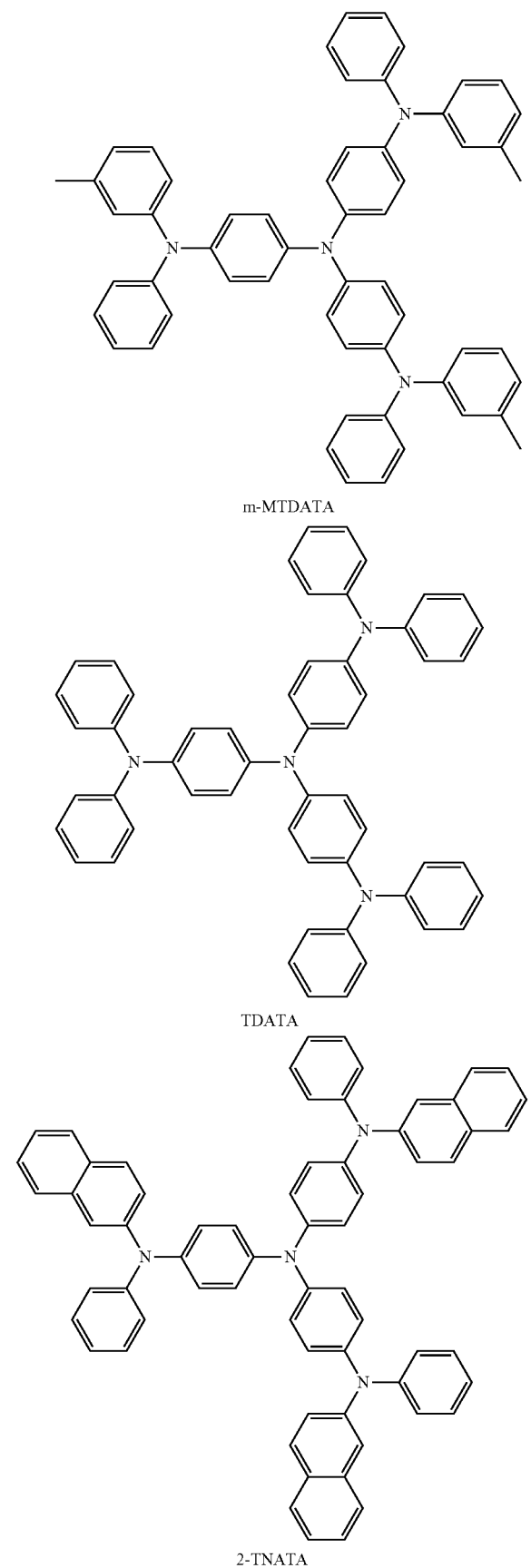

-continued
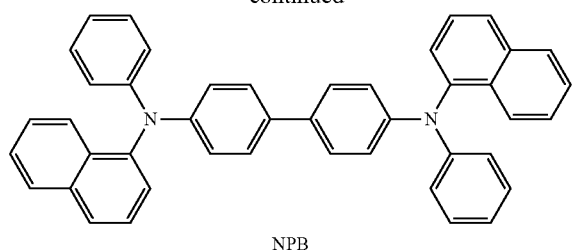
NPB
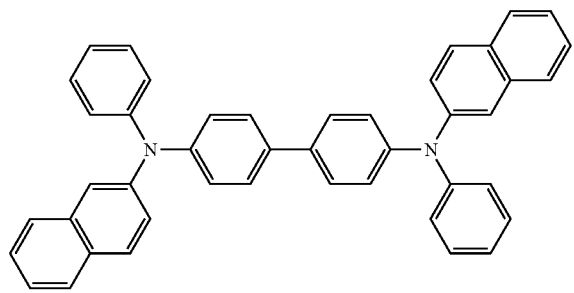
β-NPB
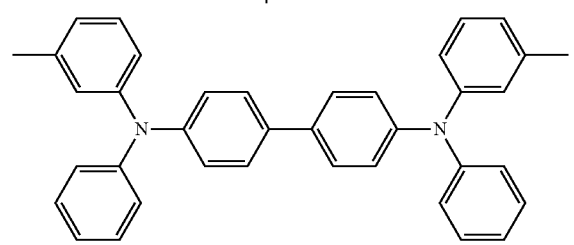
TPD
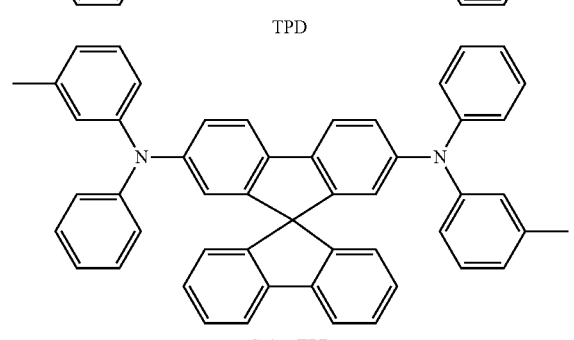
Spiro-TPB
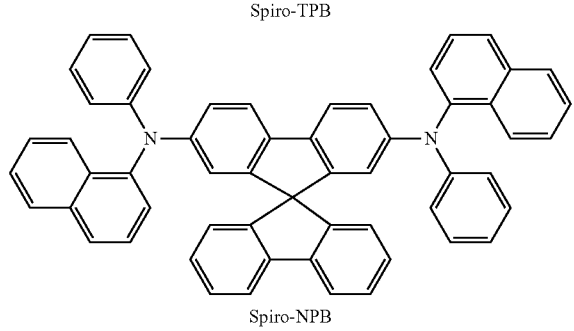
Spiro-NPB
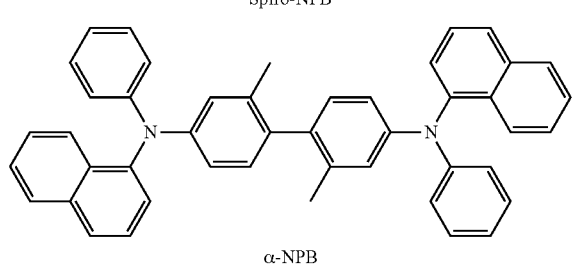
α-NPB
-continued
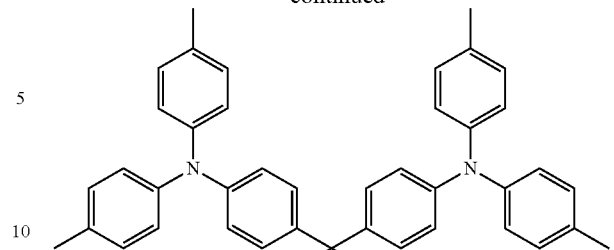
TAPC
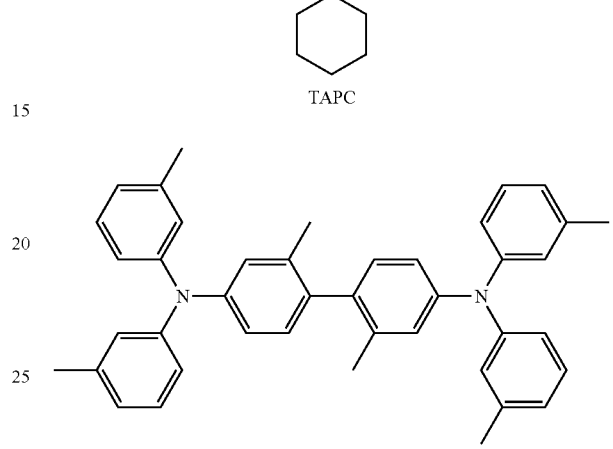
HMTPD
Formula 201
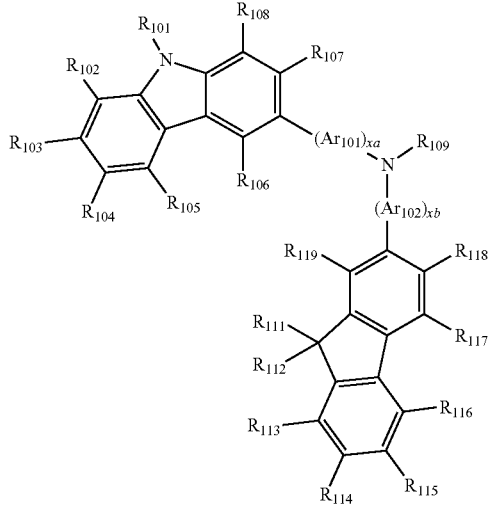
Formula 202
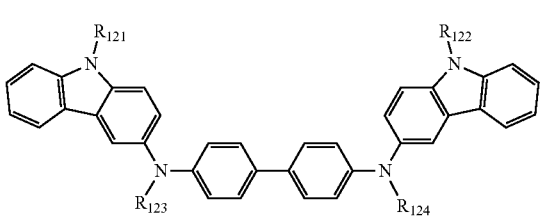
wherein in Formula 201, $Ar_{101}$ and $Ar_{102}$ may be each independently
a phenylene group, a pentalenylene group, an indenylene group, a naphthylene group, an azulenylene group, a heptalenylene group, an acenaphthylene group, a fluorenylene group, a phenalenylene group, a phenanthrenylene group, an anthracenylene group, a fluoranthrenylene group, a triphenylenylene group, a pyrenylene group, a chrysenylene group, a naphthacenylene group, a picenylene group, a perylenylene group, or a pentaphenylene group; and a phenylene group, a pentalenylene group, an indenylene group, a naphthylene group, an azulenylene group, a heptalenylene group, an acenaphthylene group, a fluorenylene group, a phenalenylene group, a phenanthrenylene group, an anthracenylene group, a fluoranthrenylene group, a triphenylenylene group, a pyrenylene group, a chrysenylene group, a naphthacenylene group, a picenylene group, a perylenylene group, or a pentaphenylene group, each substituted with at least one group selected from a deuterium, —F, —Cl, —Br, —I, a hydroxyl group, a cyano group, a nitro group, an amino group, an amidino group, a hydrazine group, a hydrazone group, a carboxylic acid and a salt thereof, a sulfonic acid and a salt thereof, a phosphoric acid and a salt thereof, a $C_1$-$C_{60}$ alkyl group, a $C_2$-$C_{60}$ alkenyl group, a $C_2$-$C_{60}$ alkynyl group, a $C_1$-$C_{60}$ alkoxy group, a $C_3$-$C_{10}$ cycloalkyl group, a $C_3$-$C_{10}$ cycloalkenyl group, a $C_2$-$C_{10}$ heterocycloalkyl group, a $C_2$-$C_{10}$ heterocycloalkenyl group, a $C_6$-$C_{60}$ aryl group, a $C_6$-$C_{60}$ aryloxy group, a $C_6$-$C_{60}$ arylthio group, a $C_2$-$C_{60}$ heteroaryl group, a monovalent non-aromatic condensed polycyclic group, and a monovalent non-aromatic condensed heteropolycyclic group.

In Formula 201, xa and xb may be each independently an integer of 0 to 5, or may be each independently 0, 1, or 2. For example, xa may be 1 and xb may be 0, but are not limited thereto.

In Formulae 201 and 202, $R_{101}$ to $R_{108}$, $R_{111}$ to $R_{119}$, and $R_{121}$ to $R_{124}$ may be each independently a hydrogen, a deuterium, —F, —Cl, —Br, —I, a hydroxyl group, a cyano group, a nitro group, an amino group, an amidino group, a hydrazine group, a hydrazone group, a carboxylic acid and a salt thereof, a sulfonic acid and a salt thereof, a phosphoric acid and a salt thereof, a $C_1$-$C_{10}$ alkyl group (e.g., a methyl group, an ethyl group, a propyl group, a butyl group, a pentyl group, and a hexyl group) or a $C_1$-$C_{10}$ alkoxy group (e.g., a methoxy group, an ethoxy group, a propoxy group, a butoxy group, and a pentoxy group);

a $C_1$-$C_{10}$ alkyl group or a $C_1$-$C_{10}$ alkoxy group, each substituted with at least one group selected from a deuterium, —F, —Cl, —Br, —I, a hydroxyl group, a cyano group, a nitro group, an amino group, an amidino group, a hydrazine group, a hydrazone group, a carboxylic acid and a salt thereof, a sulfonic acid and a salt thereof, and a phosphoric acid and a salt thereof;

a phenyl group, a naphthyl group, an anthracenyl group, a fluorenyl group, or a pyrenyl group; and a phenyl group, a naphthyl group, an anthracenyl group, a fluorenyl group, or a pyrenyl group, each substituted with at least one group selected from a deuterium, —F, —Cl, —Br, —I, a hydroxyl group, a cyano group, a nitro group, an amino group, an amidino group, a hydrazine group, a hydrazone group, a carboxylic acid and a salt thereof, a sulfonic acid and a salt thereof, a phosphoric acid and a salt thereof, a $C_1$-$C_{10}$ alkyl group, and a $C_1$-$C_{10}$ alkoxy group, but are not limited thereto.

In Formula 201, $R_{109}$ may be a phenyl group, a naphthyl group, an anthracenyl group, a pyridinyl group; a phenyl group, a naphthyl group, an anthracenyl group, or a pyridinyl group, each substituted with at least one group selected from a deuterium, —F, —Cl, —Br, —I, a hydroxyl group, a cyano group, a nitro group, an amino group, an amidino group, a hydrazine group, a hydrazone group, a carboxylic acid and a salt thereof, a sulfonic acid and a salt thereof, a phosphoric acid and a salt thereof, a $C_1$-$C_{20}$ alkyl group, a $C_1$-$C_{20}$ alkoxy group, a phenyl group, a naphthyl group, an anthracenylene group, and a pyridinyl group.

According to another embodiment, the compound of Formula 201 may be represented by Formula 201A below, but is not limited thereto:

Formula 201A

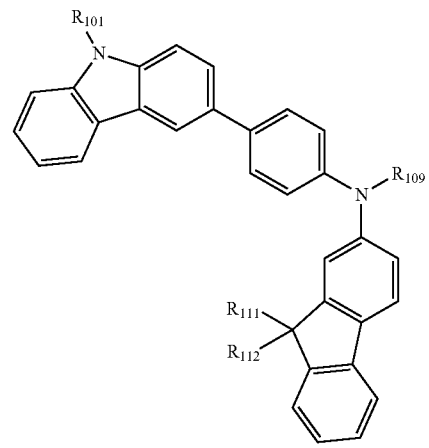

wherein in Formula 201A, $R_{101}$, $R_{111}$, $R_{112}$, and $R_{109}$ may be understood by referring to the corresponding description provided herein.

For example, the compound of Formula 201 and the compound of Formula 202 may include Compounds HT1 to HT20 illustrated below, but are not limited thereto:

HT1

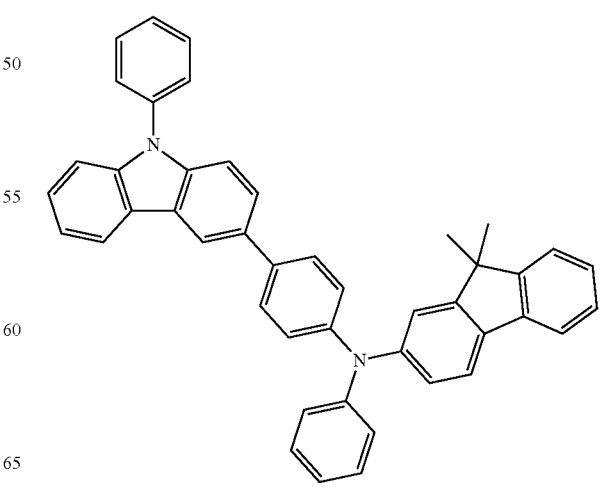

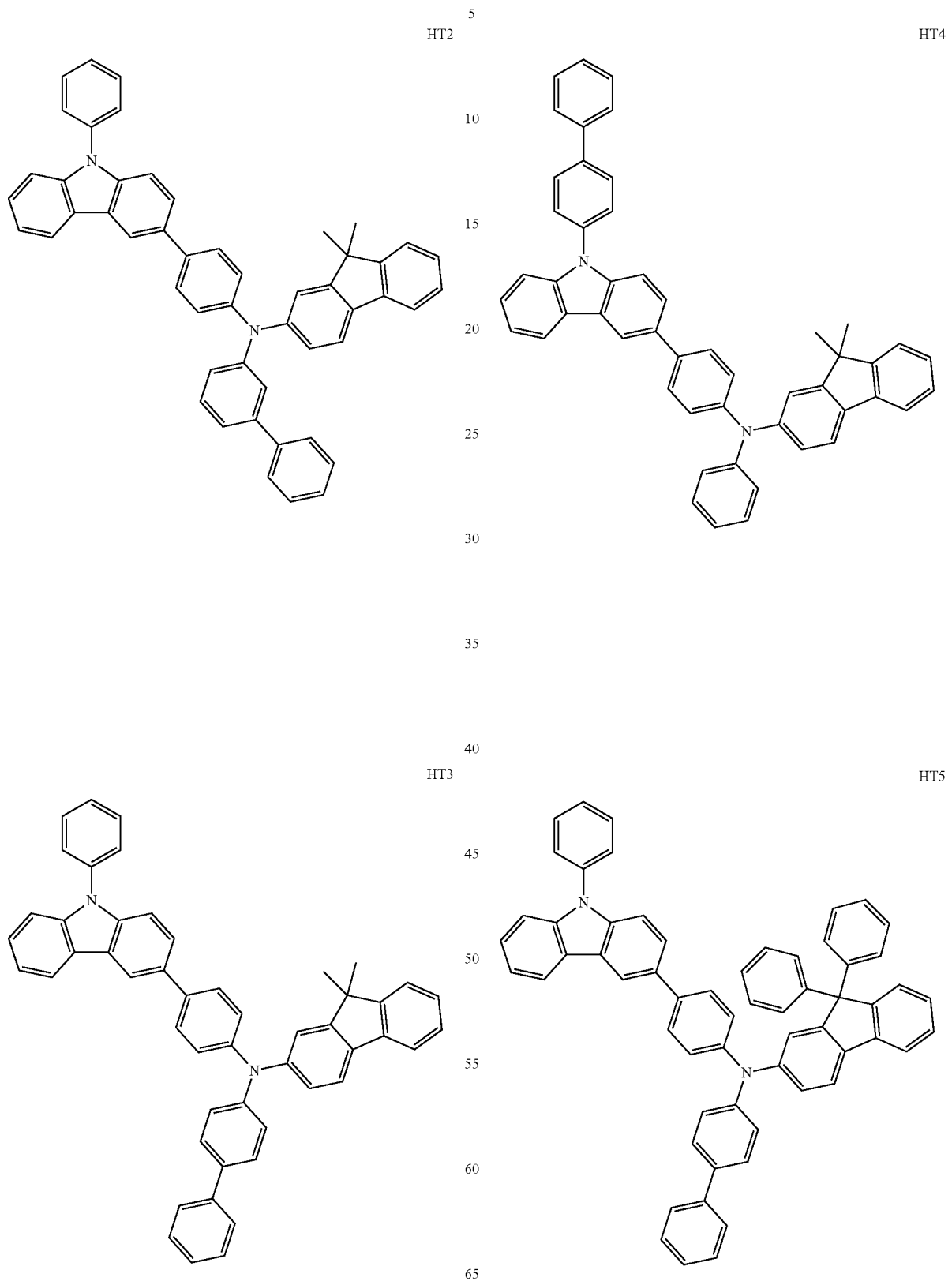

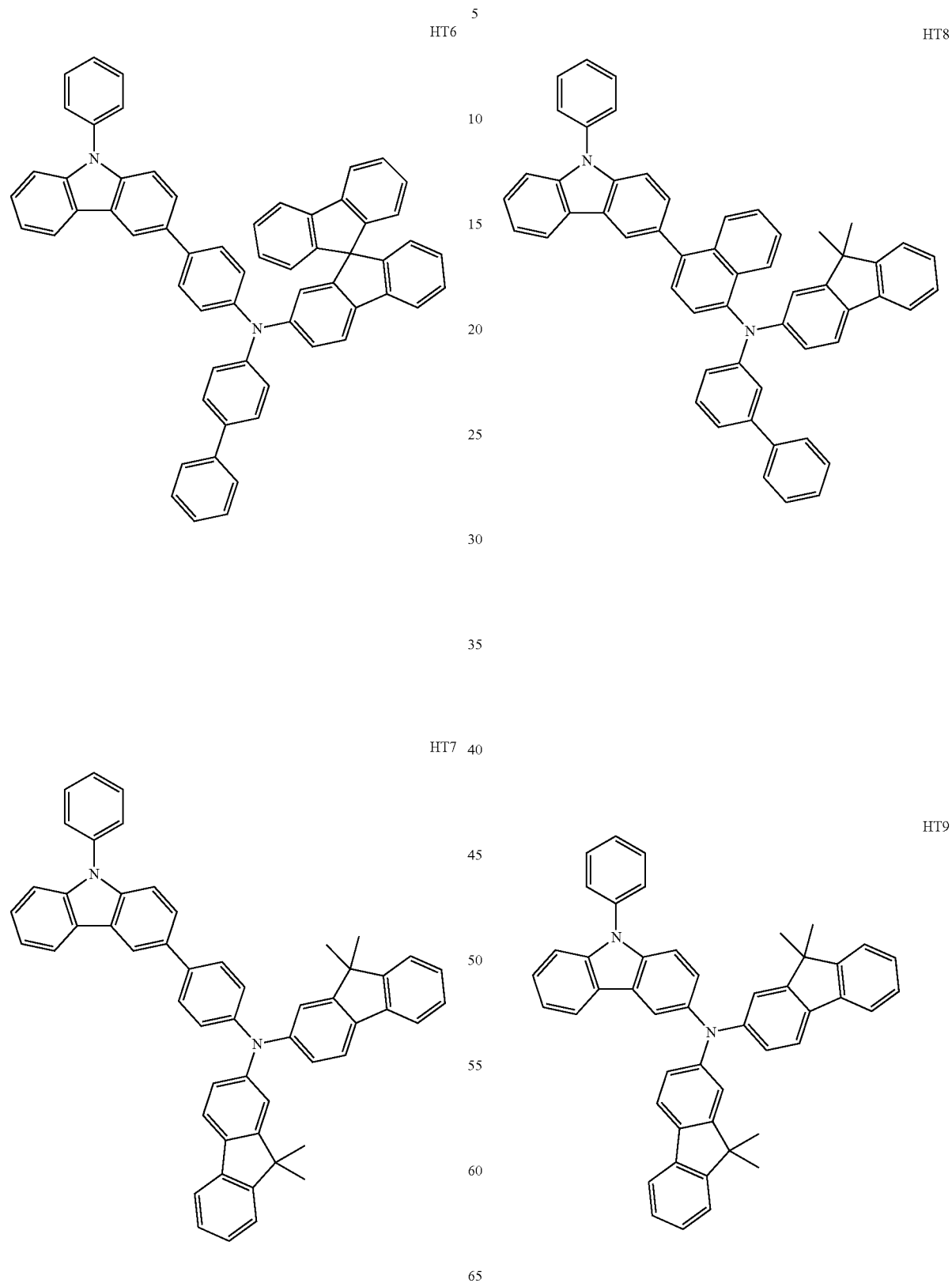

HT10
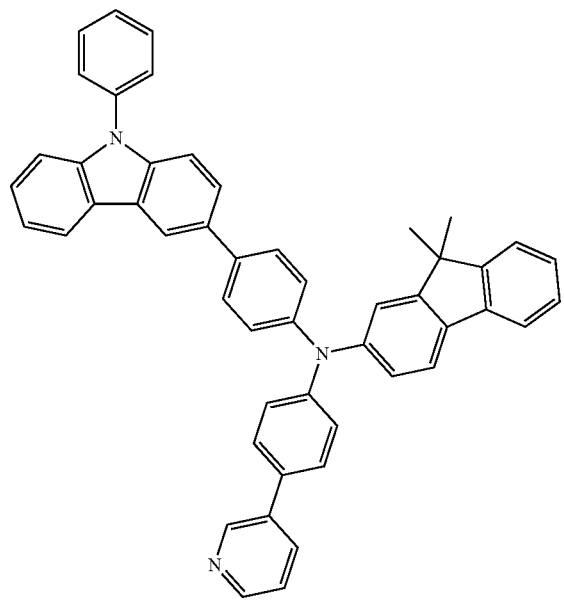
HT11
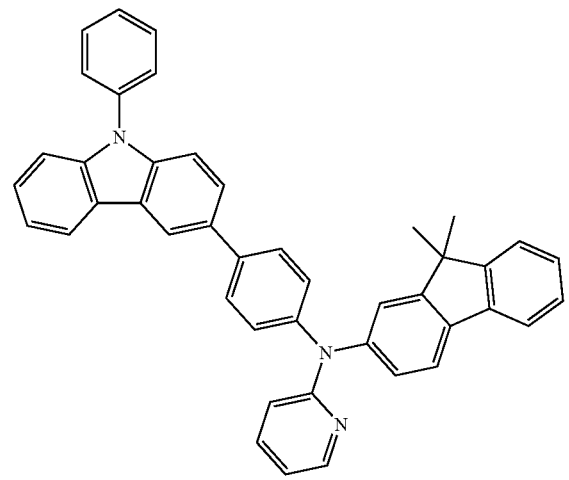
HT12
HT13
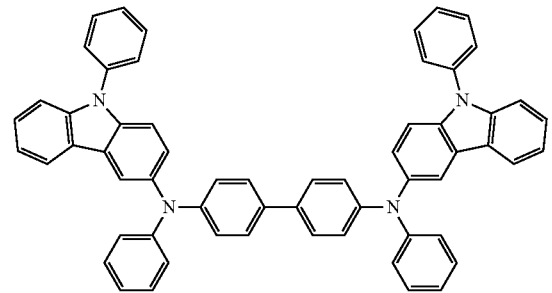
HT14
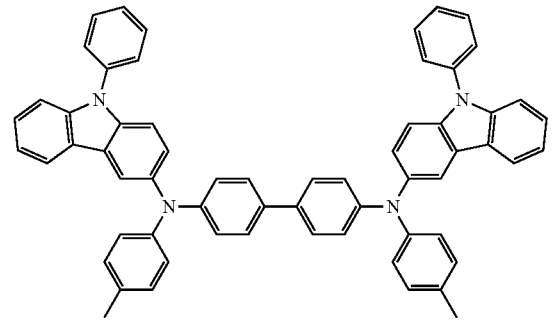
HT15
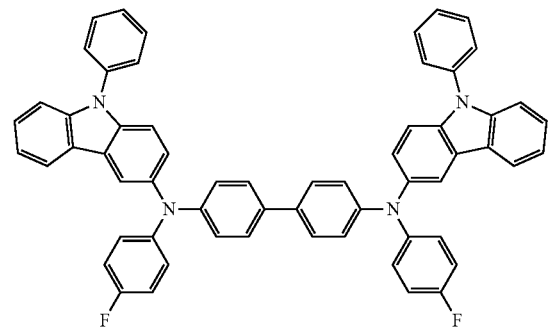

HT16

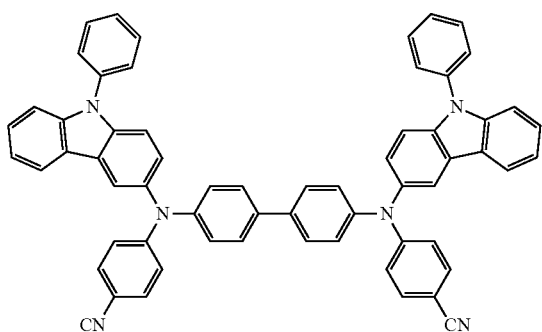

HT20

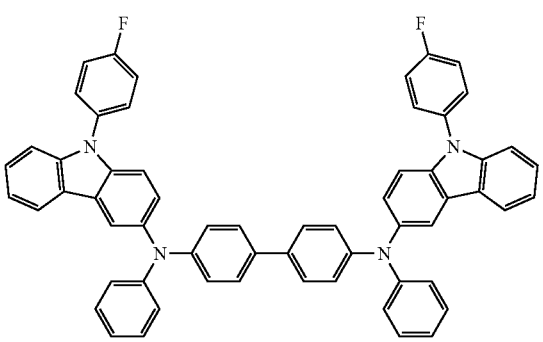

HT17

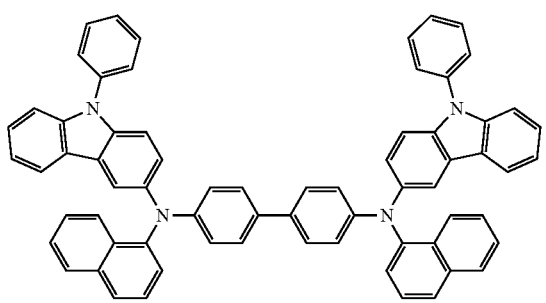

A thickness of the hole transport region may be in a range of about 100 Angstrom (Å) to about 10,000 Å, for example, about 100 Å to about 1,000 Å. When the hole transport region includes both a hole injection layer and a hole transport layer, a thickness of the hole injection layer may be in a range of about 100 Å to about 10,000 Å, for example, about 100 Å to about 1,000 Å, and a thickness of the hole transport layer may be in a range of about 50 Å to about 2,000 Å, for example, about 100 Å to about 1,500 Å. When the thicknesses of the hole transport region, the hole injection layer, and the hole transport layer are within these ranges, satisfactory hole transporting characteristics may be obtained without a substantial increase in driving voltage.

HT18

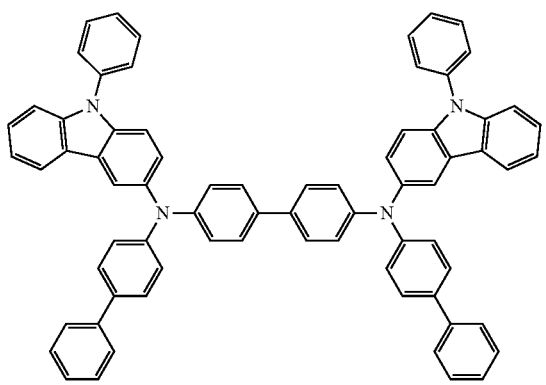

The hole transport region may further include, in addition to these materials, a charge-generation material for the improvement of conductive properties. The charge-generation material may be homogeneously or non-homogeneously dispersed in the hole transport region.

The charge-generation material may be, for example, a p-dopant. The p-dopant may be one of a quinone derivative, a metal oxide, and a cyano group-containing compound, but is not limited thereto. For example, non-limiting examples of the p-dopant are a quinone derivative, such as tetracyanoquinonedimethane (TCNQ) and 2,3,5,6-tetrafluoro-tetracyano-1,4-benzoquinonedimethane (F4-TCNQ); a metal oxide, such as a tungsten oxide and a molybdenum oxide; and Compound HT-D1 below, but are not limited thereto.

HT19

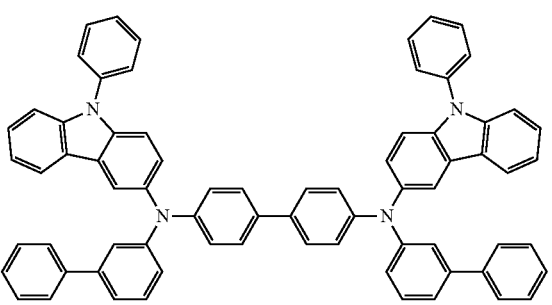

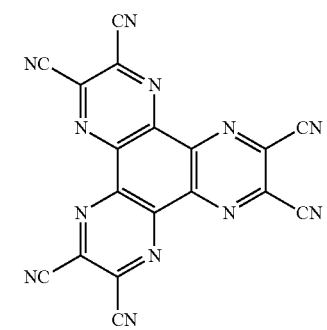

Compound HT-D1

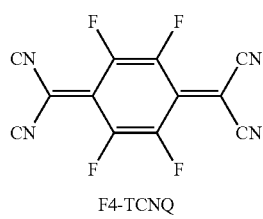

F4-TCNQ

The hole transport region may further include a buffer layer.

The buffer layer may compensate for an optical resonance distance according to a wavelength of light emitted from the emission layer.

An emission layer (EML) is formed on the hole transport region by using various methods, such as vacuum deposition, spin coating, casting, and an LB method. When the EML is formed by vacuum deposition and spin coating, deposition and coating conditions for the EML may be determined by referring to the deposition and coating conditions for the HIL in consideration of a compound to be used.

The EML may include a host and a dopant, and the dopant may include the organometallic compound of Formula 1.

The host may include at least one compound selected from TPBi, TBADN, ADN (also referred to as "DNA"), CBP, CDBP, and TCP:

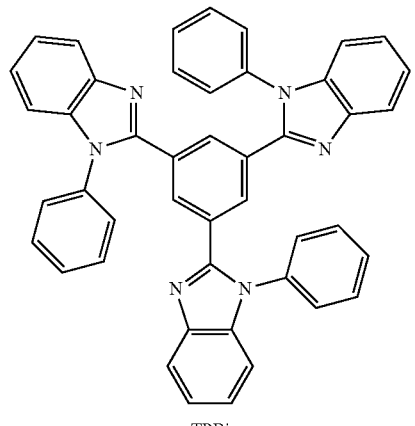

TPBi

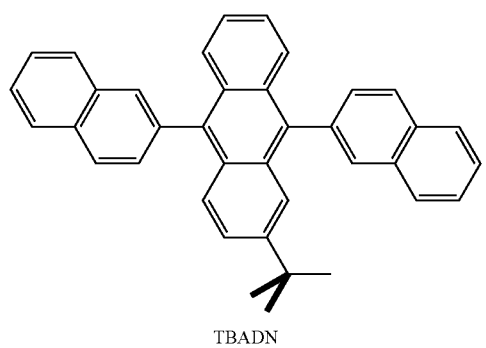

TBADN

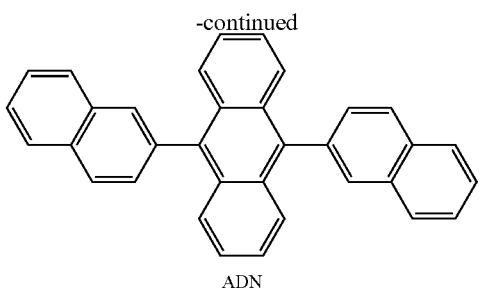

ADN

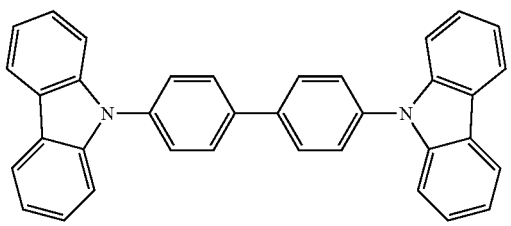

CBP

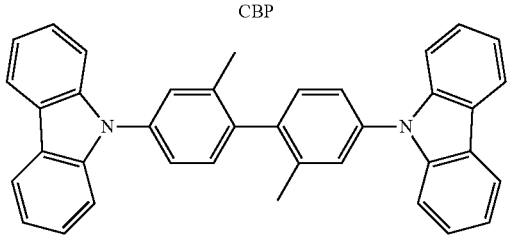

CDBP

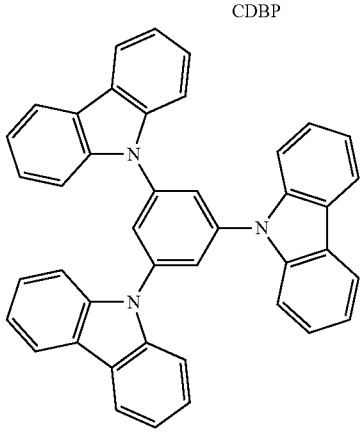

TCP

Alternatively, the host may include a compound represented by Formula 201 below:

Formula 301

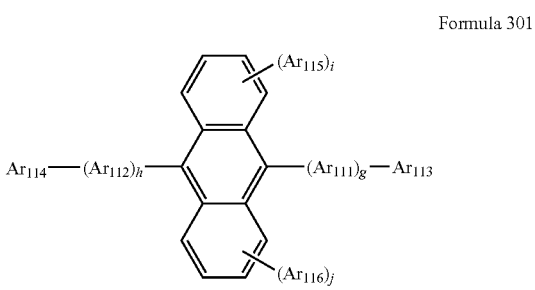

wherein in Formula 301, $Ar_{111}$ and $Ar_{112}$ may be each independently selected from a phenylene group, a naphthylene group, a phenanthrenylene group, or a pyrenylene group; or a phenylene group, a naphthylene group, a phenanthrenylene group, or a pyrenylene group, each substituted with at least one group selected from a phenyl group, a naphthyl group, and an anthracenylene group.

In Formula 301, $Ar_{113}$ to $Ar_{116}$ may be each independently selected from a $C_1$-$C_{10}$ alkyl group; a phenyl group, a naphthyl group, a phenanthrenyl group, a pyrenylene group; a naphthyl group, a phenanthrenyl group, or a pyrenyl group, each substituted with at least one group selected from a phenyl group, a naphthyl group, and an anthracenyl group.

In Formula 301, g, h, l, and j may be each independently an integer of 0 to 4, for example, may be each independently 0, 1, or 2.

In Formula 301, $Ar_{113}$ to $Ar_{116}$ may be each independently a $C_1$-$C_{10}$ alkyl group substituted with at least one group selected from a phenyl group, a naphthyl group, and an anthracenyl group;

a phenyl group, a naphthyl group, an anthracenyl group, a pyrenyl group, a phenanthrenyl group, or a fluorenyl group;

a phenyl group, a naphthyl group, an anthracenyl group, a pyrenyl group, a phenanthrenyl group, or a fluorenyl group, each substituted with at least one group selected from a deuterium, —F, —Cl, —Br, —I, a hydroxyl group, a cyano group, a nitro group, an amino group, an amidino group, a hydrazine group, a hydrazone group, a carboxylic acid and a salt thereof, a sulfonic acid and a salt thereof, a phosphoric acid and a salt thereof, a $C_1$-$C_{60}$ alkyl group, a $C_2$-$C_{60}$ alkenyl group, a $C_2$-$C_{60}$ alkynyl group, a $C_1$-$C_{60}$ alkoxy group, a phenyl group, a naphthyl group, an anthracenyl group, a pyrenyl group, a phenanthrenyl group, and a fluorenyl group; or

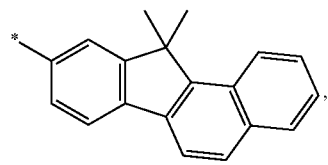 [SMILES: *c1ccc2c(c1)C(C)(C)c1c-2ccc2ccccc12]

but are not limited thereto.

Alternatively, the host may include a compound represented by Formula 302 below:

Formula 302

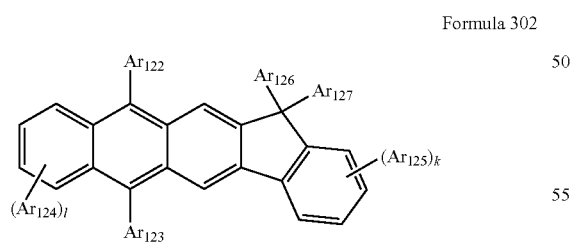

In Formula 302, $Ar_{122}$ to $Ar_{125}$ may be understood by referring to the description provided herein in connection with $Ar_{113}$ of Formula 301.

In Formula 302, $Ar_{126}$ and $Ar_{127}$ may be each independently a $C_1$-$C_{10}$ alkyl group (e.g., a methyl group, an ethyl group, or a propyl group).

In Formula 302, k and l may be each independently an integer of 0 to 4. For example, k and l may be each independently 0, 1, or 2.

The compound of 301 and the compound of 302 may include Compounds H1 to H42 illustrated below, but are not limited thereto.

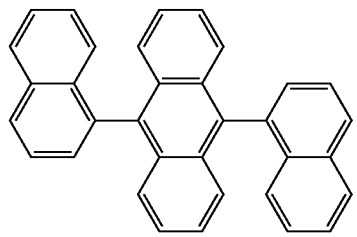
H1

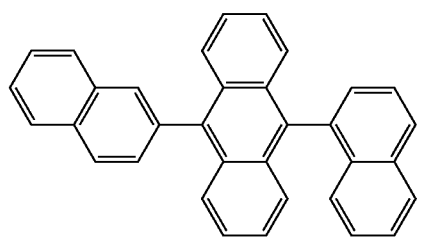
H2

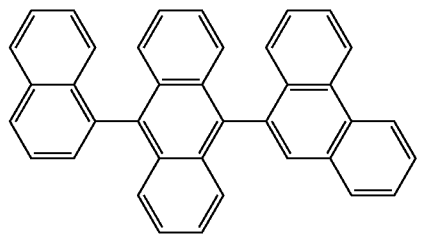
H3

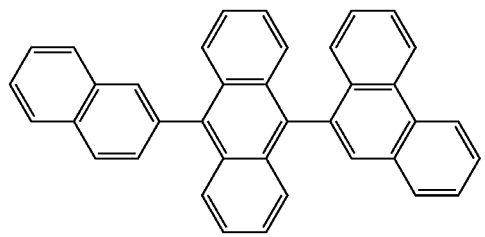
H4

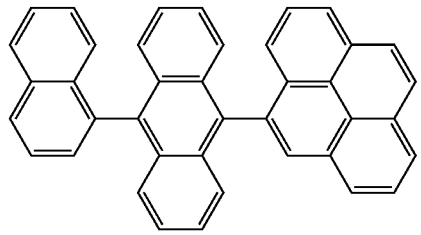
H5

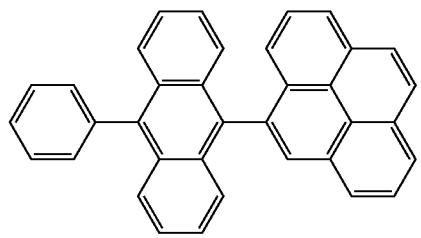
H6

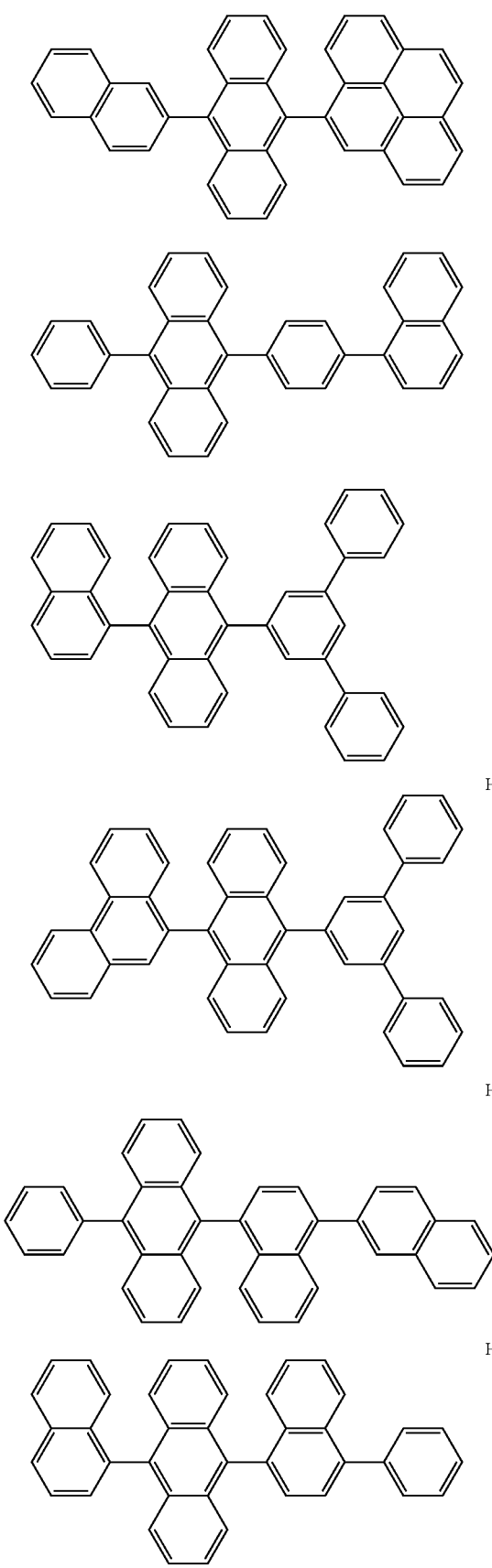

-continued
H18
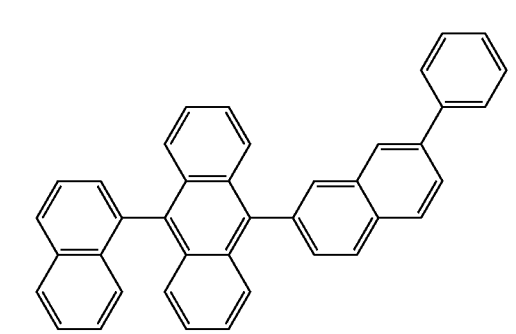
H19
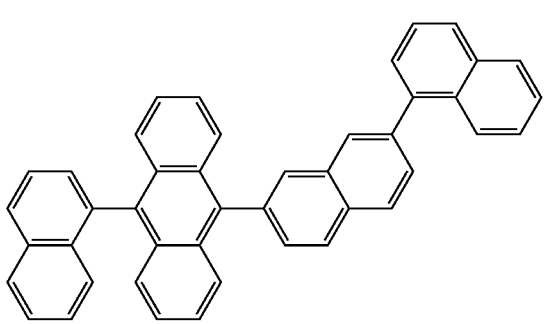
H20
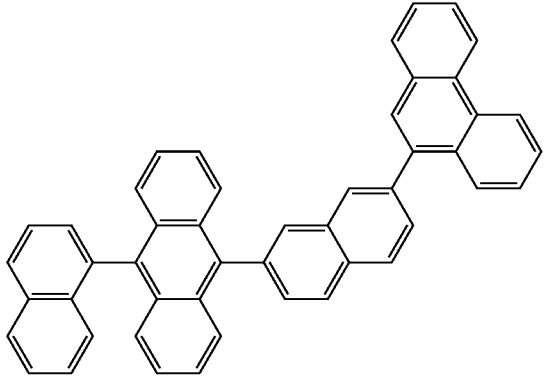
H21
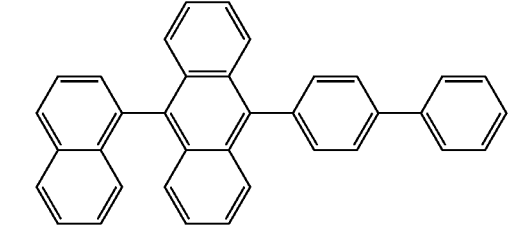
H22
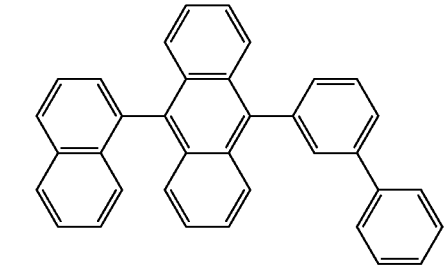
-continued
H23
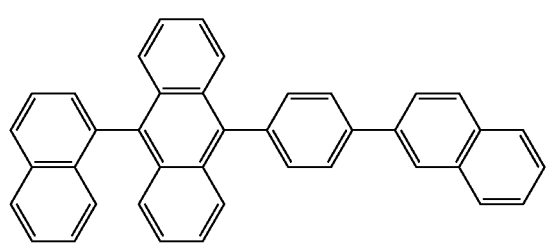
H24
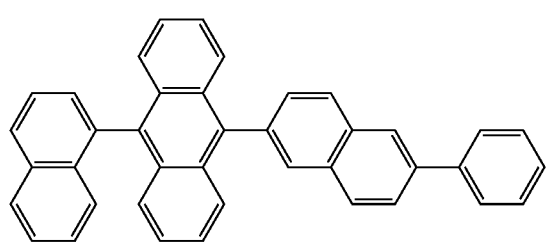
H25
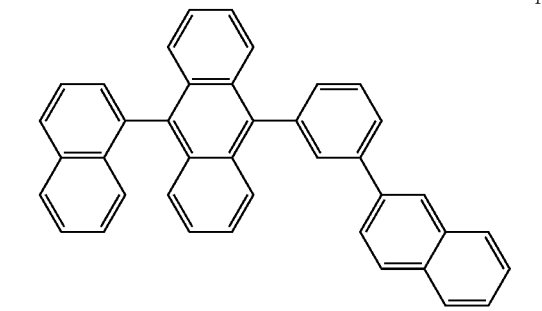
H26
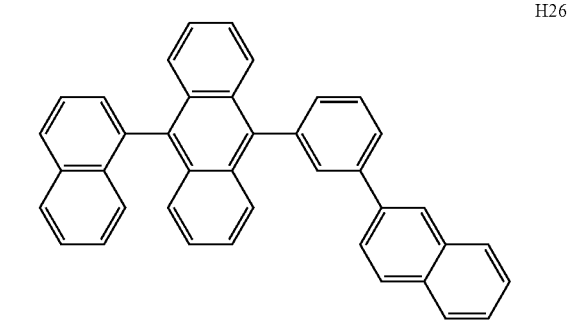
H27
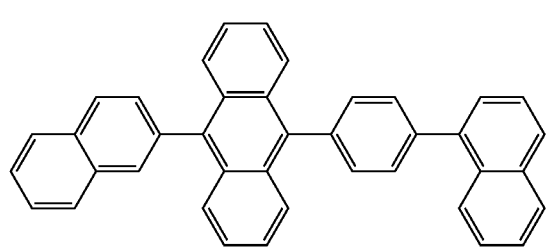

-continued
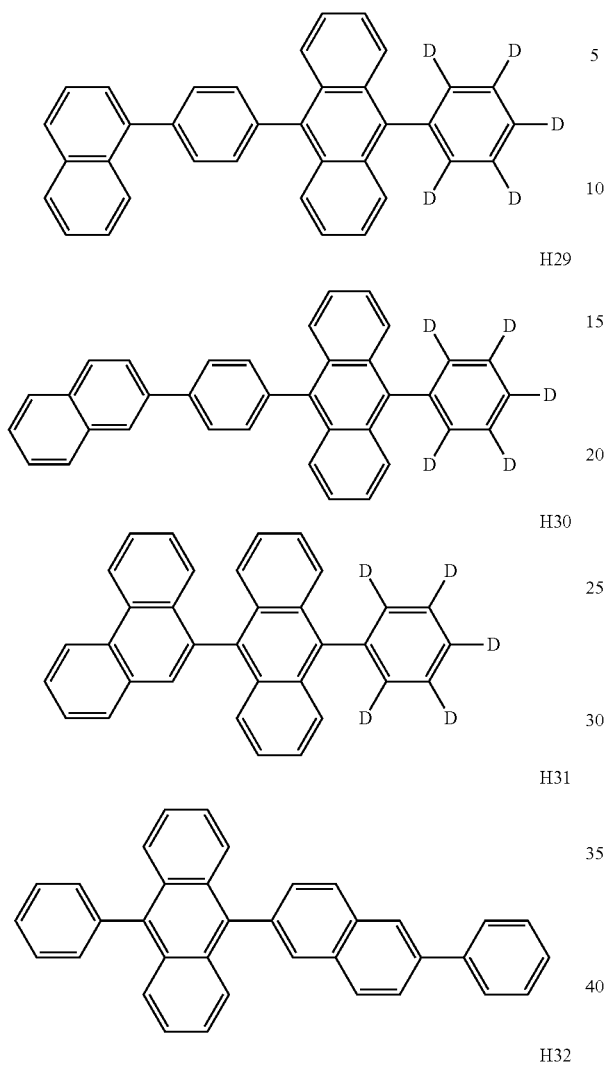
-continued
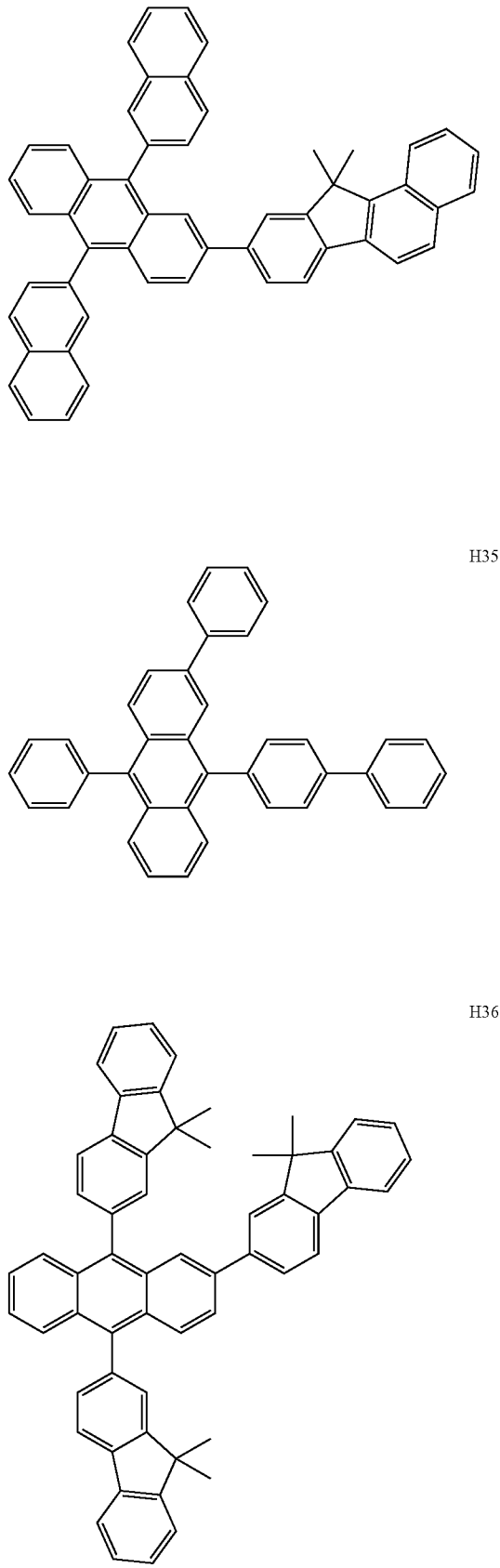

H37
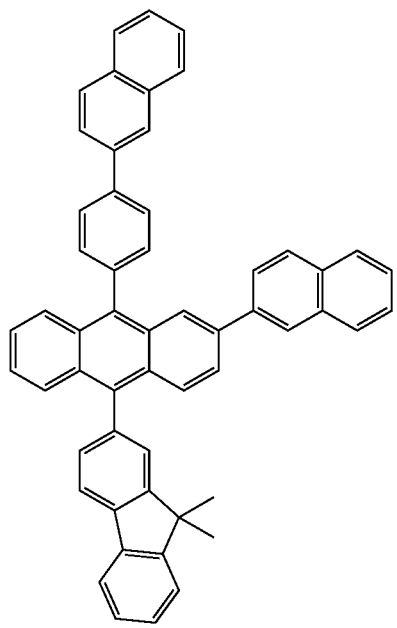
H38
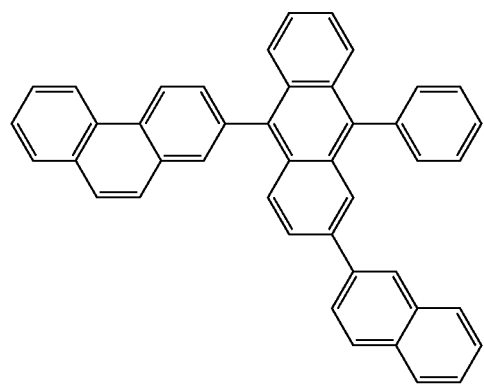
H39
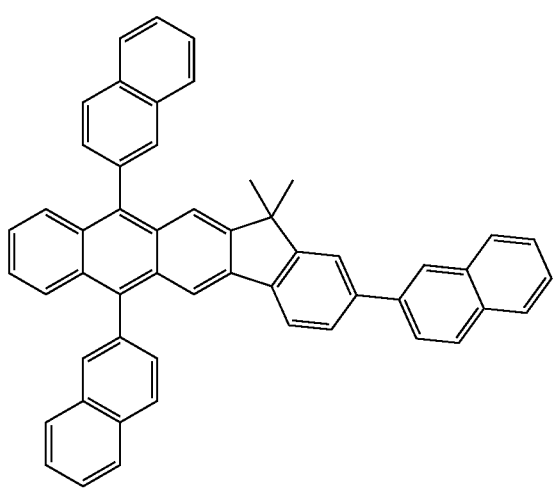
H40
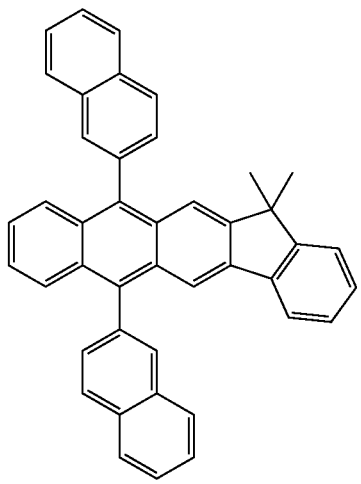
H41
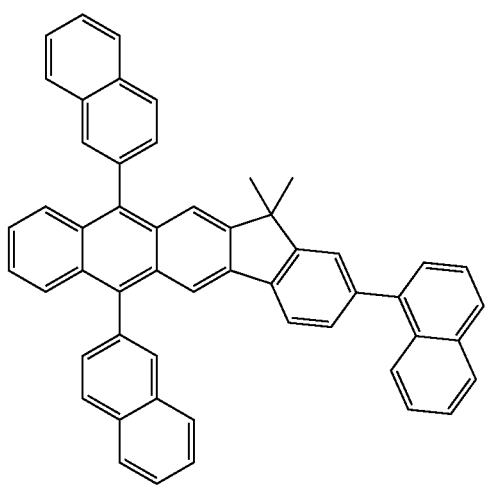
H42
When the OLED is a full color OLED, the EML may be patterned into a red EML, a green EML, and a blue EML. Alternatively, the OLED may have various structural variations, for example, the EML may have a stacked structure of a red EML, a green EML, and/or a blue EML, to emit white light.

When the EML includes a host and a dopant, an amount of the dopant may be, in general, in a range of about 0.01 to about 15 parts by weight based on 100 parts by weight of the host, but is not limited thereto.

A thickness of the EML may be in a range of about 100 Å to about 1,000 Å, for example, about 200 Å to about 600 Å. When thickness of the EML is within this range, excellent light-emission characteristics may be obtained without a substantial increase in driving voltage.

Then, an electron transport region may be disposed on the EML.

The electron transport region may include at least one layer selected from a hole blocking layer, an electron transport layer, and an electron injection layer.

For example, the electron transport region may have a structure of hole blocking layer/electron transport layer/electron injection layer, or a structure of electron transport layer/electron injection layer, but is not limited thereto. The electron transport layer may have a single-layer structure or a multi-layer structure including two or more layers that are different from each other.

Conditions for forming a hole blocking layer, an electron transport layer, and an electron injection layer, which are included in the electron transport region, may be understood by referring to the conditions for forming an HIL.

When the electron transport region includes a hole blocking layer, the hole blocking layer may include, for example, at least one of BCP and Bphen below, but is not limited thereto.

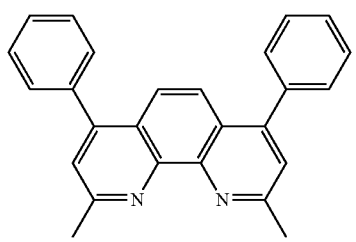

BCP

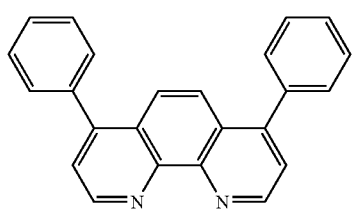

Bphen

A thickness of the hole blocking layer may be in a range of about 20 Å to about 1,000 Å, for example, about 30 Å to about 300 Å. When the thickness of the hole blocking layer is within these ranges, the hole blocking layer may have excellent hole blocking characteristics without a substantial increase in driving voltage.

The electron transport layer may further include at least one compound selected from BCP, Bphen, and Alq3, Balq, TAZ, and NTAZ, which are illustrated below.

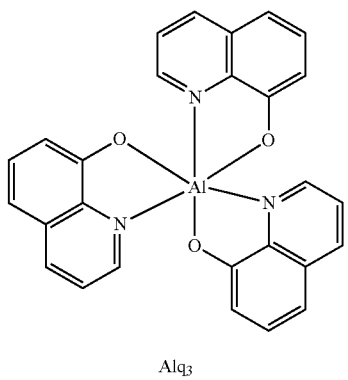

Alq3

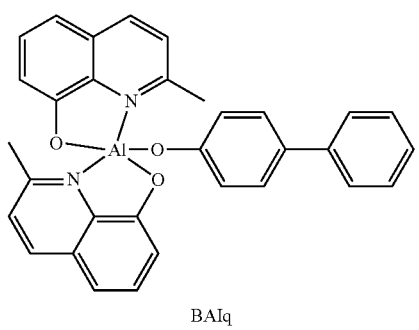

BAlq

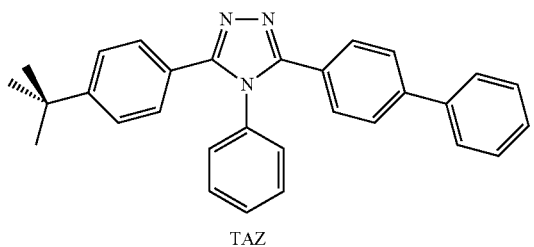

TAZ

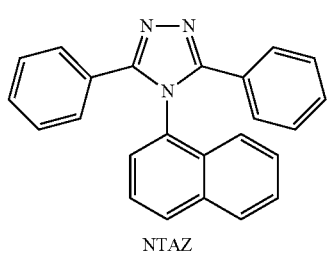

NTAZ

Alternatively, the electron transport layer may include at least one of Compounds ET1 and ET2 illustrated below, but is not limited thereto.

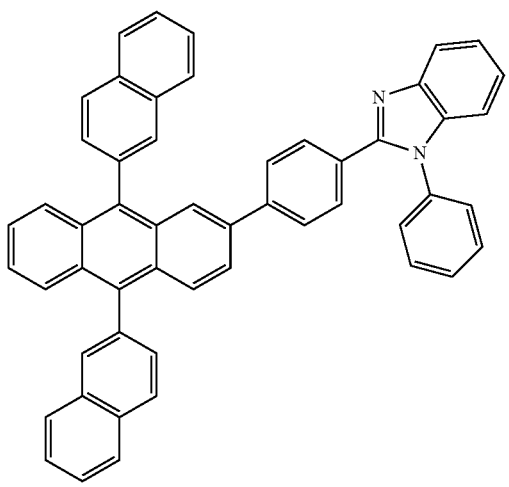

ET1

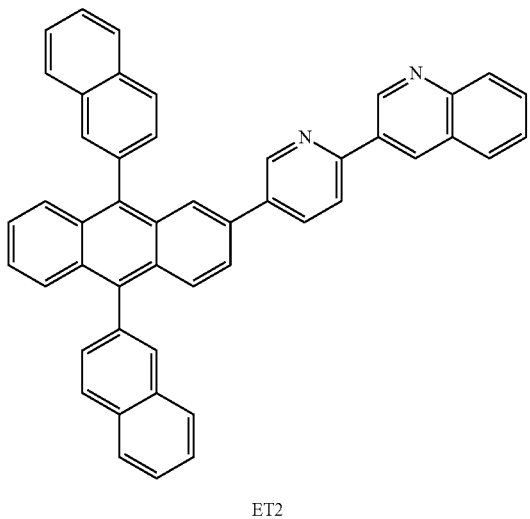

ET2

A thickness of the electron transport layer may be in a range of about 100 Å to about 1,000 Å, for example, about 150 Å to about 500 Å. When the thickness of the electron transport layer is within the range described above, the electron transport layer may have satisfactory electron transporting characteristics without a substantial increase in driving voltage.

The electron transport layer may further include, in addition to the materials described above, a metal-containing material.

The metal-containing material may include a Li complex. The Li complex may include, for example, Compound ET-D1 (lithium quinolate, LiQ) or ET-D2.

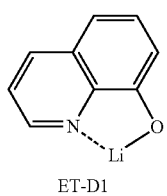

ET-D1

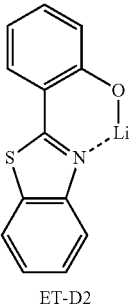

ET-D2

In addition, the electron transport region may include an electron injection layer (EIL) that allows electrons to be easily provided from the second electrode 19.

The EIL may include at least one compound selected from LiF, NaCl, a CsF, $Li_2O$, and BaO.

A thickness of the EIL may be in a range of about 1 Å to about 100 Å, for example, about 3 Å to about 90 Å. When the thickness of the electron injection layer is within the range described above, the electron injection layer may have satisfactory electron injection characteristics without a substantial increase in driving voltage.

The second electrode 19 is disposed on the organic layer 15. The second electrode 19 may be a cathode. In this regard, a material for forming the second electrode 19 may be a material having a low work function, and such a material may be metal, alloy, an electrically conductive compound, or a combination thereof. Detailed examples of the material for forming the second electrode 19 are lithium (Li), magnesium (Mg), aluminum (Al), aluminum-lithium (Al—Li), calcium (Ca), magnesium-indium (Mg—In), or magnesium-silver (Mg—Ag). Alternatively, to obtain a top-emitting device, the OLED may have various structural variations, and for example, ITO or IZO may be used to form a reflective electrode.

Hereinbefore, the OLED has been described with reference to FIG. 1, but is not limited thereto.

A $C_1$-$C_{60}$ alkyl group used herein refers to a linear or branched aliphatic hydrocarbon monovalent group having 1 to 60 carbon atoms. Detailed examples thereof are a methyl group, an ethyl group, a propyl group, an isobutyl group, a sec-butyl group, a tert-butyl group, a pentyl group, an iso-amyl group, and a hexyl group. A $C_1$-$C_{60}$ alkylene group used herein refers to a divalent group having the same structure as the $C_1$-$C_{60}$ alkyl group.

A $C_1$-$C_{60}$ alkoxy group used herein refers to a monovalent group represented by —$OA_{101}$ (wherein $A_{101}$ is the $C_1$-$C_{60}$ alkyl group). Detailed examples thereof are a methoxy group, an ethoxy group, and an isopropyloxy group.

A $C_2$-$C_{60}$ alkenyl group used herein refers to a hydrocarbon group formed by substituting at least one carbon double bond in the middle or at the terminal of the C2-C60 alkyl group. Detailed examples thereof are an ethenyl group, a propenyl group and a butenyl group. A $C_2$-$C_{60}$ alkenylene group used herein refers to a divalent group having the same structure as the $C_2$-$C_{60}$ alkenyl group.

A $C_2$-$C_{60}$ alkynyl group used herein refers to a hydrocarbon group formed by substituting at least one carbon triple bond in the middle or at the terminal of the $C_2$-$C_{60}$ alkyl group. Detailed examples thereof are an ethynyl group and a propynyl group. A $C_2$-$C_{60}$ alkynylene group used herein refers to a divalent group having the same structure as the $C_2$-$C_{60}$ alkynyl group.

A $C_3$-$C_{10}$ cycloalkyl group used herein refers to a monovalent hydrocarbon monocyclic group having 3 to 10 carbon atoms. Detailed examples thereof are a cyclopropyl group, a cyclobutyl group, a cyclopentyl group, a cyclohexyl group, and a cycloheptyl group. A $C_3$-$C_{10}$ cycloalkylene group used herein refers to a divalent group having the same structure as the $C_3$-$C_{10}$ cycloalkyl group.

A $C_3$-$C_{10}$ heterocycloalkyl group used herein refers to a monovalent monocyclic group having at least one heteroatom selected from N, O, P, and S as a ring-forming atom and 3 to 10 carbon atoms. Detailed examples thereof are a tetrahydrofuranyl group and a tetrahydrothiophenyl group. A $C_3$-$C_{10}$ heterocycloalkylene group used herein refers to a divalent group having the same structure as the $C_3$-$C_{10}$ heterocycloalkyl group.

A $C_3$-$C_{10}$ cycloalkenyl group used herein refers to a monovalent monocyclic group that has 3 to 10 carbon atoms and at least one double bond in the ring thereof and does not have aromaticity. Detailed examples thereof are a cyclopentenyl group, a cyclohexenyl group, and a cycloheptenyl group. A $C_3$-$C_{10}$ cycloalkenylene group used herein refers to a divalent group having the same structure as the $C_3$-$C_{10}$ cycloalkenyl group.

A $C_2$-$C_{10}$ heterocycloalkenyl group used herein refers to a monovalent monocyclic group that has at least one heteroatom selected from N, O, P, and S as a ring-forming atom, 2 to 10 carbon atoms, and at least one double bond in its ring. Detailed examples of the $C_3$-$C_{10}$ heterocycloalkenyl group are a 2,3-dihydrofuranyl group and a 2,3-dihydrothiophenyl group. A $C_2$-$C_{10}$ heterocycloalkenylene group used herein refers to a divalent group having the same structure as the $C_2$-$C_{10}$ heterocycloalkenyl group.

A $C_6$-$C_{60}$ aryl group used herein refers to a monovalent group having a carbocyclic aromatic system having 6 to 60 carbon atoms, and a $C_6$-$C_{60}$ arylene group used herein refers to a divalent group having a carbocyclic aromatic system having 6 to 60 carbon atoms. Detailed examples of the $C_6$-$C_{60}$ aryl group are a phenyl group, a naphthyl group, an anthracenyl group, a phenanthrenyl group, a pyrenyl group, and a chrysenyl group. When the $C_6$-$C_{60}$ aryl group and the $C_6$-$C_{60}$ arylene group each include two or more rings, the rings may be fused to each other.

A $C_2$-$C_{60}$ heteroaryl group used herein refers to a monovalent group having a carbocyclic aromatic system that has at least one heteroatom selected from N, O, P, and S as a ring-forming atom, and 2 to 60 carbon atoms. A $C_2$-$C_{60}$ heteroarylene group used herein refers to a divalent group having a carbocyclic aromatic system that has at least one heteroatom selected from N, O, P, and S as a ring-forming atom, and 2 to 60 carbon atoms. Detailed examples of the $C_2$-$C_{60}$ heteroaryl group are a pyridinyl group, a pyrimidinyl group, a pyrazinyl group, a pyridazinyl group, a triazinyl group, a quinolinyl group, and an isoquinolinyl group. When the $C_2$-$C_{60}$ heteroaryl group and the $C_2$-$C_{60}$ heteroarylene group each include two or more rings, the rings may be fused to each other.

A $C_6$-$C_{60}$ aryloxy group used herein indicates —$OA_{102}$ (wherein $A_{102}$ is the $C_6$-$C_{60}$ aryl group), and a $C_6$-$C_{60}$ arylthio group used herein indicates —$SA_{103}$ (wherein $A_{103}$ is the $C_6$-$C_{60}$ aryl group).

A monovalent non-aromatic condensed polycyclic group used herein refers to a monovalent group that has two or more rings condensed to each other, only carbon atoms as a ring-forming atom (for example, having 8 to 60 carbon atoms), wherein the molecular structure as a whole is non-aromatic. A detailed example of the monovalent non-aromatic condensed polycyclic group is a fluorenyl group. A divalent non-aromatic condensed polycyclic group used herein refers to a divalent group having the same structure as the monovalent non-aromatic condensed polycyclic group.

A monovalent non-aromatic condensed heteropolycyclic group used herein refers to a monovalent group that has two or more rings condensed to each other, has a heteroatom selected from N, O P, and S, other than carbon atoms, as a ring forming atom (for example, having 2 to 60 carbon atoms), wherein the molecular structure as a whole is non-aromatic. Detailed examples of the monovalent non-aromatic condensed heteropolycyclic group are a carbazolyl group. A divalent non-aromatic condensed heteropolycyclic group used herein refers to a divalent group having the same structure as the monovalent non-aromatic condensed heteropolycyclic group.

At least one substituent of the substituted $C_1$-$C_{60}$ alkyl group, the substituted $C_2$-$C_{60}$ alkenyl group, the substituted $C_2$-$C_{60}$ alkynyl group, the substituted $C_1$-$C_{60}$ alkoxy group, the substituted $C_3$-$C_{10}$ cycloalkyl group, the substituted $C_2$-$C_{10}$ heterocycloalkyl group, the substituted $C_3$-$C_{10}$ cycloalkenyl group, the substituted $C_2$-$C_{10}$ heterocycloalkenyl group, the substituted $C_6$-$C_{60}$ aryl group, the substituted $C_6$-$C_{60}$ aryloxy group, the substituted $C_6$-$C_{60}$ arylthio group, the substituted $C_2$-$C_{60}$ heteroaryl group, the substituted monovalent non-aromatic condensed polycyclic group, and the substituted monovalent non-aromatic condensed heteropolycyclic group may be a deuterium, —F, —Cl, —Br, —I, a hydroxyl group, a cyano group, a nitro group, an amino group, an amidino group, a hydrazine group, a hydrazone group, a carboxylic acid and a salt thereof, a sulfonic acid and a salt thereof, a phosphoric acid and a salt thereof, a $C_1$-$C_{60}$ alkyl group, a $C_2$-$C_{60}$ alkenyl group, a $C_2$-$C_{60}$ alkynyl group, or a $C_1$-$C_{60}$ alkoxy group;

a $C_1$-$C_{60}$ alkyl group, a $C_2$-$C_{60}$ alkenyl group, a $C_2$-$C_{60}$ alkynyl group, or a $C_1$-$C_{60}$ alkoxy group, each substituted with at least one group selected from a deuterium, —F, —Cl, —Br, —I, a hydroxyl group, a cyano group, a nitro group, an amino group, an amidino group, a hydrazine group, a hydrazone group, a carboxylic acid and a salt thereof, a sulfonic acid and a salt thereof, a phosphoric acid and a salt thereof, a $C_3$-$C_{10}$ cycloalkyl group, a $C_2$-$C_{10}$ heterocycloalkyl group, a $C_3$-$C_{10}$ cycloalkenyl group, a $C_2$-$C_{10}$ heterocycloalkenyl group, a $C_6$-$C_{60}$ aryl group, a $C_6$-$C_{60}$ aryloxy group, a $C_6$-$C_{60}$ arylthio group, a $C_2$-$C_{60}$ heteroaryl group, a monovalent non-aromatic condensed polycyclic group, a monovalent non-aromatic condensed heteropolycyclic group, —$N(Q_{11})(Q_{12})$, —$Si(Q_{13})(Q_{14})(Q_{15})$, and —$B(Q_{16})(Q_{17})$;

a $C_3$-$C_{10}$ cycloalkyl group, a $C_2$-$C_{10}$ heterocycloalkyl group, a $C_3$-$C_{10}$ cycloalkenyl group, a $C_2$-$C_{10}$ heterocycloalkenyl group, a $C_6$-$C_{60}$ aryl group, a $C_6$-$C_{60}$ aryloxy group, a $C_6$-$C_{60}$ arylthio group, a $C_2$-$C_{60}$ heteroaryl group, a monovalent non-aromatic condensed polycyclic group, or a monovalent non-aromatic condensed heteropolycyclic group;

a $C_3$-$C_{10}$ cycloalkyl group, a $C_2$-$C_{10}$ heterocycloalkyl group, a $C_3$-$C_{10}$ cycloalkenyl group, a $C_2$-$C_{10}$ heterocycloalkenyl group, a $C_6$-$C_{60}$ aryl group, a $C_6$-$C_{60}$ aryloxy group, a $C_6$-$C_{60}$ arylthio group, a $C_2$-$C_{60}$ heteroaryl group, a monovalent non-aromatic condensed polycyclic group, or a monovalent non-aromatic condensed heteropolycyclic group, each substituted with at least one group selected from a deuterium, —F, —Cl, —Br, —I, a hydroxyl group, a cyano group, a nitro group, an amino group, an amidino group, a hydrazine group, a hydrazone group, a carboxylic acid and a salt thereof, a sulfonic acid and a salt thereof, a phosphoric acid and a salt thereof, a $C_1$-$C_{60}$ alkyl group, a $C_2$-$C_{60}$ alkenyl group, a $C_2$-$C_{60}$ alkynyl group, a $C_1$-$C_{60}$ alkoxy group, a $C_3$-$C_{10}$ cycloalkyl group, a $C_2$-$C_{10}$ heterocycloalkyl group, a $C_3$-$C_{10}$ cycloalkenyl group, a $C_2$-$C_{10}$ heterocycloalkenyl group, a $C_6$-$C_{60}$ aryl group, a $C_6$-$C_{60}$ aryloxy group, a $C_6$-$C_{60}$ arylthio group, a $C_2$-$C_{60}$ heteroaryl group, a monovalent non-aromatic condensed polycyclic group, a monovalent non-aromatic condensed heteropolycyclic group, —N($Q_{21}$)($Q_{22}$), —Si($Q_{23}$)($Q_{24}$)($Q_{25}$), and —B($Q_{26}$)($Q_{27}$); or
—N($Q_{31}$)($Q_{32}$), —Si($Q_{33}$)($Q_{34}$)($Q_{35}$), or —B($Q_{36}$)($Q_{37}$); and wherein $Q_1$ to $Q_7$, $Q_{11}$ to $Q_{17}$, $Q_{21}$ to $Q_{27}$, and $Q_{31}$ to $Q_{37}$ may be each independently selected from a hydrogen, a deuterium, —F, —Cl, —Br, —I, a hydroxyl group, a cyano group, a nitro group, an amino group, an amidino group, a hydrazine group, a hydrazone group, a carboxylic acid and a salt thereof, a sulfonic acid and a salt thereof, a phosphoric acid and a salt thereof, a $C_1$-$C_{60}$ alkyl group, a $C_2$-$C_{60}$ alkenyl group, a $C_2$-$C_{60}$ alkynyl group, a $C_1$-$C_{60}$ alkoxy group, a $C_3$-$C_{10}$ cycloalkyl group, a $C_2$-$C_{10}$ heterocycloalkyl group, a $C_3$-$C_{10}$ cycloalkenyl group, a $C_2$-$C_{10}$ heterocycloalkenyl group, a $C_6$-$C_{60}$ aryl group, a $C_6$-$C_{60}$ aryloxy group, a $C_6$-$C_{60}$ arylthio group, a $C_2$-$C_{60}$ heteroaryl group, a monovalent non-aromatic condensed polycyclic group; or a monovalent non-aromatic condensed heteropolycyclic group.

For example, at least one substituent of the substituted $C_1$-$C_{60}$ alkyl group, the substituted $C_2$-$C_{60}$ alkenyl group, the substituted $C_2$-$C_{60}$ alkynyl group, the substituted $C_1$-$C_{60}$ alkoxy group, the substituted $C_3$-$C_{10}$ cycloalkyl group, the substituted $C_2$-$C_{10}$ heterocycloalkyl group, the substituted $C_3$-$C_{10}$ cycloalkenyl group, the substituted $C_2$-$C_{10}$ heterocycloalkenyl group, the substituted $C_6$-$C_{60}$ aryl group, the substituted $C_6$-$C_{60}$ aryloxy group, the substituted $C_6$-$C_{60}$ arylthio group, the substituted $C_2$-$C_{60}$ heteroaryl group, the substituted monovalent non-aromatic condensed polycyclic group, and the substituted monovalent non-aromatic condensed heteropolycyclic group may be a deuterium, —F, —Cl, —Br, —I, a hydroxyl group, a cyano group, a nitro group, an amino group, an amidino group, a hydrazine group, a hydrazone group, a carboxylic acid and a salt thereof, a sulfonic acid and a salt thereof, a phosphoric acid and a salt thereof, a $C_1$-$C_{60}$ alkyl group, a $C_2$-$C_{60}$ alkenyl group, a $C_2$-$C_{60}$ alkynyl group, or a $C_1$-$C_{60}$ alkoxy group;

a $C_1$-$C_{60}$ alkyl group, a $C_2$-$C_{60}$ alkenyl group, a $C_2$-$C_{60}$ alkynyl group, or a $C_1$-$C_{60}$ alkoxy group, each substituted with at least one of a deuterium, —F, —Cl, —Br, —I, a hydroxyl group, a cyano group, a nitro group, an amino group, an amidino group, a hydrazine group, a hydrazone group, a carboxylic acid and a salt thereof, a sulfonic acid and a salt thereof, a phosphoric acid and a salt thereof, a phenyl group, a pentalenyl group, an indenyl group, a naphthyl group, an azulenyl group, a heptalenyl group, an indacenyl group, an acenaphthyl group, a fluorenyl group, a spiro-fluorenyl group, a benzofluorenyl group, a dibenzofluorenyl group, a phenalenyl group, a phenanthrenyl group, an anthracenyl group, a fluoranthrenyl group, a triphenylenyl group, a pyrenyl group, a chrysenyl group, a naphthacenyl group, a picenyl group, a perylenyl group, a pentaphenyl group, a hexacenyl group, a pentacenyl group, a rubicenyl group, a coronenyl group, an ovalenyl group, a pyrrolyl group, a thiophenyl group, a furanyl group, an imidazolyl group, a pyrazolyl group, a thiazolyl group, an isothiazolyl group, an oxazolyl group, an isooxazolyl group, a pyridinyl group, a pyrazinyl group, a pyrimidinyl group, a pyridazinyl group, an isoindolyl group, an indolyl group, an indazolyl group, a purinyl group, a quinolinyl group, an isoquinolinyl group, a benzoquinolinyl group, a phthalazinyl group, a naphthyridinyl group, a quinoxalinyl group, a quinazolinyl group, a cinnolinyl group, a carbazolyl group, a phenanthridinyl group, an acridinyl group, a phenanthrolinyl group, a phenazinyl group, a benzoimidazolyl group, a benzofuranyl group, a benzothiophenyl group, an isobenzothiazolyl group, a benzooxazolyl group, an isobenzooxazolyl group, a triazolyl group, a tetrazolyl group, an oxadiazolyl group, a triazinyl group, a dibenzofuranyl group, a dibenzothiophenyl group, a benzocarbazolyl group, a dibenzocarbazolyl group, an imidazopyridinyl group, an imidazopyrimidinyl group, —N($Q_{11}$)($Q_{12}$), —Si($Q_{13}$)($Q_{14}$)($Q_{15}$), and —B($Q_{16}$)($Q_{17}$);

a phenyl group, a pentalenyl group, an indenyl group, a naphthyl group, an azulenyl group, a heptalenyl group, an indacenyl group, an acenaphthyl group, a fluorenyl group, a spiro-fluorenyl group, a benzofluorenyl group, a dibenzofluorenyl group, a phenalenyl group, a phenanthrenyl group, an anthracenyl group, a fluoranthrenyl group, a triphenylenyl group, a pyrenyl group, a chrysenyl group, a naphthacenyl group, a picenyl group, a perylenyl group, a pentaphenyl group, a hexacenyl group, a pentacenyl group, a rubicenyl group, a coronenyl group, an ovalenyl group, a pyrrolyl group, a thiophenyl group, a furanyl group, an imidazolyl group, a pyrazolyl group, a thiazolyl group, an isothiazolyl group, an oxazolyl group, an isooxazolyl group, a pyridinyl group, a pyrazinyl group, a pyrimidinyl group, a pyridazinyl group, an isoindolyl group, an indolyl group, an indazolyl group, a purinyl group, a quinolinyl group, an isoquinolinyl group, a benzoquinolinyl group, a phthalazinyl group, a naphthyridinyl group, a quinoxalinyl group, a quinazolinyl group, a cinnolinyl group, a carbazolyl group, a phenanthridinyl group, an acridinyl group, a phenanthrolinyl group, a phenazinyl group, a benzoimidazolyl group, a benzofuranyl group, a benzothiophenyl group, an isobenzothiazolyl group, a benzooxazolyl group, an isobenzooxazolyl group, a triazolyl group, a tetrazolyl group, an oxadiazolyl group, a triazinyl group, a dibenzofuranyl group, a dibenzothiophenyl group, a benzocarbazolyl group, a dibenzocarbazolyl group, an imidazopyridinyl group, or an imidazopyrimidinyl group;

a phenyl group, a pentalenyl group, an indenyl group, a naphthyl group, an azulenyl group, a heptalenyl group, an indacenyl group, an acenaphthyl group, a fluorenyl group, a spiro-fluorenyl group, a benzofluorenyl group, a dibenzofluorenyl group, a phenalenyl group, a phenanthrenyl group, an anthracenyl group, a fluoranthrenyl group, a triphenylenyl group, a pyrenyl group, a chrysenyl group, a naphthacenyl group, a picenyl group, a perylenyl group, a pentaphenyl group, a hexacenyl group, a pentacenyl group, a rubicenyl group, a coronenyl group, an ovalenyl group, a pyrrolyl group, a thiophenyl group, a furanyl group, an imidazolyl group, a pyrazolyl group, a thiazolyl group, an isothiazolyl group, an oxazolyl group, an isooxazolyl group, a pyridinyl group, a pyrazinyl group, a pyrimidinyl group, a pyridazinyl group, an isoindolyl group, an indolyl group, an indazolyl group, a purinyl group, a quinolinyl group, an isoquinolinyl group, a benzoquinolinyl group, a phthalazinyl group, a naphthyridinyl group, a quinoxalinyl group, a quinazolinyl group, a cinnolinyl group, a carbazolyl group, a phenanthridinyl group, an acridinyl group, a phenanthrolinyl group, a phenazinyl group, a benzoimidazolyl group, a benzofuranyl group, a benzothiophenyl group, an isobenzothiazolyl group, a benzooxazolyl group, an isobenzooxazolyl group, a triazolyl group, a tetrazolyl group, an oxadiazolyl group, a triazinyl group, a dibenzofuranyl group, a dibenzothiophenyl group, a benzocarbazolyl group, a dibenzocarbazolyl group, an imidazopyridinyl group, or an imidazopyrimidinyl group, each substituted with at least one of a deuterium, —F, —Cl, —Br, —I, a hydroxyl group, a cyano group, a nitro group, an amino group, an amidino group, a hydrazine group, a hydrazone group, a carboxylic acid and a salt thereof, a sulfonic acid and a salt thereof, a phosphoric acid and a salt thereof, a $C_1$-$C_{60}$ alkyl group, a $C_2$-$C_{60}$ alkenyl group, a $C_2$-$C_{60}$ alkynyl group, a $C_1$-$C_{60}$ alkoxy group, a phenyl group, a pentalenyl group, an indenyl group, a naphthyl group, an azulenyl group, a heptalenyl group, an indacenyl group, an acenaphthyl group, a fluorenyl group, a spiro-fluorenyl group, a benzofluorenyl group, a dibenzo-fluorenyl group, a phenalenyl group, a phenanthrenyl group, an anthracenyl group, a fluoranthrenyl group, a triphenylenyl group, a pyrenyl group, a chrysenyl group, a naphthacenyl group, a picenyl group, a perylenyl group, a pentaphenyl group, a hexacenyl group, a pentacenyl group, a rubicenyl group, a coronenyl group, an ovalenyl group, a pyrrolyl group, a thiophenyl group, a furanyl group, an imidazolyl group, a pyrazolyl group, a thiazolyl group, an isothiazolyl group, an oxazolyl group, an isooxazolyl group, a pyridinyl group, a pyrazinyl group, a pyrimidinyl group, a pyridazinyl group, an isoindolyl group, an indolyl group, an indazolyl group, a purinyl group, a quinolinyl group, an isoquinolinyl group, a benzoquinolinyl group, a phthalazinyl group, a naphthyridinyl group, a quinoxalinyl group, a quinazolinyl group, a cinnolinyl group, a carbazolyl group, a phenanthridinyl group, an acridinyl group, a phenanthrolinyl group, a phenazinyl group, a benzoimidazolyl group, a benzofuranyl group, a benzothiophenyl group, an isobenzothiazolyl group, a benzooxazolyl group, an isobenzooxazolyl group, a triazolyl group, a tetrazolyl group, an oxadiazolyl group, a triazinyl group, a dibenzofuranyl group, a dibenzothiophenyl group, a benzocarbazolyl group, a dibenzocarbazolyl group, an imidazopyridinyl group, an imidazopyrimidinyl group, —$N(Q_{21})(Q_{22})$, —$Si(Q_{23})(Q_{24})(Q_{25})$, and —$B(Q_{26})(Q_{27})$; or —$N(Q_{31})(Q_{32})$, —$Si(Q_{33})(Q_{34})(Q_{35})$, or —$B(Q_{36})(Q_{37})$; and wherein $Q_1$ to $Q_7$, $Q_{11}$ to $Q_{17}$, $Q_{21}$ to $Q_{27}$, and $Q_{31}$ to $Q_{37}$ may be each independently selected from a hydrogen, a deuterium, —F, —Cl, —Br, —I, a hydroxyl group, a cyano group, a nitro group, an amino group, an amidino group, a hydrazine group, a hydrazone group, a carboxylic acid and a salt thereof, a sulfonic acid and a salt thereof, a phosphoric acid and a salt thereof, a $C_1$-$C_{60}$ alkyl group, a $C_2$-$C_{60}$ alkenyl group, a $C_2$-$C_{60}$ alkynyl group, a $C_1$-$C_{60}$ alkoxy group, a phenyl group, a pentalenyl group, an indenyl group, a naphthyl group, an azulenyl group, a heptalenyl group, an indacenyl group, an acenaphthyl group, a fluorenyl group, a spiro-fluorenyl group, a benzofluorenyl group, a dibenzo-fluorenyl group, a phenalenyl group, a phenanthrenyl group, an anthracenyl group, a fluoranthrenyl group, a triphenylenyl group, a pyrenyl group, a chrysenyl group, a naphthacenyl group, a picenyl group, a perylenyl group, a pentaphenyl group, a hexacenyl group, a pentacenyl group, a rubicenyl group, a coronenyl group, an ovalenyl group, a pyrrolyl group, a thiophenylene group, a furanylene group, an imidazolyl group, a pyrazolyl group, a thiazolyl group, an isothiazolyl group, an oxazolyl group, an isooxazolyl group, a pyridinyl group, a pyrazinyl group, a pyrimidinyl group, a pyridazinyl group, an isoindolyl group, an indolyl group, an indazolyl group, a purinyl group, a quinolinyl group, an isoquinolinyl group, a benzoquinolinyl group, a phthalazinyl group, a naphthyridinyl group, a quinoxalinyl group, a quinazolinyl group, a cinnolinyl group, a carbazolyl group, a phenanthridinyl group, an acridinyl group, a phenanthrolinyl group, a phenazinyl group, a benzoimidazolyl group, a benzofuranyl group, a benzothiophenyl group, an isobenzothiazolyl group, a benzooxazolyl group, an isobenzooxazolyl group, a triazolyl group, a tetrazolyl group, an oxadiazolyl group, a triazinyl group, a dibenzofuranyl group, a dibenzocarbazolyl group, a benzocarbazolyl group, a dibenzothiophenyl group, an imidazopyridinyl group, or an imidazopyrimidinyl group.

Hereinafter, a compound and an OLED according to an embodiment will be described in detail with reference to Synthesis Examples and Examples, but is not limited to these Synthesis Examples and Examples. The wording "'B' was used instead of 'A'" used in describing Synthesis Examples means that a molar equivalent of 'A' was identical to a molar equivalent of 'B'.

EXAMPLE

Synthesis Example 1: Synthesis of Compound 1

Synthesis of Intermediate A

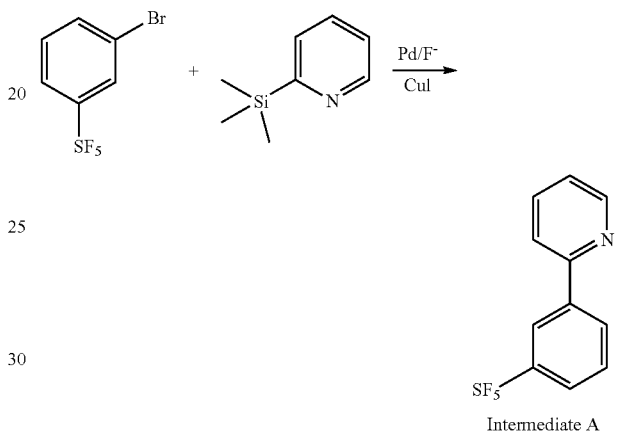

Intermediate A 1 g (0.0035 mol) of 1-bromo-4-(pentafluorosulfanyl)benzene, 0.64 g (0.00424 mol) of trimethylsilyl pyridine, 0.45 g (0.0077 mol) of potassium fluoride, and 0.269 g (0.0014 mol) of CuI were mixed in 20 ml of dried dimethylformamide, and then, the mixture was heated at a temperature of 90° C. for 9 hours in a nitrogen atmosphere. Water was added to the obtained resultant, and extracted by methylene chloride. An organic layer obtained therefrom was dried by using MgSO₄, and then was subjected to column chromatography to obtain 0.59 g of Intermediate A (yield: 60%).

$^1$H NMR (CDCl$_3$, 300 MHz) δ 8.74 (d, J=6 Hz, 1H), 8.45 (t, J=3 Hz, 1H), 8.14 (d, J=3 Hz, 1H) 7.76-7.86 (m, 3H), 7.56 (t, J=9 Hz, 1H) 7.28-7.35 (m, 1H)

M/z (GC-MASS)-282 (MH⁺)

Synthesis of Intermediate B

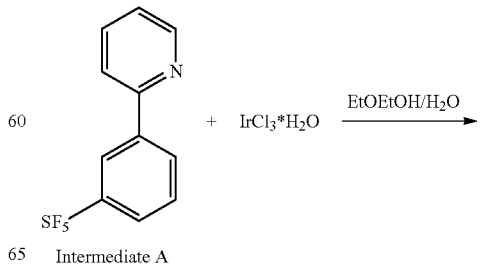

Intermediate A

-continued

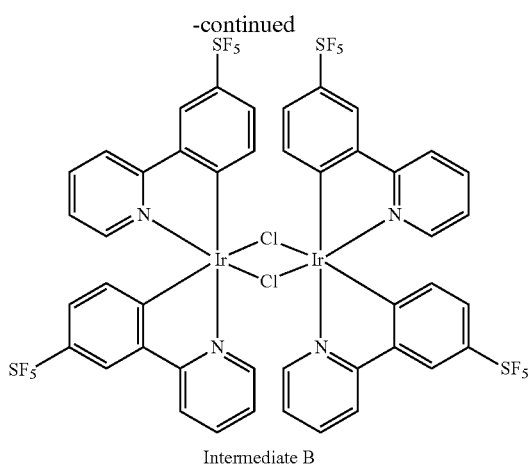

Intermediate B 0.20 g (0.71 mmol) of Intermediate A and 0.135 g (0.36 mmol) of iridium chloride were dissolved in 15 ml of ethoxy ethanol and 5 ml of water. The mixture was then heated at a temperature of 125° C. for 24 hours, and cooled to obtain yellow precipitates. The resultant precipitates were washed out with ethoxy ethanol and water to obtain 0.56 g of Intermediate B (yield: 90%).

$^1$H NMR (CDCl$_3$, 300 MHz) δ 9.75 (d, J=6 Hz, 1H), 9.53 (d, J=6 Hz, 1H), 8.54-8.66 (m, 2H), 8.11-8.22 (m, 4H), 7.61-7.72, (m, 2H), 7.22-7.31 (m, 2H), 6.45 (1H, J=9 Hz, 1H), 5.82 (d, J=9 Hz, 1H)

Synthesis of Compound 1

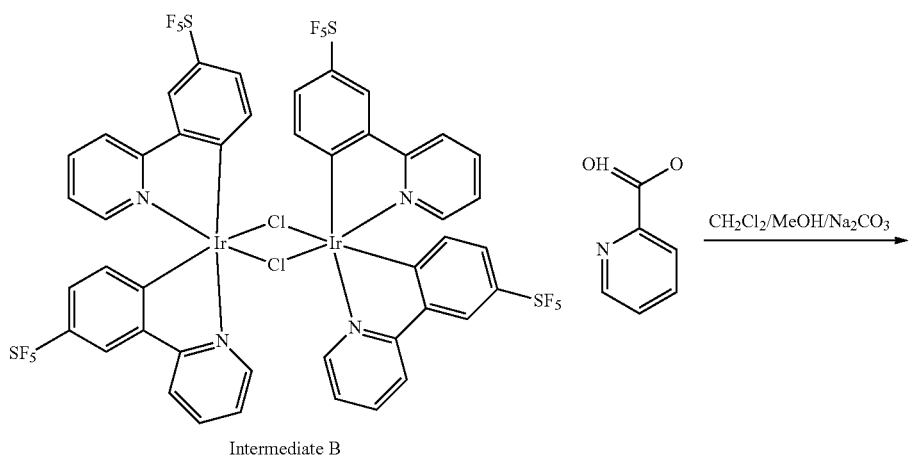

Intermediate B

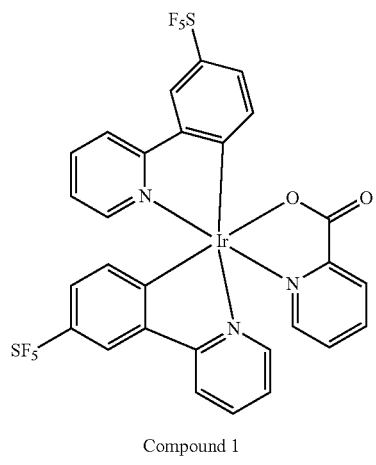

Compound 1

0.027 g (0.017 mmol) of Intermediate B, 0.0047 g (0.037 mmol) of picolinic acid, and 0.03 g of sodium carbonate were dissolved in 10 ml of ethoxy ethanol, and then, the mixture was heated at a temperature of 120° C. overnight. The resultant obtained by cooling the mixture was diluted with methylene chloride three times and washed out with water three times. An organic layer obtained therefrom was dried by using MgSO$_4$, and then was subjected to column chromatography after a solvent was removed therefrom under vacuum, thereby obtain 0.023 g of Compound 1 (yield: 80%).

$^1$H NMR (CDCl3, 300 MHz) δ 8.82 (d, J=3 Hz, 1H), 8.36 (d, J=9 Hz, 1H), 7.75-8.02 (m, 5H), 7.45-7.51 (m, 2H), 7.30 (d, J=6 Hz, 2H) 7.07-7.22 (m, 3H), 6.49 (d, J=3 Hz, 1H) 6.22 (d, J=3 Hz, 1H)

MS (MALDI-TOF) m/z=875 (MH$^+$)

Synthesis Example 2: Synthesis of Compound 2

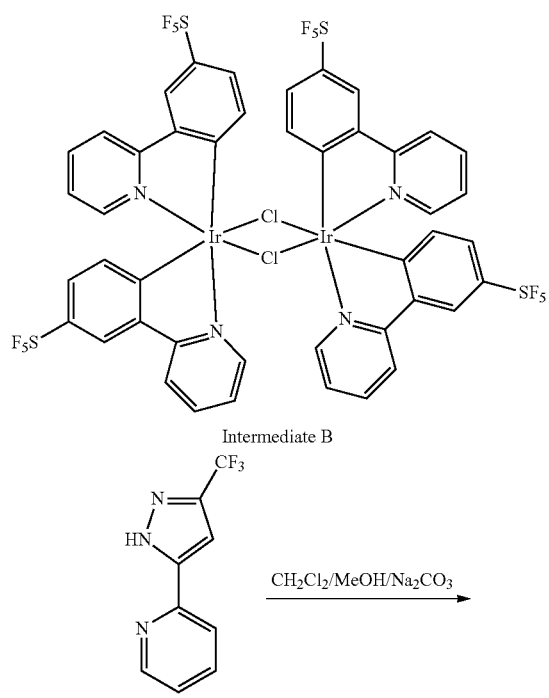

Intermediate B

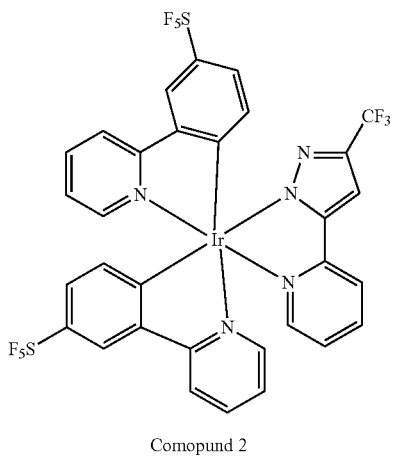

Comopund 2

0.063 g (0.04 mmol) of Intermediate B, 0.0213 g (0.01 mmol) of trifluoropyridinepyrazole, and 0.045 g of sodium carbonate were dissolved in 20 ml of methylene chloride and 1 ml of methanol, and then, the mixture was heated overnight. A solvent was removed from the resultant obtained by cooling the mixture, and the resultant without a solvent was mixed with methylene chloride to be subjected to column chromatography, thereby obtaining 0.057 g of Compound 2 (yield: 75%).

$^1$H NMR (CDCl$_3$, 300 MHz) δ 7.97 (d, J=3 Hz, 1H), 7.90 (M, 3H), 7.68-7.83 (m, 5H), 7.63 (d, J=6 Hz, 1H), 7.57 (d, 3 Hz, 1H), 7.27 (d, 3 Hz, 1H), 7.23 (d, 3 Hz, 1H), 7.15 (d, 3 Hz, 1H), 7.04-7.10 (m, 3H), 6.97-7.01 (m, 2H), 6.36-3.43 (dd, 9 Hz, 2H)

MS (MALDI-TOF) m/z=965 (MH$^+$)

Synthesis Example 3: Synthesis of Compound 3

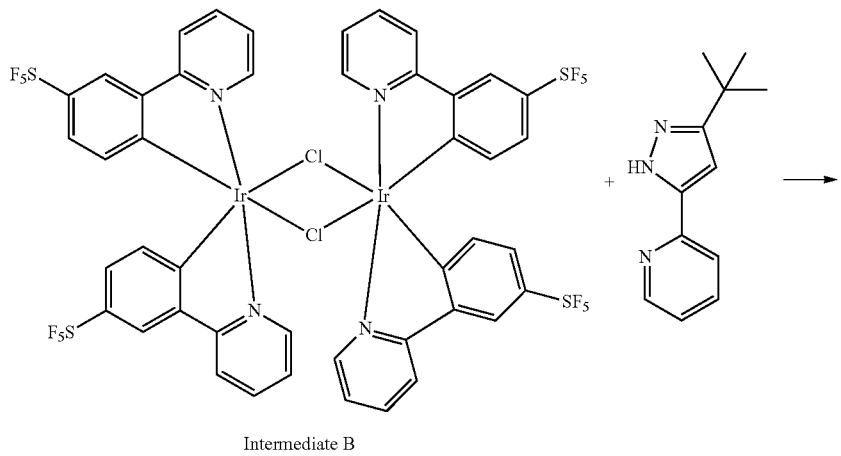

Intermediate B

-continued

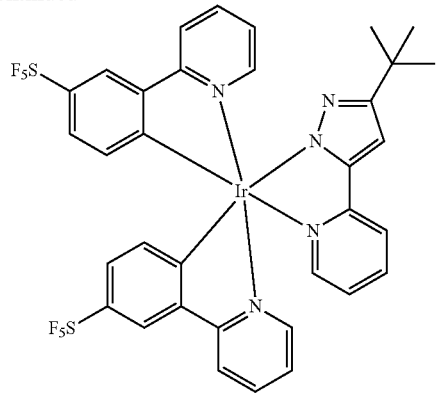

Compound 3

0.063 g (0.04 mmol) of Intermediate B, 0.0201 g (0.01 mmol) of tert-butylpyridinepyrazole, and 0.045 g of sodium carbonate were dissolved in 20 ml of methylene chloride and 1 ml of methanol, and then, the mixture was heated overnight. A solvent was removed from the result obtained by cooling the mixture, and the result without a solvent was mixed with methylene chloride to be subjected to column chromatography, thereby obtaining 0.039 g of Compound 3 (yield: 51%).

$^1$H NMR (CDCl$_3$, 300 MHz) δ 7.96 (d, J=3 Hz, 1H), 7.86-7.90 (m, 3H), 7.71-7.77 (m, 4H), 7.57-7.59 (d, 6 Hz, 2H), 7.50 (d, 6 Hz, 2H), 6.93-7.25 (m, 6H), 6.36-6.42 (t, 2H) 1.51, (s, 9H)

MS (MALDI-TOF) m/z=953 (MH$^+$)

Evaluation Example 1: PL Spectrum Evaluation

Figure 2:
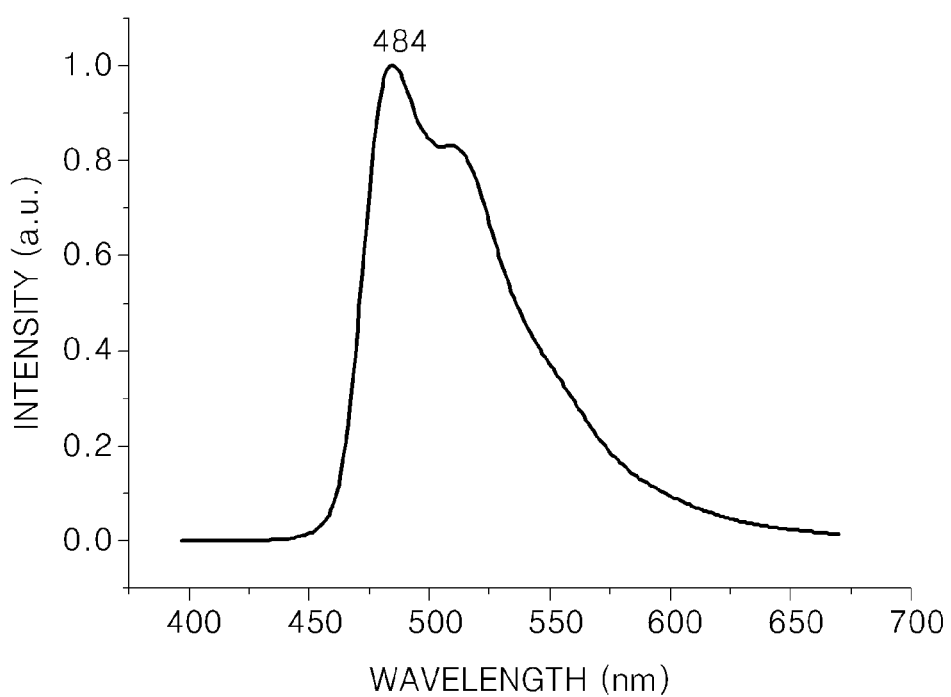
FIGS. 2 and 3 are graphs of intensity (arbitrary unit, a. u.) versus wavelength (nanometer, nm) showing photoluminescent (PL) spectra of Compounds 1 and 2, respectively.
Figure 3:
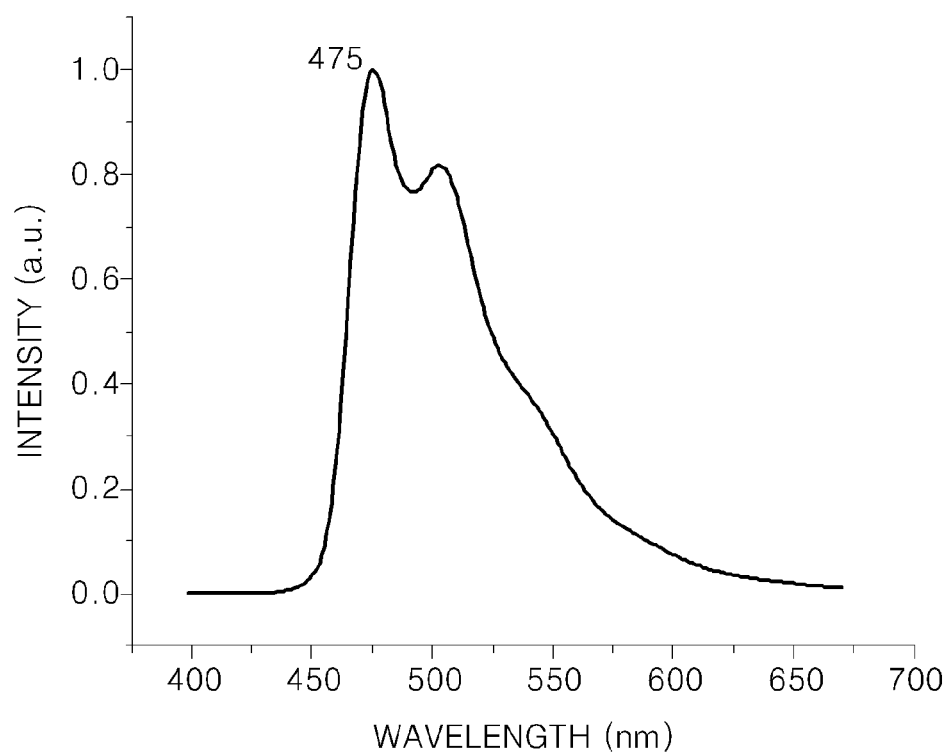

Compound 1 was diluted with toluene to concentration of 10 mM so as to measure in solution photoluminescence (PL) of Compound 1 by using an ISC PC1 spectrofluorometer that is equipped with a Xenon lamp. The same experiment was repeated twice with respect to Compound 2, and the results of PL spectrum evaluated in Compounds 1 and 2 are shown in FIGS. 2 and 3, respectively. Referring to FIGS. 2 and 3, it was confirmed that Compounds 1 and 2 had excellent emission characteristics.

Example 1

A glass substrate including an indium tin oxide (ITO) electrode (a first electrode, an anode) that has a thickness of 1,500 Å was subjected to cleaning process using distilled water and an ultrasonic cleaner. After completing the cleaning using distilled water, the substrate was subjected to ultrasonic cleaning process using a solvent such as isopropyl alcohol, acetone, and methanol. The cleaned substrate was dried and transferred to a plasma cleaner to clean for 5 minutes using an oxygen plasma. The substrate was then transferred to a vacuum evaporator.

2-TNATA was vacuum deposited on the ITO electrode included in the glass substrate to form a HIL having a thickness of 600 Å, NPB was vacuum deposited on the HIL to form a hole transport layer having a thickness of 1,200 Å, thereby forming a hole transport region.

The ADN (host) and Compound 1 (dopant, 7 weight %) were co-deposited on the hole transport region to form an EML having a thickness of 300 Å.

BCP was vacuum deposited on the EML to form a hole blocking layer having a thickness of 50 Å, Alq$_3$ was vacuum deposited on the hole blocking layer to form an electron transport layer having a thickness of 250 Å, LiF was deposited on the electron transport layer to form an electron injection layer having a thickness of 5 Å, and Al was deposited on the electron injection layer to form a second electrode (cathode) having a thickness of 1,000 Å, thereby completing the manufacture of an OLED.

Example 2

An OLED was manufactured in the same manner as in Example 1, except that in forming an EML, Compound 2 was used instead of Compound 1 as a dopant.

Comparative Example 1

An OLED was manufactured in the same manner as in Example 1, except that in forming an EML, Compound A was used instead of Compound 1 as a dopant.

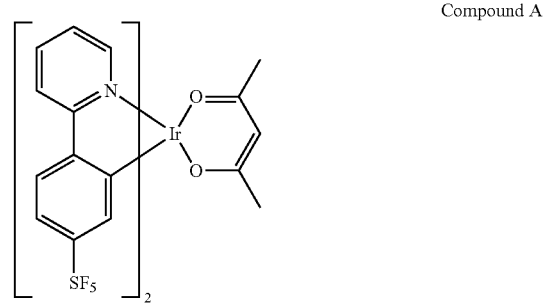

Compound A

Comparative Example 2

An OLED was manufactured in the same manner as in Example 1, except that in forming an EML, Compound B was used instead of Compound 1 as a dopant.

Compound B

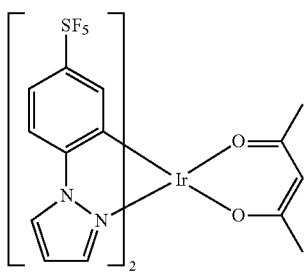

Comparative Example 3

An OLED was manufactured in the same manner as in Example 1, except that in forming an EML, Compound C was used instead of Compound 1 as a dopant.

Compound C

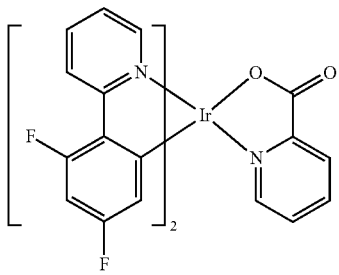

Evaluation Example 2: OLED Characteristics Evaluation

Changes in current density, brightness, and emission efficiency of the OLEDs of Examples 1 and 2 and Comparative Examples 1 to 3 were measured according to voltages applied thereto. A detailed measuring method is described below, and the results thereof are shown in Table 2 below:

(1) Measurement of Changes in Current Density According to Voltages

The current flowing in a unit device of the OLED was measured by using a Keithley 2400 current-voltage meter with respect to voltages rising from 0 volts (V) to 10 V, and the measured current value was divided by an area.

(2) Measurement of Changes in Brightness According to Voltages

The brightness of the OLED was measured by using a Minolta Cs-1000A luminance meter with respect to voltages rising from 0 V to 10 V, and the results measured in correspond to each voltage were obtained.

(3) Measurement of Emission Efficiency

The current efficiency (cd/A) of the OLEDs with respect to the same current density (10 milliamperes per square centimeter (mA/cm$^2$)) were calculated based on the brightness, the current density, and the voltage measured in (1) and (2) above.

TABLE 2

| | Host | Dopant | Driving Voltage (V) | CIE Chromaticity Coordinate | |
|---|---|---|---|---|---|
| | | | | CIE x | CIE y |
| Example 1 | ADN | Compound 1 | 6.7 | 0.18 | 0.25 |
| Example 2 | ADN | Compound 2 | 6.5 | 0.17 | 0.22 |
| Comparative Example 1 | ADN | Compound A | 5 | 0.26 | 0.40 |
| Comparative Example 2 | ADN | Compound B | 5.1 | 0.27 | 0.39 |
| Comparative Example 3 | ADN | Compound C | 6.2 | 0.16 | 0.36 |

Referring to color coordinates of Table 2, it was confirmed that the OLEDs of Example 1 and 2 emit deep blue light with high color purity, whereas the OLEDs of Comparative Examples 1 and 2 emit green light, and the OLED of Comparative Example 3 emit blue light with a poor CIE y-coordinate.

Meanwhile, in general, the driving voltage of a device emitting blue light tends to be greater than that of a device emitting green light. In this regard, it was confirmed that although the OLEDs of Examples 1 and 2 emit blue light with high color purity, these OLEDs had low and good driving voltage characteristics.

As described above, according to the one or more of the above embodiments, an organometallic compound has excellent electrical characteristics and thermal stability, and thus an organic light-emitting device including the organometallic compound may have a low driving voltage, high efficiency, high brightness, and long lifespan.

It should be understood that the exemplary embodiments described therein should be considered in a descriptive sense only and not for purposes of limitation. Descriptions of features or aspects within each embodiment should typically be considered as available for other similar features or aspects in other embodiments.

While one or more embodiments have been described with reference to the figures, it will be understood by those of ordinary skill in the art that various changes in form and details may be made therein without departing from the spirit and scope of the present disclosure as defined by the following claims.

What is claimed is:

1. An organometallic compound having Formula 1:

$$M(L_1)_{n1}(L_2)_{n2} \qquad \text{Formula 1}$$

wherein in Formula 1,
M is Ir, Pt, Os, Ti, Zr, Hf, Eu, Tb, or Tm;
$L_1$ is a divalent ligand having one of Formulae 2A to 2E; and Formula 2A

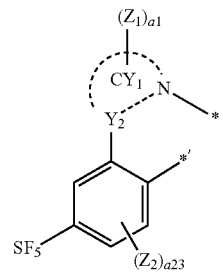

Formula 2B

Formula 2C

Formula 2D

Formula 2E wherein in Formulae 2A to 2E,

N and $Y_2$ are connected to each other via a single bond or a double bond, and $CY_1$ is a $C_5$-$C_{60}$ carbocyclic group or a $C_2$-$C_{60}$ heterocyclic group;

$Z_1$ and $Z_2$ are each independently a hydrogen, a deuterium, —F, —Cl, —Br, —I, a hydroxyl group, a cyano group, a nitro group, an amino group, an amidino group, a hydrazine group, a hydrazone group, a carboxylic acid and a salt thereof, a sulfonic acid and a salt thereof, a phosphoric acid and a salt thereof, —SF$_5$, a substituted or unsubstituted $C_1$-$C_{60}$ alkyl group, a substituted or unsubstituted $C_2$-$C_{60}$ alkenyl group, a substituted or unsubstituted $C_2$-$C_{60}$ alkynyl group, a substituted or unsubstituted $C_1$-$C_{60}$ alkoxy group, a substituted or unsubstituted $C_3$-$C_{10}$ cycloalkyl group, a substituted or unsubstituted $C_2$-$C_{10}$ heterocycloalkyl group, a substituted or unsubstituted $C_3$-$C_{10}$ cycloalk-enyl group, a substituted or unsubstituted $C_2$-$C_{10}$ heterocycloalkenyl group, a substituted or unsubstituted $C_6$-$C_{60}$ aryl group, a substituted or unsubstituted $C_6$-$C_{60}$ aryloxy group, a substituted or unsubstituted $C_6$-$C_{60}$ arylthio group, a substituted or unsubstituted $C_2$-$C_{60}$ heteroaryl group, a substituted or unsubstituted monovalent non-aromatic condensed polycyclic group, a substituted or unsubstituted monovalent non-aromatic condensed heteropolycyclic group, —N($Q_1$)($Q_2$), —Si ($Q_3$)($Q_4$)($Q_5$), or —B($Q_6$)($Q_7$);

a1 is an integer of 1 to 5;

a23 is an integer of 1 to 3;

a22 is 1 or 2;

n1 is an integer of 1 to 3;

n2 is an integer of 0 to 4;

each of * and *' indicates a binding site with M of Formula 1 above;

L2 is a ligand having Formula 3-1;

Formula 3-1 wherein in Formula 3-1, $Y_{11}$ to $Y_{14}$ are each independently C or N;

$CY_3$ and $CY_4$ are each independently a $C_5$-$C_{60}$ carbocyclic group or a $C_2$-$C_{60}$ heterocyclic group, $Z_{21}$ and $Z_{22}$ are each independently a hydrogen, a deuterium, —F, —Cl, —Br, —I, a hydroxyl group, a cyano group, a nitro group, an amino group, an amidino group, a hydrazine group, a hydrazone group, a carboxylic acid and a salt thereof, a sulfonic acid and a salt thereof, a phosphoric acid and a salt thereof, a substituted or unsubstituted $C_1$-$C_{60}$ alkyl group, a substituted or unsubstituted $C_2$-$C_{60}$ alkenyl group, a substituted or unsubstituted $C_2$-$C_{60}$ alkynyl group, a substituted or unsubstituted $C_1$-$C_{60}$ alkoxy group, a substituted or unsubstituted $C_3$-$C_{10}$ cycloalkyl group, a substituted or unsubstituted $C_2$-$C_{10}$ heterocycloalkyl group, a substituted or unsubstituted $C_3$-$C_{10}$ cycloalkenyl group, a substituted or unsubstituted $C_2$-$C_{10}$ heterocycloalkenyl group, a substituted or unsubstituted $C_6$-$C_{60}$ aryl group, a substituted or unsubstituted $C_6$-$C_{60}$ aryloxy group, a substituted or unsubstituted $C_6$-$C_{60}$ arylthio group, a substituted or unsubstituted $C_2$-$C_{60}$ heteroaryl group, a substituted or unsubstituted monovalent non-aromatic condensed polycyclic group, or a substituted or unsubstituted monovalent non-aromatic condensed heteropolycyclic group;

c1 and c2 are each independently an integer of 1 to 5;

each of * and *' indicates a binding site to M of Formula 1, wherein at least one substituent of the substituted $C_1$-$C_{60}$ alkyl group, the substituted $C_2$-$C_{60}$ alkenyl group, the substituted $C_2$-$C_{60}$ alkynyl group, the substituted $C_1$-$C_{60}$ alkoxy group, the substituted $C_3$-$C_{10}$ cycloalkyl group, the substituted $C_2$-$C_{10}$ heterocycloalkyl group, the substituted $C_3$-$C_{10}$ cycloalkenyl group, the substituted $C_2$-$C_{10}$ heterocycloalkenyl group, the substituted $C_6$-$C_{60}$ aryl group, the substituted $C_6$-$C_{60}$ aryloxy group, the substituted $C_6$-$C_{60}$ arylthio group, the substituted $C_2$-$C_{60}$ heteroaryl group, the substituted monovalent non-aromatic condensed polycyclic group, and the substituted monovalent non-aromatic condensed heteropolycyclic group is
(A) a deuterium, —F, —Cl, —Br, —I, a hydroxyl group, a cyano group, a nitro group, an amino group, an amidino group, a hydrazine group, a hydrazone group, a carboxylic acid and a salt thereof, a sulfonic acid and a salt thereof, a phosphoric acid and a salt thereof, a $C_1$-$C_{60}$ alkyl group, a $C_2$-$C_{60}$ alkenyl group, a $C_2$-$C_{60}$ alkynyl group, or a $C_1$-$C_{60}$ alkoxy group;
(B) a $C_1$-$C_{60}$ alkyl group, a $C_2$-$C_{60}$ alkenyl group, a $C_2$-$C_{60}$ alkynyl group, or a $C_1$-$C_{60}$ alkoxy group, each of which is substituted with at least one group selected from a deuterium, —F, —Cl, —Br, —I, a hydroxyl group, a cyano group, a nitro group, an amino group, an amidino group, a hydrazine group, a hydrazone group, a carboxylic acid and a salt thereof, a sulfonic acid and a salt thereof, a phosphoric acid and a salt thereof, a $C_3$-$C_{10}$ cycloalkyl group, a $C_2$-$C_{10}$ heterocycloalkyl group, a $C_3$-$C_{10}$ cycloalkenyl group, a $C_2$-$C_{10}$ heterocycloalkenyl group, a $C_6$-$C_{60}$ aryl group, a $C_6$-$C_{60}$ aryloxy group, a $C_6$-$C_{60}$ arylthio group, a $C_2$-$C_{60}$ heteroaryl group, a monovalent non-aromatic condensed polycyclic group, a monovalent non-aromatic condensed heteropolycyclic group, —N($Q_{11}$)($Q_{12}$), —Si($Q_{13}$)($Q_{14}$)($Q_{15}$), and —B($Q_{16}$)($Q_{17}$);
(C) a $C_3$-$C_{10}$ cycloalkyl group, a $C_2$-$C_{10}$ heterocycloalkyl group, a $C_3$-$C_{10}$ cycloalkenyl group, a $C_2$-$C_{10}$ heterocycloalkenyl group, a $C_6$-$C_{60}$ aryl group, a $C_6$-$C_{60}$ aryloxy group, a $C_6$-$C_{60}$ arylthio group, a $C_2$-$C_{60}$ heteroaryl group, a monovalent non-aromatic condensed polycyclic group, or a monovalent non-aromatic condensed heteropolycyclic group, each of which is substituted;
(D) a $C_3$-$C_{10}$ cycloalkyl group, a $C_2$-$C_{10}$ heterocycloalkyl group, a $C_3$-$C_{10}$ cycloalkenyl group, a $C_2$-$C_{10}$ heterocycloalkenyl group, a $C_6$-$C_{60}$ aryl group, a $C_6$-$C_{60}$ aryloxy group, a $C_6$-$C_{60}$ arylthio group, a $C_2$-$C_{60}$ heteroaryl group, a monovalent non-aromatic condensed polycyclic group, or a monovalent non-aromatic condensed heteropolycyclic group, each of which is substituted with at least one group selected from a deuterium, —F, —Cl, —Br, —I, a hydroxyl group, a cyano group, a nitro group, an amino group, an amidino group, a hydrazine group, a hydrazone group, a carboxylic acid and a salt thereof, a sulfonic acid and a salt thereof, a phosphoric acid and a salt thereof, a $C_1$-$C_{60}$ alkyl group, a $C_2$-$C_{60}$ alkenyl group, a $C_2$-$C_{60}$ alkynyl group, a $C_1$-$C_{60}$ alkoxy group, a $C_3$-$C_{10}$ cycloalkyl group, a $C_2$-$C_{10}$ heterocycloalkyl group, a $C_3$-$C_{10}$ cycloalkenyl group, a $C_2$-$C_{10}$ heterocycloalkenyl group, a $C_6$-$C_{60}$ aryl group, a $C_6$-$C_{60}$ aryloxy group, a $C_6$-$C_{60}$ arylthio group, a $C_2$-$C_{60}$ heteroaryl group, a monovalent non-aromatic condensed polycyclic group, a monovalent non-aromatic condensed heteropolycyclic group, —N($Q_{21}$)($Q_{22}$), —Si($Q_{23}$)($Q_{24}$)($Q_{25}$), and —B($Q_{26}$)($Q_{27}$); or
(E) —N($Q_{31}$)($Q_{32}$), —Si($Q_{33}$)($Q_{34}$)($Q_{35}$), or —B($Q_{36}$)($Q_{37}$); and
wherein $Q_1$ to $Q_7$, $Q_{11}$ to $Q_{17}$, $Q_{21}$ to $Q_{27}$, and $Q_{31}$ to $Q_{37}$ are each independently a hydrogen, a deuterium, —F, —Cl, —Br, —I, a hydroxyl group, a cyano group, a nitro group, an amino group, an amidino group, a hydrazine group, a hydrazone group, a carboxylic acid and a salt thereof, a sulfonic acid and a salt thereof, a phosphoric acid and a salt thereof, a $C_1$-$C_{60}$ alkyl group, a $C_2$-$C_{60}$ alkenyl group, a $C_2$-$C_{60}$ alkynyl group, a $C_1$-$C_{60}$ alkoxy group, a $C_3$-$C_{10}$ cycloalkyl group, a $C_2$-$C_{10}$ heterocycloalkyl group, a $C_3$-$C_{10}$ cycloalkenyl group, a $C_2$-$C_{10}$ heterocycloalkenyl group, a $C_6$-$C_{60}$ aryl group, a $C_6$-$C_{60}$ aryloxy group, a $C_6$-$C_{60}$ arylthio group, a $C_2$-$C_{60}$ heteroaryl group, a monovalent non-aromatic condensed polycyclic group, or a monovalent non-aromatic condensed heteropolycyclic group.

2. The organometallic compound of claim 1, wherein $CY_1$ is benzene, naphthalene, fluorenene, spiro-fluorenene, indene, pyrrole, thiophene, furan, imidazole, pyrazole, thiazole, isothiazole, oxazole, isooxazole, triazole, pyridine, pyrazine, pyrimidine, pyridazine, quinoline, isoquinoline, benzoquinoline, quinoxaline, quinazoline, carbazole, benzoimidazole, benzofuran, benzothiophene, isobenzothiophene, benzooxazole, isobenzooxazole, triazole, tetrazole, oxadiazole, triazine, dibenzofuran, or dibenzothiophene.

3. The organometallic compound of claim 1, wherein $CY_1$ is pyridine, triazole, imidazole, or pyrazole.

4. The organometallic compound of claim 1, wherein $Z_1$ and $Z_2$ are each independently
(A) a hydrogen, a deuterium, —F, —Cl, —Br, —I, a hydroxyl group, a cyano group, a nitro group, an amino group, an amidino group, a hydrazine group, a hydrazone group, a carboxylic acid and a salt thereof, a sulfonic acid and a salt thereof, a phosphoric acid and a salt thereof, —$SF_5$, a $C_1$-$C_{20}$ alkyl group, or a $C_1$-$C_{20}$ alkoxy group;
(B) a $C_1$-$C_{20}$ alkyl group or a $C_1$-$C_{20}$ alkoxy group, each of which is substituted with at least one group selected from a deuterium, —F, —Cl, —Br, —I, a hydroxyl group, a cyano group, a nitro group, an amino group, an amidino group, a hydrazine group, a hydrazone group, a carboxylic acid and a salt thereof, a sulfonic acid and a salt thereof, a phosphoric acid and a salt thereof, a phenyl group, a naphthyl group, a pyridinyl group, and a pyrimidinyl group;
(C) a phenyl group, a naphthyl group, a fluorenyl group, a phenanthrenyl group, an anthracenyl group, a fluoranthrenyl group, a triphenylenyl group, a pyrenyl group, a chrysenyl group, a pyrrolyl group, a thiophenyl group, a furanyl group, an imidazolyl group, a pyrazolyl group, a thiazolyl group, an isothiazolyl group, an oxazolyl group, an isooxazolyl group, a pyridinyl group, a pyrazinyl group, a pyrimidinyl group, a pyridazinyl group, an isoindolyl group, an indolyl group, an indazolyl group, a purinyl group, a quinolinyl group, an isoquinolinyl group, a benzoquinolinyl group, a quinoxalinyl group, a quinazolinyl group, a cinnolinyl group, a carbazolyl group, a phenanthrolinyl group, a benzoimidazolyl group, a benzofuranyl group, a benzothiophenyl group, an isobenzothiazolyl group, a benzooxazolyl group, an isobenzooxazolyl group, a triazolyl group, a tetrazolyl group, an oxadiazolyl group, a triazinyl group, a dibenzofuranyl group, a dibenzothiophenyl group, a benzocarbazolyl group, a dibenzocarbazolyl group, an imidazopyridinyl group, or an imidazopyrimidinyl group, each of which is unsubstituted; or
(D) a phenyl group, a naphthyl group, a fluorenyl group, a phenanthrenyl group, an anthracenyl group, a fluoranthrenyl group, a triphenylenyl group, a pyrenyl group, a chrysenyl group, a pyrrolyl group, a thiophenyl group, a furanyl group, an imidazolyl group, a pyrazolyl group, a thiazolyl group, an isothiazolyl group, an oxazolyl group, an isooxazolyl group, a pyridinyl group, a pyrazinyl group, a pyrimidinyl group, a pyridazinyl group, an isoindolyl group, an indolyl group, an indazolyl group, a purinyl group, a quinolinyl group, an isoquinolinyl group, a benzoquinolinyl group, a quinoxalinyl group, a quinazolinyl group, a cinnolinyl group, a carbazolyl group, a phenanthrolinyl group, a benzoimidazolyl group, a benzofuranyl group, a benzothiophenyl group, an isobenzothiazolyl group, a benzooxazolyl group, an isobenzooxazolyl group, a triazolyl group, a tetrazolyl group, an oxadiazolyl group, a triazinyl group, a dibenzofuranyl group, a dibenzothiophenyl group, a benzocarbazolyl group, a dibenzocarbazolyl group, an imidazopyridinyl group, or an imidazopyrimidinyl group, each of which is substituted with at least one group selected from a deuterium, —F, —Cl, —Br, —I, a hydroxyl group, a cyano group, a nitro group, an amino group, an amidino group, a hydrazine group, a hydrazone group, a carboxylic acid and a salt thereof, a sulfonic acid and a salt thereof, a phosphoric acid and a salt thereof, a $C_1$-$C_{20}$ alkyl group, a $C_1$-$C_{20}$ alkoxy group, a phenyl group, a naphthyl group, a fluorenyl group, a phenanthrenyl group, an anthracenyl group, a fluoranthrenyl group, a triphenylenyl group, a pyrenyl group, a chrysenyl group, a pyrrolyl group, a thiophenyl group, a furanyl group, an imidazolyl group, a pyrazolyl group, a thiazolyl group, an isothiazolyl group, an oxazolyl group, an isooxazolyl group, a pyridinyl group, a pyrazinyl group, a pyrimidinyl group, a pyridazinyl group, an isoindolyl group, an indolyl group, an indazolyl group, a purinyl group, a quinolinyl group, an isoquinolinyl group, a benzoquinolinyl group, a quinoxalinyl group, a quinazolinyl group, a cinnolinyl group, a carbazolyl group, a phenanthrolinyl group, a benzoimidazolyl group, a benzofuranyl group, a benzothiophenyl group, an isobenzothiazolyl group, a benzooxazolyl group, an isobenzooxazolyl group, a triazolyl group, a tetrazolyl group, an oxadiazolyl group, a triazinyl group, a dibenzofuranyl group, a dibenzothiophenyl group, a benzocarbazolyl group, a dibenzocarbazolyl group, an imidazopyridinyl group, and an imidazopyrimidinyl group.

5. The organometallic compound of claim 1, wherein $Z_1$ and $Z_2$ are each independently (A) a hydrogen, —F, a cyano group, a nitro group, —$SF_5$, a methyl group, an ethyl group, a propyl group, an n-butyl group, an isobutyl group, a sec-butyl group, a tert-butyl group, an n-pentyl group, an isopentyl group, a sec-pentyl group, a tert-pentyl group, an n-hexyl group, an isohexyl group, a sec-hexyl group, a tert-hexyl group, an n-heptyl group, an isoheptyl group, a sec-heptyl group, a tert-heptyl group, an n-octyl group, an isooctyl group, a sec-octyl group, a tert-octyl group, an n-nonyl group, an isononyl group, a sec-nonyl group, a tert-nonyl group, an n-decanyl group, an isodecanyl group, a sec-decanyl group, a tert-decanyl group, a methoxy group, an ethoxy group, a propoxy group, a butoxy group, a pentoxy group, a phenyl group, a naphthyl group, a pyridinyl group, a pyrimidinyl group, or a triazinyl group, each of which is unsubstituted; or (B) a methyl group, an ethyl group, a propyl group, an n-butyl group, an isobutyl group, a sec-butyl group, a tert-butyl group, an n-pentyl group, an isopentyl group, a sec-pentyl group, a tert-pentyl group, an n-hexyl group, an isohexyl group, a sec-hexyl group, a tert-hexyl group, an n-heptyl group, an isoheptyl group, a sec-heptyl group, a tert-heptyl group, an n-octyl group, an isooctyl group, a sec-octyl group, a tert-octyl group, an n-nonyl group, an isononyl group, a sec-nonyl group, a tert-nonyl group, an n-decanyl group, an isodecanyl group, a sec-decanyl group, a tert-decanyl group, a methoxy group, an ethoxy group, a propoxy group, a butoxy group, a pentoxy group, a phenyl group, a naphthyl group, a pyridinyl group, a pyrimidinyl group, or a triazinyl group, each of which is substituted with at least one group selected from —F, a cyano group, and a nitro group.

6. The organometallic compound of claim 1, wherein $CY_3$ and $CY_4$ are each independently benzene, naphthalene, fluorene, spiro-fluorene, indene, pyrrole, thiophene, furan, imidazole, pyrazole, thiazole, isothiazole, oxazole, isooxazole, triazole, pyridine, pyrazine, pyrimidine, pyridazine, quinoline, isoquinoline, benzoquinoline, quinoxaline, quinazoline, carbazole, benzoimidazole, benzofuran, benzothiophene, isobenzothiophene, benzooxazole, isobenzooxazole, triazole, tetrazole, oxadiazole, triazine, dibenzofuran, or dibenzothiophene;

$Z_{21}$ and $Z_{22}$ are each independently (A) a hydrogen, a deuterium, —F, —Cl, —Br, —I, a hydroxyl group, a cyano group, a nitro group, an amino group, an amidino group, a hydrazine group, a hydrazone group, a carboxylic acid and a salt thereof, a sulfonic acid and a salt thereof, a phosphoric acid and a salt thereof, a $C_1$-$C_{20}$ alkyl group, or a $C_1$-$C_{20}$ alkoxy group;

(B) a $C_1$-$C_{20}$ alkyl group or a $C_1$-$C_{60}$ alkoxy group, each of which is substituted with at least one group selected from a deuterium, —F, —Cl, —Br, —I, a hydroxyl group, a cyano group, a nitro group, an amino group, an amidino group, a hydrazine group, a hydrazone group, a carboxylic acid and a salt thereof, a sulfonic acid and a salt thereof, a phosphoric acid and a salt thereof, a phenyl group, a naphthyl group, a pyridinyl group, and a pyrimidinyl group;

(C) a phenyl group, a naphthyl group, a fluorenyl group, a phenanthrenyl group, an anthracenyl group, a fluoranthrenyl group, a triphenylenyl group, a pyrenyl group, a chrysenyl group, a pyrrolyl group, a thiophenyl group, a furanyl group, an imidazolyl group, a pyrazolyl group, a thiazolyl group, an isothiazolyl group, an oxazolyl group, an isooxazolyl group, a pyridinyl group, a pyrazinyl group, a pyrimidinyl group, a pyridazinyl group, an isoindolyl group, an indolyl group, an indazolyl group, a purinyl group, a quinolinyl group, an isoquinolinyl group, a benzoquinolinyl group, a quinoxalinyl group, a quinazolinyl group, a cinnolinyl group, a carbazolyl group, a phenanthrolinyl group, a benzoimidazolyl group, a benzofuranyl group, a benzothiophenyl group, an isobenzothiazolyl group, a benzooxazolyl group, an isobenzooxazolyl group, a triazolyl group, a tetrazolyl group, an oxadiazolyl group, a triazinyl group, a dibenzofuranyl group, a dibenzothiophenyl group, a benzocarbazolyl group, a dibenzocarbazolyl group, an imidazopyridinyl group, or an imidazopyrimidinyl group, each of which is unsubstituted; or (D) a phenyl group, a naphthyl group, a fluorenyl group, a phenanthrenyl group, an anthracenyl group, a fluoranthrenyl group, a triphenylenyl group, a pyrenyl group, a chrysenyl group, a pyrrolyl group, a thiophenyl group, a furanyl group, an imidazolyl group, a pyrazolyl group, a thiazolyl group, an isothiazolyl group, an oxazolyl group, an isooxazolyl group, a pyridinyl group, a pyrazinyl group, a pyrimidinyl group, a pyridazinyl group, an isoindolyl group, an indolyl group, an indazolyl group, a purinyl group, a quinolinyl group, an isoquinolinyl group, a benzoquinolinyl group, a quinoxalinyl group, a quinazolinyl group, a cinnolinyl group, a carbazolyl group, a phenanthrolinyl group, a benzoimidazolyl group, a benzofuranyl group, a benzothiophenyl group, an isobenzothiazolyl group, a benzooxazolyl group, an isobenzooxazolyl group, a triazolyl group, a tetrazolyl group, an oxadiazolyl group, a triazinyl group, a dibenzofuranyl group, a dibenzothiophenyl group, a benzocarbazolyl group, a dibenzocarbazolyl group, an imidazopyridinyl group, or an imidazopyrimidinyl group, each of which is substituted with at least one group selected from a deuterium, —F, —Cl, —Br, —I, a hydroxyl group, a cyano group, a nitro group, an amino group, an amidino group, a hydrazine group, a hydrazone group, a carboxylic acid and a salt thereof, a sulfonic acid and a salt thereof, a phosphoric acid and a salt thereof, a $C_1$-$C_{20}$ alkyl group, a $C_1$-$C_{20}$ alkoxy group, a phenyl group, a naphthyl group, a fluorenyl group, a phenanthrenyl group, an anthracenyl group, a fluoranthrenyl group, a triphenylenyl group, a pyrenyl group, a chrysenyl group, a pyrrolyl group, a thiophenyl group, a furanyl group, an imidazolyl group, a pyrazolyl group, a thiazolyl group, an isothiazolyl group, an oxazolyl group, an isooxazolyl group, a pyridinyl group, a pyrazinyl group, a pyrimidinyl group, a pyridazinyl group, an isoindolyl group, an indolyl group, an indazolyl group, a purinyl group, a quinolinyl group, an isoquinolinyl group, a benzoquinolinyl group, a quinoxalinyl group, a quinazolinyl group, a cinnolinyl group, a carbazolyl group, a phenanthrolinyl group, a benzoimidazolyl group, a benzofuranyl group, a benzothiophenyl group, an isobenzothiazolyl group, a benzooxazolyl group, an isobenzooxazolyl group, a triazolyl group, a tetrazolyl group, an oxadiazolyl group, a triazinyl group, a dibenzofuranyl group, a dibenzothiophenyl group, a benzocarbazolyl group, a dibenzocarbazolyl group, an imidazopyridinyl group, and an imidazopyrimidinyl group; and c1 and c2 are each independently 1 or 2.

7. The organometallic compound of claim 1, wherein $CY_3$ is pyridine, triazole, imidazole, or pyrazole, $CY_4$ is benzene or pyridine, and at least one of $Y_{11}$ and $Y_{14}$ is N;

$Z_{21}$ and $Z_{22}$ are each independently, (A) a hydrogen, —F, a cyano group, a nitro group, a methyl group, an ethyl group, a propyl group, an n-butyl group, an isobutyl group, a sec-butyl group, a tert-butyl group, an n-pentyl group, an isopentyl group, a sec-pentyl group, a tert-pentyl group, an n-hexyl group, an isohexyl group, a sec-hexyl group, a tert-hexyl group, an n-heptyl group, an isoheptyl group, a sec-heptyl group, a tert-heptyl group, an n-octyl group, an isooctyl group, a sec-octyl group, a tert-octyl group, an n-nonyl group, an isononyl group, a sec-nonyl group, a tert-nonyl group, an n-decanyl group, an isodecanyl group, a sec-decanyl group, a tert-decanyl group, a methoxy group, an ethoxy group, a propoxy group, a butoxy group, a pentoxy group, a phenyl group, a naphthyl group, a pyridinyl group, a pyrimidinyl group, or a triazinyl group, each of which is unsubstituted; or (B) a methyl group, an ethyl group, a propyl group, an n-butyl group, an isobutyl group, a sec-butyl group, a tert-butyl group, an n-pentyl group, an isopentyl group, a sec-pentyl group, a tert-pentyl group, an n-hexyl group, an isohexyl group, a sec-hexyl group, a tert-hexyl group, an n-heptyl group, an isoheptyl group, a sec-heptyl group, a tert-heptyl group, an n-octyl group, an isooctyl group, a sec-octyl group, a tert-octyl group, an n-nonyl group, an isononyl group, a sec-nonyl group, a tert-nonyl group, an n-decanyl group, an isodecanyl group, a sec-decanyl group, a tert-decanyl group, a methoxy group, an ethoxy group, a propoxy group, a butoxy group, a pentoxy group, a phenyl group, a naphthyl group, a pyridinyl group, a pyrimidinyl group, or a triazinyl group, each of which is substituted with at least one group selected from —F, a cyano group, and a nitro group; and c1 and c2 are each independently 1 or 2.

8. The organometallic compound of claim 1, wherein when n1 is 3, all three groups $L_1$ are identical; and when n2 is 2, groups $L_1$ are identical.

9. An organometallic compound selected from the group consisting of Compounds 2 to 24:

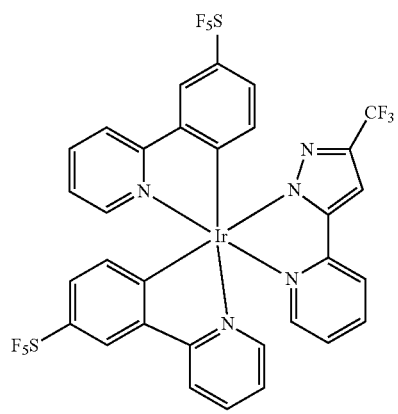

2

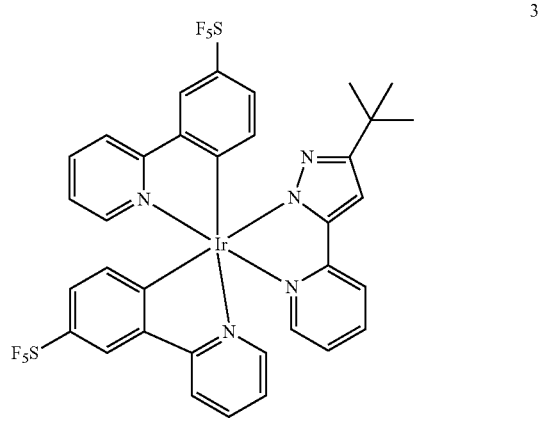

3

103
-continued
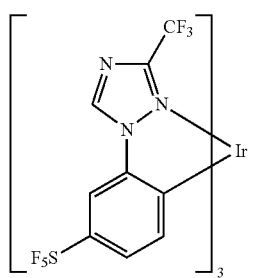
4
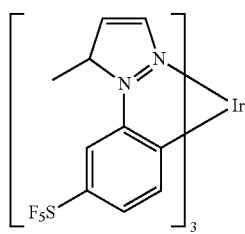
5
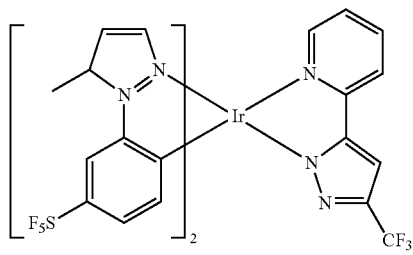
6
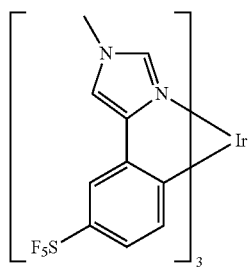
7
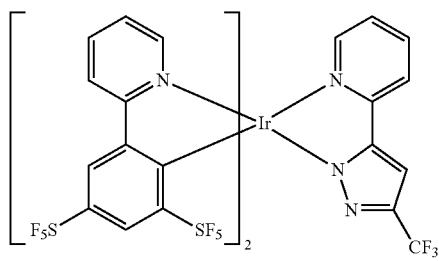
8
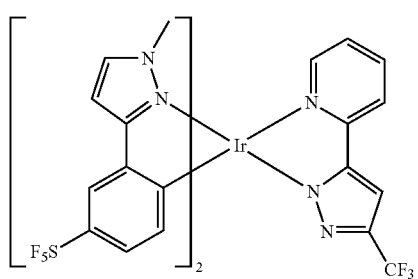
9
104
-continued
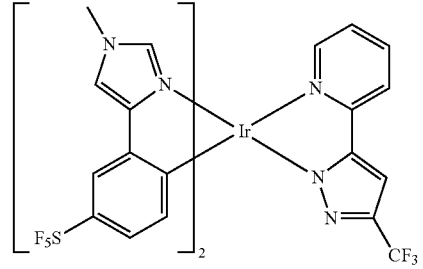
10
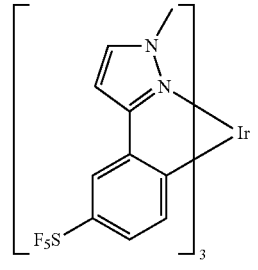
11
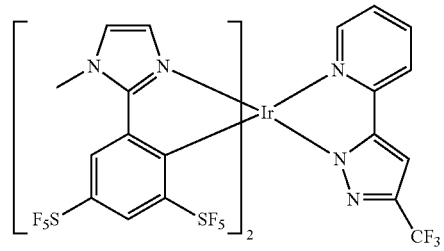
12
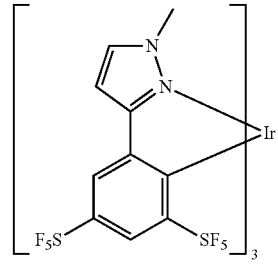
13
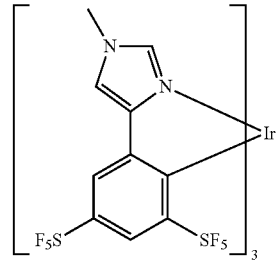
14
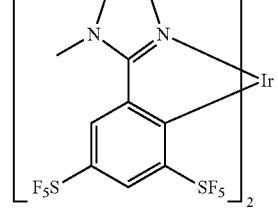
15

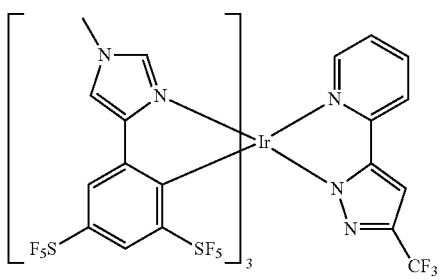

16

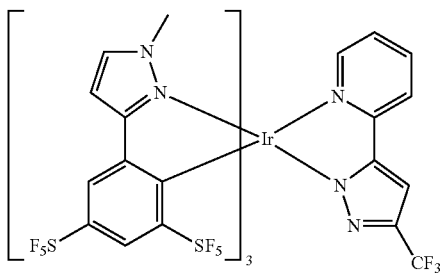

17

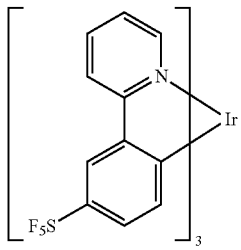

18

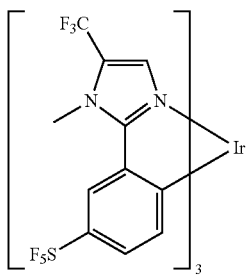

19

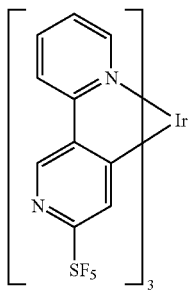

20

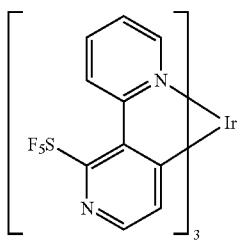

21

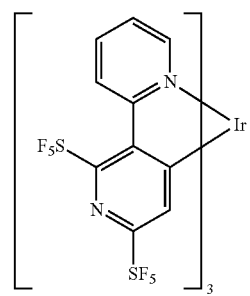

22

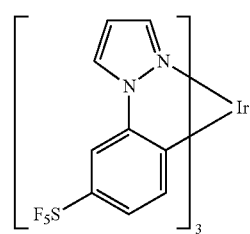

23

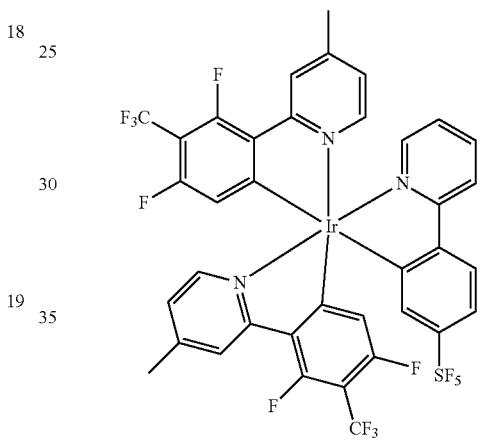

24

10. An organic light-emitting device comprising:
a first electrode;
a second electrode; and
an organic layer disposed between the first electrode and the second electrode,
wherein the organic layer comprises an emission layer, and
wherein the organic layer includes at least one organometallic compound of claim 1.

11. The organic light-emitting device of claim 10, wherein
the first electrode is an anode,
the second electrode is a cathode, and
the organic layer comprises
i) a hole transport region disposed between the first electrode and the emission layer,
wherein the hole transport region comprises at least one of a hole injection layer, a hole transport layer, and an electron blocking layer; and
ii) an electron transport region disposed between the emission layer and the second electrode,
wherein the electron transport region comprises at least one of a hole blocking layer, an electron transport layer, and an electron injection layer.

12. The organic light-emitting device of claim 10, wherein the emission layer comprises the organometallic compound, and further comprises a host, wherein an amount of the organometallic compound is smaller than an amount of the host.

13. The organic light-emitting device of claim 10, wherein the organic light-emitting device emits deep blue light having a maximum emission wavelength in a range of about 435 nanometers to about 500 nanometers, x-color coordinates in a range of about 0.14 to about 0.20, and y-color coordinates in a range of about 0.10 to about 0.35.

\* \* \* \* \*